US008993276B2

(12) United States Patent
Xu et al.

(10) Patent No.: US 8,993,276 B2
(45) Date of Patent: Mar. 31, 2015

(54) CHIMERIC ENZYMES WITH IMPROVED CELLULASE ACTIVITIES

(71) Applicant: Alliance for Sustainable Energy, LLC, Golden, CO (US)

(72) Inventors: Qi Xu, Lakewood, CO (US); John O. Baker, Golden, CO (US); Michael E. Himmel, Littleton, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

(21) Appl. No.: 13/940,936

(22) Filed: Jul. 12, 2013

(65) Prior Publication Data

US 2014/0017734 A1 Jan. 16, 2014

Related U.S. Application Data

(60) Provisional application No. 61/671,454, filed on Jul. 13, 2012.

(51) Int. Cl.
| | |
|---|---|
| *C12P 19/14* | (2006.01) |
| *C12N 9/96* | (2006.01) |
| *C12N 9/14* | (2006.01) |
| *C12N 9/24* | (2006.01) |
| *C12P 21/06* | (2006.01) |
| *C12P 19/34* | (2006.01) |
| *C12N 15/00* | (2006.01) |
| *C12N 1/20* | (2006.01) |
| *C07H 21/04* | (2006.01) |
| *C07K 1/00* | (2006.01) |
| *C12N 9/42* | (2006.01) |

(52) U.S. Cl.
CPC ............. *C12P 19/14* (2013.01); *C12N 9/2437* (2013.01)
USPC ............ 435/99; 435/188; 435/195; 435/200; 435/69.1; 435/91.1; 435/320.1; 435/252.33; 435/252.3; 536/23.1; 536/23.2; 530/350

(58) Field of Classification Search
CPC ....... C12N 9/2437; C12N 15/75; C12N 9/644
USPC ................. 435/99, 188, 195, 200, 69.1, 91.1, 435/320.1, 252.33, 252.3; 536/23.1, 23.2; 530/350
See application file for complete search history.

(56) References Cited

U.S. PATENT DOCUMENTS

| 4,952,501 A | 8/1990 | Jasin et al. | |
|---|---|---|---|
| 2012/0083012 A1* | 4/2012 | Chang et al. | ..................... 435/41 |
| 2013/0189745 A1* | 7/2013 | Schwarz et al. | ................ 435/99 |

OTHER PUBLICATIONS

VanFossen et al., Glycoside Hydrolase Inventory Drives Plant Polysaccharide Deconstruction by the Extremely Thermophilic Bacterium *Caldicellulosiruptor saccharolyticus*. Biotechnology and Bioengineering, vol. 108, No. 7, 1559-1569, 2011.*
Witkowski et al., Conversion of a β-Ketoacyl Synthase to a Malonyl Decarboxylase by Replacement of the Active-Site Cysteine with Glutamine. Biochemistry 38:11643-11650, 1999.*
Seffernick et al., Melamine Deaminase and Atrazine Chlorohydrolase: 98 Percent Identical but Functionally Different. J. Bacteriol. 183(8):2405-2410, 2001.*
Liu et al., Cloning of Thermostable Cellulase Genes of *Clostridium thermocellum* and Their Secretive Expression in *Bacillus subtilis*. Appl Biochem. Biotechnol. 166:652-662, Published online Nov. 19, 2011.*
Gibbs et al., Multidomain and Multifunctional Glycosyl Hydrolases from the Extreme Thermophile *Caldicellulosiruptor* Isolate Tok7B. 1. Current microbiology. vol. 40: pp. 333-340, 2000.*
Ossowski et al., Protein Disorder: Conformational Distribution of the Flexible Linker in a Chimeric Double Cellulase. Biophysical Journal vol. 88: 2823-2832, 2005.*
Telke et al., Construction and characterization of chimeric cellulases with enhanced catalytic activity towards insoluble cellulosic substrates. Biores. Technol., 2012, vol. 112: 10-17.*
Dam et al., "Insights into plant biomass conversion from the genome of the anaerobic thermophilic bacterium *Caldicellulosiruptor bescii* DSM 6725", Nucleic Acids Research, Jan. 2011, vol. 39, No. 8, pp. 3240-3254.
Gilad et al., "Cell, a Noncellulosomal Family 9 Enzyme from *Clostridium thermocellum*, Is a Processive Endoglucanase That Degrades Crystalline Cellulose", Journal of Bacteriology, Jan. 2003, vol. 185, No. 2, pp. 391-398.
Li et al., "Two Cellulases, CeIA and CeIC, from the Polycentric Anaerobic Fungus *Orpinomyces* Strain PC-2 Contain N-Terminal Docking Domains for a Cellulase-Hemicellulase Complex", Applied and Environmental Microbiology, Dec. 1997, vol. 63, No. 12, pp. 4721-4728.
Robinson et al., "Optimizing the stability of single-chain proteins by linker length and composition mutagenesis", Proceedings of the National Academy of Sciences of the United States of America, May 26, 1998, vol. 95, No. 11, pp. 5929-5934.
Wilson, "Cellulases and biofuels", Current Opinion in Biotechnology, Jun. 2009, vol. 20, Issue 3, pp. 295-299.

* cited by examiner

*Primary Examiner* — Ganapathirama Raghu
(74) *Attorney, Agent, or Firm* — John C. Stolpa

(57) ABSTRACT

Nucleic acid molecules encoding chimeric cellulase polypeptides that exhibit improved cellulase activities are disclosed herein. The chimeric cellulase polypeptides encoded by these nucleic acids and methods to produce the cellulases are also described, along with methods of using chimeric cellulases for the conversion of cellulose to sugars such as glucose.

14 Claims, 14 Drawing Sheets

Figure 1

SEQ ID NO:1

```
ATGAAATTTAGAAGGTCAATTTGTACTGCTGTTTTGTTGGCGGTTTTATTGACACTTCTGGTACCGACATCCGTG
TTTGCCTTAGAAGATAATTCTTCGACTTTGCCGCCGTATAAAAACGACCTTTTGTATGAGAGGACTTTTGATGAG
GGACTTTGTTATCCATGGCATACCTGTGAAGACAGCGGAGGAAAATGCTCCTTTGATGTGGTCGATGTTCCGGGG
CAGCCCGGTAATAAAGCATTTGCCGTTACTGTTCTTGACAAAGGGCAAAACAGATGGAGCGTTCAGATGAGACAC
CGTGGTCTTACTCTTGAACAGGGACATACATATAGAGTACGGCTTAAGATTTGGGCAGATGCGTCCTGTAAAGTT
TATATAAAAATAGGACAAATGGGCGAGCCCTATGCTGAATATTGGAACAACAAGTGGAGTCCATACACACTGACA
GCAGGTAAGGTATTGGAAATTGACGAGACGTTTGTTATGGACAAGCCAACTGACGACACATGCGAATTTACATTC
CATTTAGGTGGCGAATTGGCAGCAACTCCTCCATATACAGTTTATCTTGATGATGTATCCCTTTATGACCCAGAA
TATACGAAGCCTGTTGAATATATACTTCCGCAGCCTGATGTACGTGTGAACCAGGTTGGCTACCTGCCGGAGGGC
AAGAAAGTTGCCACTGTGGTATGCAATTCAACTCAGCCGGTAAAATGGCAGCTTAAGAATGCTGCAGGCGTTGTA
GTTTTGGAAGGTTATACCGAACCAAAGGGTCTTGACAAAGACTCGCAGGATTATGTACATTGGCTTGATTTTTCC
GATTTTGCAACCGAAGGAATTGGTTACTATTTTGAACTTCCGACTGTAAACAGTCCTACAAACTACAGTCATCCA
TTTGACATTCGCAAAGACATCTATACTCAGATGAAATATGATGCATTGGCATTCTTCTATCACAAGAGAAGCGGT
ATTCCTATTGAAATGCCGTATGCAGGAGGAGAACAGTGGACCAGACCTGCAGGACATATCGGAATTGAGCCGAAC
AAGGGAGATACAAATGTTCCTACATGGCCTCAGGATGATGAGTATGCAGGAATACCTCAGAAGAATTATACAAAG
GATGTAACCGGTGGATGGTATGATGCCGGTGACCACGGTAAATATGTTGTAAACGGCGGTATAGCCGTCTGGACA
TTAATGAACATGTATGAGAGGGCAAAAATTAGAGGTCTTGACAACTGGGGACCATACAGGGACGGCGGAATGAAC
ATACCGGAGCAGAATAACGGTTATCCGGACATTCTTGATGAAGCAAGATGGGAAATTGAGTTCTTTAAGAAAATG
CAGGTAACTGAAAAAGAGGATCCTTCCATAGCCGGAATGGTACACCACAAAATTCACGACTTCAGATGGACTGCT
TTGGGTATGTTGCCTCACGAAGATCCCCAGCCACGTTACTTAAGGCCGGTAAGTACGGCTGCGACTTTGAACTTT
GCGGCAACTTTGGCACAAAGTGCACGTCTTTGGAAAGATTATGATCCGACTTTTGCTGCTGACTGTTTGGAAAAG
GCTGAAATAGCATGGCAGGCGGCATTAAAGCATCCTGATATTTATGCTGAGTATACTCCCGGTAGCGGTGGTCCC
GGAGGCGGACCATACAATGACGACTATGTCGGAGACGAATTCTACTGGGCAGCCTGCGAACTTTATGTAACAACA
GGAAAAGACGAATATAAGAATTACCTGATGAATTCACCTCACTATCTTGAAATGCCTGCAAAGATGGGTGAAAAC
GGTGGAGCAAACGGAGAAGACAACGGATTGTGGGGATGCTTCACCTGGGGAACTACTCAAGGATTGGGAACCATT
ACTCTTGCATTGGTTGAAAACGGATTGCCTGCTACAGACATTCAAAAGGCAAGAAACAATATAGCTAAAGCTGCT
GACAGATGGCTTGAGAATATTGAAGAGCAAGGTTACAGACTGCCGATCAAACAGGCGGAGGATGAGAGAGGCGGT
TATCCATGGGGTTCAAACTCCTTCATTTTGAACCAGATGATAGTTATGGGATATGCCTATGACTTTACAGGTGAC
TCCAAATATCTCGATGGAATGTTTGACGGCATAAGCTACCTGTTGGGAAGAAACGCAATGGATCAGTCCTATGTA
ACAGGGTATGGTGAGCGTCCGCTTCAGAATCCTCATGACAGGTTCTGGACGCCGCAGACAAGTAAGAGATTCCCT
GCTCCACCTCCGGGTATAATTTCCGGCGGTCCGAACTCCCGTTTCGAGGACCCCGACAATAAATGCGGCCGTTAAG
AAGGATACACCGCCACAGAAATGTTTATCGACCATACAGACTCATGGTCAACCAACGAGATAACTGTTAACTGG
AATGCTCCGTTTGCATGGGTTACAGCTTATCTTGACGAGCAGTACACAGACAGTGAAACCGATAAGGTAACTATT
GATTCGCCTGTTGCAGGAGAAAGATTTGAAGCCGGTAAAGACATTAATATAAGCGCAACTGTTAAATCAAAAACT
CCTGTAAGCAAAGTAGAGTTTTACAATGGAGATACGCTTATTTCCAGTGACACAACTGCACCTTACACAGCAAAG
ATAACAGGAGCCGCTGTCGGAGCATATAACCTTAAAGCGGTTGCAGTGCTGTCTGACGGAAGAAGAATTGAGTCA
CCGGTAACTCCTGTACTTGTTAAGGTAATTGTGAAACCTACTGTAAAACTTACTGCACCCAAGTCAAATGTTGTG
GCTTATGGAAATGAGTTCCTGAAGATTACAGCAACAGCCAGTGACTCTGACGGCAAAATCTCCAGGGTTGATTTC
CTTGTTGACGGTGAAGTAATCGGTTCAGACAGGGAAGCACCTTATGAATATGAGTGGAAAGCTGTGGAAGGCAAT
CACGAAATAAGTGTAATTGCTTATGATGATGACGATGCGGCTTCAACACCTGATTCCGTAAAAATATTTGTAAAA
CAGGCACGGGATGTAAAAGTACAGTATTTGTGCGAAAATACGCAAACATCCACTCAGGAAATCAAGGGTAAATTC
AATATAGTTAACACAGGAAACAGAGATTATTCGCTGAAAGATATAGTATTAAGATACTACTTTACCAAGGAGCAC
AATTCACAGCTTCAGTTTATCTGCTATTATACACCCATAGGCTCCGGAAATCTCATTCCGTCCTTTGGCGGCTCG
GGTGACGAGCATTATCTGCAGCTGGAATTCAAAGATGTCAAGCTGCCTGCCGGCGGTCAGACTGGGGAAATACAG
TTTGTTATAAGATATGCAGATAACTCCTTCCATGATCAGTCGAACGACTATTCGTTCGATCCAACTATAAAAGCG
TTCCAGGATTATGGCAAGGTTACCCTGTATAAGAATGGAGAACTTGTTTGGGGAACGCCGCCGGGCGGTACAGAA
CCTGAAGAACCGGAAGAGCCTGCGATAGTTTACGGCGACTGTAATGATGACGGCAAAGTAAATTCAACAGACGTC
GCAGTAATGAAGAGATATTTAAAGAAGAAAATGTTAATATTAATCTTGACAATGCAGATGTGAATGCGGACGGC
AAAGTTAACTCAACAGACTTCTCAATACTTAAGAGATATGTTATGAAGAACATAGAAGAATTGCCATATCGA
```

Figure 2

SEQ ID NO:2

MKFRRSICTAVLLAVLLTLLVPTSVFALEDNSSTLPPYKNDLLYERTFDEGLCYPWHTCEDS
GGKCSFDVVDVPGQPGNKAFAVTVLDKGQNRWSVQMRHRGLTLEQGHTYRVRLKIWADASCK
VYIKIGQMGEPYAEYWNNKWSPYTLTAGKVLEIDETFVMDKPTDDTCEFTFHLGGELAATPP
YTVYLDDVSLYDPEYTKPVEYILPQPDVRVNQVGYLPEGKKVATVVCNSTQPVKWQLKNAAG
VVVLEGYTEPKGLDKDSQDYVHWLDFSDFATEGIGYYFELPTVNSPTNYSHPFDIRKDIYTQ
MKYDALAFFYHKRSGIPIEMPYAGGEQWTRPAGHIGIEPNKGDTNVPTWPQDDEYAGIPQKN
YTKDVTGGWYDAGDHGKYVVNGGIAVWTLMNMYERAKIRGLDNWGPYRDGGMNIPEQNNGYP
DILDEARWEIEFFKKMQVTEKEDPSIAGMVHHKIHDFRWTALGMLPHEDPQPRYLRPVSTAA
TLNFAATLAQSARLWKDYDPTFAADCLEKAEIAWQAALKHPDIYAEYTPGSGGPGGGPYNDD
YVGDEFYWAACELYVTTGKDEYKNYLMNSPHYLEMPAKMGENGGANGEDNGLWGCFTWGTTQ
GLGTITLALVENGLPATDIQKARNNIAKAADRWLENIEEQGYRLPIKQAEDERGGYPWGSNS
FILNQMIVMGYAYDFTGDSKYLDGMFDGISYLLGRNAMDQSYVTGYGERPLQNPHDRFWTPQ
TSKRFPAPPPGIISGGPNSRFEDPTINAAVKKDTPPQKCFIDHTDSWSTNEITVNWNAPFAW
VTAYLDEQYTDSETDKVTIDSPVAGERFEAGKDINISATVKSKTPVSKVEFYNGDTLISSDT
TAPYTAKITGAAVGAYNLKAVAVLSDGRRIESPVTPVLVKVIVKPTVKLTAPKSNVVAYGNE
FLKITATASDSDGKISRVDFLVDGEVIGSDREAPYEYEWKAVEGNHEISVIAYDDDDAASTP
DSVKIFVKQARDVKVQYLCENTQTSTQEIKGKFNIVNTGNRDYSLKDIVLRYYFTKEHNSQL
QFICYYTPIGSGNLIPSFGGSGDEHYLQLEFKDVKLPAGGQTGEIQFVIRYADNSFHDQSND
YSFDPTIKAFQDYGKVTLYKNGELVWGTPPGGTEPEEPEEPAIVYGCNDDGKVNSTDVAVM
KRYLKKENVNINLDNADVNADGKVNSTDFSILKRYVMKNIEELPYR

Figure 3

SEQ ID NO:3

```
GGTTCGTTTAACTATGGGGAAGCTTTACAAAAAGCTATCATGTTTTACGAATTTCAAATGTCTGGTAAACTTCCGAATTGGGTA
CGCAACAACTGGCGTGGCGACTCAGCATTAAAGGATGGTCAAGACAATGGGCTTGATTTGACAGGTGGTTGGTTTGACGCAGGT
GATCACGTCAAGTTTAACCTTCCAATGTCATACACTGGTACAATGTTGTCATGGGCAGTGTATGAGTACAAAGATGCATTTGTC
AAGAGTGGTCAATTGGAACATATCTTAAATCAAATCGAATGGGTTAATGACTATTTTGTAAAATGTCATCCAAGCAAATATGTA
TACTATTACCAGGTTGGGGATGGAAGTAAAGATCATGCATGGTGGGGACCTGCTGAGGTTATGCAAATGGAGAGACCTTCATTT
AAGGTCACCCAAAGCAGTCCTGGATCTACACAGTAGTAGCAGAGACGCAGCTTCCTTAGCAGCAGCTTCAATTGTTTTGAAAGAC
AGAAATCCCACTAAAGCAGCAACATATCTGCAACATGCAAAAGAATTATATGAGTTTGCAGAAGTAACAAAAAGCGATGCAGGT
TACACTGCTGCAAATGGATATTACAATTCATGGAGCGGTTTCTATGATGAGCTTTCTTGGGCAGCAGTTTGGTTGTATTTGGCA
ACAAATGATTCAACATATCTCACAAAAGCTGAGTCATATGTCCAAAATTGGCCCAAAATTTCTGGCAGTAACACAATTGACTAC
AAGTGGGCTCATTGCTGGGATGATGTTCACAATGGAGCGGCATTATTGTTAGCAAAAATTACCGGTAAGGATATTTATAAACAA
ATTATTGAAAGTCACTTAGATTACTGGACTACAGGATACAATGGCGAAAGGATTAAGTATACACCAAAAGGATTAGCATGGCTT
GATCAATGGGGTTCGTTGAGATATGCAACAACTACAGCATTTTTGGCATTTGTTTATAGCGATTGGGTTGGCTGTCCAAGCACA
AAAAAAGAAATATATAGAAAATTTGGAGAAAGCCAGATTGATTATGCGTTAGGCTCAGCTGGAAGAAGCTTTGTTGTTGGATTT
GGTACAAATCCACCAAAGAGACCGCATCACAGAACTGCTCATAGCTCATGGGCAGACAGTCAGAGTATACCTTCATATCACAGA
CATACATTATATGGAGCGCTTGTTGGTGGTCCAGGCTCTGATGATAGCTACACAGATGATATAAGTAACTATGTGAACAATGAG
GTTGCATGTGATTATAATGCAGGGTTTGTGGGTGCATTAGCAAAGATGTATCAATTGTACGGTGGGAATCCAATACCAGATTTC
AAAGCTATTGAAACTCCAACAAACGACGAATTCTTTGTTGAAGCTGGTATAAATGCATCCGGAACTAACTTTATTGAAATTAAA
GCGATAGTTAATAACCAAAGTGGTTGGCCTGCCAGAGCAACAGATAAGCTTAAATTTAGATATTTTGTTGACCTGAGTGAATTA
ATTAAAGCAGGATATTCACCAAATCAATTAACCTTGAGCACCAATTATAATCAAGGTGCAAAAGTAAGTGGACCTTATGTATGG
GATGCAAGCAAAAATATATACTACATTTTAGTAGACTTTACTGGCACATTGATTTATCCAGGTGGTCAAGACAAATATAAGAAA
GAAGTCCAATTCAGAATTGCAGCACCACAGAATGTACAGTGGGATAATTCTAACGACTATTCTTTCCAGGATATAAAGGGAGTT
TCAAGTGGTTCAGTTGTTAAAACTAAATATATTCCACTTTATGATGGAGATGTGAAAGTATGGGGTGAAGAACCAGGAACTTCT
GGAGCAACACCGACACCAACAGCAACAGCAACACCAACACCGACAGTAACACCAACACCGACTCCAACACCAACATCA
ACTGCTACACCAACACCGACACCAACACCGACAGTAACACCAACCCCGACTCCGACACCGACTGCTACACCAACAGCAACGCCA
ACACCAACATCGACGCCGAGCAGCACACCTGTAGCAGGTGGACAGATAAAGGTATTGTATGCTAACAAGGAGACAAATAGCACA
ACTAATACGATAAGGCCATGGTTGAAGGTAGTGAACACTGGAAGCAGCAGCATAGATTTGAGCAGGGTAACGATAAGGTACTGG
TACACGGTAGATGGGGACAAGGCACAGAGTGCGATATCAGACTGGGCACAGATAGGAGCAAGCAATGTGACATTCAAGTTTGTG
AAGCTGAGCAGTAGCGTAAGTGGAGCGGACTATTATTTAGAGATAGGATTTAAGAGTGGAGCTGGGCAGTTGCAGGCTGGCAAA
GACACAGGGGAGATACAGATAAGGTTTAACAAGAGTGATTGGAGCAATTACAATCAGGGGAATGACTGGTCATGGATGCAGAGC
ATGACGAATTATGGAGAGAATGTGAAGGTAACAGCGTATATAGATGGTGTATTGGTATGGGGACAGGAGCCGAGTGGAGCGACA
CCAACACCGACAGCGACACCAGCACCGACAGTGACACCGACACCTACACCAACACCAACGTCAACACCAACTGCTACACCAACA
GCAACGCCAACACCAACACCGACGCCGAGCAGCACACCTGTAGCAGGCGGGCAGATAAAGGTATTGTATGCTAACAAGGAGACA
AATAGCACAACAACACGATAAGGCCATGGTTGAAGGTAGTGAACACTGGAAGCAGCAGCATAGATTTGAGCAGGGTAACGATA
AGGTACTGGTACACGGTAGATGGGGACAAGGCACAGAGTGCGATATCAGACTGGGCACAGATAGGAGCAAGCAATGTGACATTC
AAGTTTGTGAAGCTGAGCAGTAGCGTAAGTGGAGCGGACTATTATTTAGAGATAGGATTTAAGAGTGGAGCTGGGCAGTTGCAG
GCTGGTAAAGCACAGGGGAGATACAGATAAGGTTTAACAAGAGTGACTGGAGCAATTACAATCAGGGGAATGACTGGTCATGG
ATGCAGAGCATGACGAATTATGGAGAGAATGTGAAGGTAACAGCGTATATAGATGGTGTATTGGTATGGGGACAGGAGCCGAGT
GGAGCGACACCAACACCGACAGCGACACCAGCACCGACAGTGACACCGACACCTACACCAGCACCAACTCCAACCCCGACACCA
ACACCAACTGCTACACCAACACCGACGCCAACACCAACGACCAACACCAACCCCGACGCCAACACCAACACCGACGCCG
AGCAGCACACCGAGTGTGCTTGGCGAATATGGGCAGAGGTTTATGTGGTTATGGAACAAGATACATGATCCTGCGAACGGGTAT
TTTAACCAGGATGGGATACCATATCATTCGGTAGAGACATTGATATGCGAAGCACCTGATTATGGTCATTTGACCACGAGTGAG
GCATTTTCGTACTATGTATGGTTAGAGGCAGTGTATGGTAAGTTAACGGGTGACTGGAGCAAATTTAAGACAGCATGGGACACA
TTAGAGAAGTATATGATACCATCAGCGGAAGATCAGCCGATGAGGTCATATGATCCTAACAAGCCAGCGACATACCAGGGGAG
TGGGAGACACCGGACAAGTATCCATCGCCGTTGGAGTTTAATGTACCTGTTGGCAAAGACCCGTTGCATAATGAACTTGTGAGC
ACATATGGTAGCACATTAATGTATGGTATGCACTGTTGATGGCACTAGACAACTGGTATGGATATGGCAAGAGACGGGGACGGA
GTAAGTCGGGCATCATTTATCAACACGTTCCAGAGAGGGCCTGAGGAGTCTGTATGGGAGACGGTGCCGCATCCGAGCTGGGAG
GAATTCAAGTGGGCCGGACCGAATGGATTTTTAGATTTGTTTATTAAGGATCAGAACTATTCGAAGCAGTGGAGATATACGGAT
GCACCAGATGCTGATGCGAGAGCTATTCAGGCTACTTATTGGGCGAAAGTATGGGCGAAGGAGCAAGGTAAGTTTAATGAGATA
AGCAGCTATGTAGCGAAGGCAGCGAAGATGGGAGACTATTTAAGGTATGCGATGTTTGACAAGTATTTCAAGCCATTAGGATGT
CAGGATAAGAATCTGCTGGAGGAACGGGGTATGACGAGTAGAAGTGACCAGTATACGGTGAGCATTG
GATGGAGCATGGTCATGGAAGATAGGGAGCAGCCATGTGCACTTTGGATATCAGAATCCGATGCGGCATGGGCATTAGCGAAT
GATAGTGATATGAAGCCGAAGTCGCCGAATGGAGCGAGTGACTGGGCAAAGAGTTTGAAGAGGCAGATAGAATTTTACAGGTGG
TTACAGTCAGCGGAGGGAGCGATAGCAGGAGGCGCGACAAATTCATGGAATGGCAGATATGAGAAGTATCCAGCAGGGACAGCA
ACATTTTATGGAATGGCATATGAACCGAATCCGGTATATCATGATCCTGGGAGCAACACATGGTTTGGATTCCAGGCATGGTCG
ATGCAGAGGGTAGCGGAGTATTACTATGTGACAGGAGATAAGGACGCAGGAGCACTGCTTGAGAAGTGGGTAAGCTGGGTTAAG
AGTGTAGTGAAGTTGAATAGTGATGCGTTTGCAGATGCATCGCTTGGGAGAGCGCAACCTGATTACATGATGAACGGG
GCGTATACAGGGAATAGCAACTTACATGTTAAGGTAGTGGACTATGGTACTGACTTAGGAATAACAGCGTCATTGGCGAATGCG
TTGTTGTACTATAGTGCAGGGACGAAGAAGTATGGGGTATTTGATGAGGGAGCGAAGAATTTAGCGAAGGAATTGCTGGACAGG
ATGTGGAAGTTGTACAGGGATGAGAAGGGATTGTCAGCGCCAGAGAAGAGAGCGGACTACAAGAGGTTCTTTGAGCAAGAGGTA
TATATACCGGCAGGATGGATAGGGAAGATGCCGAATGGAGATGTAATAAAGAGTGGAGTTAAGTTTATAGACATAAGGAGCAAG
TATAAACAAGATCCTGATTGGCCGAAGTTAGAGGCGGCATACAAGTCAGGGCAGGCACCTGAGTTCAGATATCACAGGTTCTGG
GCACAGTGCGACATAGCAATAGCTAATGCAACATATGAAATACTGTTTGGCAATCAA
```

Figure 4

SEQ ID NO:4

```
GSFNYGEALQKAIMFYEFQMSGKLPNWVRNNWRGDSALKDGQDNGLDLTGGWFDAGDHV
KFNLPMSYTGTMLSWAVYEYKDAFVKSGQLEHILNQIEWVNDYFVKCHPSKYVYYYQVGD
GSKDHAWWGPAEVMQMERPSFKVTQSSPGSTVVAETAASLAAASIVLKDRNPTKAATYLQ
HAKELYEFAEVTKSDAGYTAANGYYNSWSGFYDELSWAAVWLYLATNDSTYLTKAESYVQ
NWPKISGSNTIDYKWAHCWDDVHNGAALLLAKITGKDIYKQIIESHLDYWTTGYNGERIK
YTPKGLAWLDQWGSLRYATTTAFLAFVYSDWVGCPSTKKEIYRKFGESQIDYALGSAGRS
FVVGFGTNPPKRPHHRTAHSSWADSQSIPSYHRHTLYGALVGGPGSDDSYTDDISNYVNN
EVACDYNAGFVGALAKMYQLYGGNPIPDFKAIETPTNDEFFVEAGINASGTNFIEIKAIV
NNQSGWPARATDKLKFRYFVDLSELIKAGYSPNQLTLSTNYNQGAKVSGPYVWDASKNIY
YILVDFTGTLIYPGGQDKYKKEVQFRIAAPQNVQWDNSNDYSFQDIKGVSSGSVVKTKYI
PLYDGDVKVWGEEPGTSGATPTPTATATPTPTPVTPTPTPTSTATPTPTPTPTVTPT
PTPTPTATPTATPTPTSTPSSTPVAGGQIKVLYANKETNSTTNTIRPWLKVVNTGSSSID
LSRVTIRYWYTVDGDKAQSAISDWAQIGASNVTFKFVKLSSSVSGADYYLEIGFKSGAGQ
LQAGKDTGEIQIRFNKSDWSNYNQGNDWSWMQSMTNYGENVKVTAYIDGVLVWGQEPSGA
TPTPTATPAPTVTPTPTPTPTSTPTATPTATPTPTPTPSSTPVAGGQIKVLYANKETNST
TNTIRPWLKVVNTGSSSIDLSRVTIRYWYTVDGDKAQSAISDWAQIGASNVTFKFVKLSS
SVSGADYYLEIGFKSGAGQLQAGKDTGEIQIRFNKSDWSNYNQGNDWSWMQSMTNYGENV
KVTAYIDGVLVWGQEPSGATPTPTATPAPTVTPTPTPAPTPTPTPTATPTPTPTPTPT
ATPTVTATPTPTPSSTPSVLGEYGQRFMWLWNKIHDPANGYFNQDGIPYHSVETLICEAP
DYGHLTTSEAFSYYVWLEAVYGKLTGDWSKFKTAWDTLEKYMIPSAEDQPMRSYDPNKPA
TYAGEWETPDKYPSPLEFNVPVGKDPLHNELVSTYGSTLMYGMHWLMDVDNWYGYGKRGD
GVSRASFINTFQRGPEESVWETVPHPSWEEFKWGGPNGFLDLFIKDQNYSKQWRYTDAPD
ADARAIQATYWAKVWAKEQGKFNEISSYVAKAAKMGDYLRYAMFDKYFKPLGCQDKNAAG
GTGYDSAHYLLSWYYAWGGALDGAWSWKIGSSHVHFGYQNPMAAWALANDSDMKPKSPNG
ASDWAKSLKRQIEFYRWLQSAEGAIAGGATNSWNGRYEKYPAGTATFYGMAYEPNPVYHD
PGSNTWFGFQAWSMQRVAEYYYVTGDKDAGALLEKWVSWVKSVVKLNSDGTFAIPSTLDW
SGQPDTWNGAYTGNSNLHVKVVDYGTDLGITASLANALLYYSAGTKKYGVFDEGAKNLAK
ELLDRMWKLYRDEKGLSAPEKRADYKRFFEQEVYIPAGWIGKMPNGDVIKSGVKFIDIRS
KYKQDPDWPKLEAAYKSGQAPEFRYHRFWAQCDIAIANATYEILFGNQ
```

SEQ ID NO:5

```
TTAGAAGATAATTCTTCGACTTTGCCGCCGTATAAAAACGACCTTTTGTATGAGAGGACTTTTGATGAGGGACTT
TGTTATCCATGGCATACCTGTGAAGACAGCGGAGGAAAATGCTCCTTTGATGTGGTCGATGTTCCGGGCAGCCC
GGTAATAAAGCATTTGCCGTTACTGTTCTTGACAAAGGGCAAACAGATGGAGCGTTCAGATGAGACACCGTGGT
CTTACTCTTGAACAGGGACATACATATAGAGTACGGCTTAAGATTTGGGCAGATGCGTCCTGTAAAGTTTATATA
AAAATAGGACAAATGGGCGAGCCCTATGCTGAATATTGGAACAACAAGTGGAGTCCATACACACTGACAGCAGGT
AAGGTATTGGAAATTGACGAGACGTTTGTTATGGACAAGCCAACTGACGACACATGCGAATTTACATTCCATTTA
GGTGGCGAATTGGCAGCAACTCCTCCATATACAGTTTATCTTGATGATGTATCCCTTTATGACCCAGAATATACG
AAGCCTGTTGAATATATACTTCCGCAGCCTGATGTACGTGTGAACCAGGTTGGCTACCTGCCGGAGGGCAAGAAA
GTTGCCACTGTGGTATGCAATTCAACTCAGCCGGTAAAATGGCAGCTTAAGAATGCTGCAGGCGTTGTAGTTTTG
GAAGGTTATACCGAACCAAAGGGTCTTGACAAAGACTCGCAGGATTATGTACATTGGCTTGATTTTCCGATTTT
GCAACCGAAGGAATTGGTTACTATTTTGAACTTCCGACTGTAAACAGTCCTACAAACTACAGTCATCCATTTGAC
ATTCGCAAAGACATCTATACTCAGATGAAATATGATGCATTGGCATTCTTCTATCACAAGAGAAGCGGTATTCCT
ATTGAAATGCCGTATGCAGGAGGAGAACAGTGGACCAGACCTGCAGGACATATCGGAATTGAGCCGAACAAGGGA
GATACAAATGTTCCTACATGGCCTCAGGATGATGAGTATGCAGGAATACCTCAGAAGAATTATACAAAGGATGTA
ACCGGTGGATGGTATGATGCCGGTGACCACGGTAAATATGTTGTAAACGGCGGTATAGCCGTCTGGACATTAATG
AACATGTATGAGAGGGCAAAAATTAGAGGTCTTGACAACTGGGGACCATACAGGGACGGCGGAATGAACATACCG
GAGCAGAATAACGGTTATCCGGACATTCTTGATGAAGCAAGATGGGAAATTGAGTTCTTTAAGAAAATGCAGGTA
ACTGAAAAAGAGGATCCTTCCATAGCCGGAATGGTACACCACAAAATTCACGACTTCAGATGGACTGCTTTGGGT
ATGTTGCCTCACGAAGATCCCCAGCCACGTTACTTAAGGCCGGTAAGTACGGCTGCGACTTTGAACTTTGCGGCA
ACTTTGGCACAAAGTGCACGTCTTTGGAAAGATTATGATCCGACTTTTGCTGCTGACTGTTTGGAAAAGGCTGAA
ATAGCATGGCAGGCGGCATTAAAGCATCCTGATATTTATGCTGAGTATACTCCCGGTAGCGGTGGTCCCGGAGGC
GGACCATACAATGACGACTATGTCGGAGACGAATTCTACTGGGCAGCCTGCGAACTTTATGTAACAACAGGAAAA
GACGAATATAAGAATTACCTGATGAATTCACCTCACTATCTTGAAATGCCTGCAAAGATGGGTGAAAACGGTGGA
GCAAACGGAGAAGACAACGGATTGTGGGGATGCTTCACCTGGGGAACTACTCAAGGATTGGGAACCATTACTCTT
GCATTGGTTGAAAACGGATTGCCTGCTACAGACATTCAAAAGGCAAGAAACAATATAGCTAAAGCTGCTGACAGA
TGGCTTGAGAATATTGAAGAGCAAGGTTACAGACTGCCGATCAAACAGGCGGAGGATGAGAGAGGCGGTTATCCA
TGGGGTTCAAACTCCTTCATTTTGAACCAGATGATAGTTATGGGATATGCCTATGACTTTACAGGTGACTCCAAA
TATCTCGATGGAATGTTTGACGGCATAAGCTACCTGTTGGGAAGAAACGCAATGGATCAGTCCTATGTAACAGGG
TATGGTGAGCGTCCGCTTCAGAATCCTCAGCAGGTTCTGACGCCGCAGACAAGTAAGAGATTCCCTGCTCCA
CCTCCGGGTATAATTTCCGGCGGTCCGAACTCCCGTTTCGAGGACCCGACAATAAATGCGGCCGTTAAGAAGGAT
ACACCGCCACAGAAATGTTTTATCGACCATACAGACTCATGGTCAACCAACGAGATAACTGTTAACTGGAATGCT
CCGTTTGCATGGGTTACAGCTTATCTTGACGAGCAGTACACAGACAGTGAAACCGATACACCAACACCGACAGCG
ACACCAGCACCGACAGTGACACCGACACCTACACCAGCACCAACTCCAACCCCGACACCAACACCAACTGCTACA
CCAACACCAACGCCAACACCAACCCCAACCGCGACACCAACAGTAACAGCAACACCAACACCGACGCCGAGCAGC
ACACCGGTAAAAGTACAGTATTTGTGCGAAAATACGCAAACATCCACTCAGGAAATCAAGGGTAAATTCAATATA
GTTAACACAGGAAACAGAGATTATTCGCTGAAAGATATAGTATTAAGATACTACTTTACCAAGGAGCACAATTCA
CAGCTTCAGTTTATCTGCTATTATACACCCATAGGCTCCGGAAATCTCATTCCGTCCTTTGGCGGCTCGGGTGAC
GAGCATTATCTGCAGCTGGAATTCAAAGATGTCAAGCTGCCTGCCGGCGGTCAGACTGGGGAAATACAGTTTGTT
ATAAGATATGCAGATAACTCCTTCCATGATCAGTCGAACGACTATTCGTTCGATCCAACTATAAAAGCGTTCCAG
GATTATGGCAAGGTTACCCTGTATAAGAATGGAGAACTTGTTTGGGGAACGCCGCCGGGCGGTACAGAACCTGAA
GAACCGGAAGAGCCTGCGATAGTTTACGGCGACTGTAATGATGACGGCAAAGTAAATTCAACAGACGTCGCAGTA
ATGAAGAGATATTTAAAGAAAGAAAATGTTAATATTAATCTTGACAATGCAGATGTGAATGCGGACGGCAAAGTT
AACTCAACAGACTTCTCAATACTTAAGAGATATGTTATGAAGAACATAGAAGAATTGCCATATCGA
```

Figure 5

B.
SEQ ID NO:6

LEDNSSTLPPYKNDLLYERTFDEGLCYPWHTCEDSGGKCSFDVVDVPGQPGNKAFAVT
VLDKGQNRWSVQMRHRGLTLEQGHTYRVRLKIWADASCKVYIKIGQMGEPYAEYWNNKWS
PYTLTAGKVLEIDETFVMDKPTDDTCEFTFHLGGELAATPPYTVYLDDVSLYDPEYTKPV
EYILPQPDVRVNQVGYLPEGKKVATVVCNSTQPVKWQLKNAAGVVVLEGYTEPKGLDKDS
QDYVHWLDFSDFATEGIGYYFELPTVNSPTNYSHPFDIRKDIYTQMKYDALAFFYHKRSG
IPIEMPYAGGEQWTRPAGHIGIEPNKGDTNVPTWPQDDEYAGIPQKNYTKDVTGGWYDAG
DHGKYVVNGGIAVWTLMNMYERAKIRGLDNWGPYRDGGMNIPEQNNGYPDILDEARWEIE
FFKKMQVTEKEDPSIAGMVHHKIHDFRWTALGMLPHEDPQPRYLRPVSTAATLNFAATLA
QSARLWKDYDPTFAADCLEKAEIAWQAALKHPDIYAEYTPGSGGPGGGPYNDDYVGDEFY
WAACELYVTTGKDEYKNYLMNSPHYLEMPAKMGENGGANGEDNGLWGCFTWGTTQGLGTI
TLALVENGLPATDIQKARNNIAKAADRWLENIEEQGYRLPIKQAEDERGGYPWGSNSFIL
NQMIVMGYAYDFTGDSKYLDGMFDGISYLLGRNAMDQSYVTGYGERPLQNPHDRFWTPQT
SKRFPAPPPGIISGGPNSRFEDPTINAAVKKDTPPQKCFIDHTDSWSTNEITVNWNAPFA
WVTAYLDEQYTDSETDTPTPTATPAPTVTPTPTPAPTPTPTPTPTATPTPTPTPTPTATP
TVTATPTPTPSSTPVKVQYLCENTQTSTQEIKGKFNIVNTGNRDYSLKDIVLRYYFTKEH
NSQLQFICYYTPIGSGNLIPSFGGSGDEHYLQLEFKDVKLPAGGQTGEIQFVIRYADNSF
HDQSNDYSFDPTIKAFQDYGKVTLYKNGELVWGTPPGGTEPEEPEEPAIVYGDCNDDGKV
NSTDVAVMKRYLKKENVNINLDNADVNADGKVNSTDFSILKRYVMKNIEELPYR

C.
SEQ ID NO:7

ACACCAACACCGACAGCGACACCAGCACCGACAGTGACACCGACACCTACACCAGCACCAAC
TCCAACCCCGACACCAACACCAACTGCTACACCAACACCAACGCCAACACCAACCCCAACCG
CGACACCAACAGTAACAGCAACACCAACACCGACGCCGAGCAGCACACCG

D.
SEQ ID NO:8

TPTPTATPAPTVTPTPTPAPTPTPTPTPTATPTPTPTPTPTATPTVTATPTPTPSSTP

| Type | Gene and its source | Location | Size (number of residues) | Main compositional feature |
|---|---|---|---|---|
| Linker1 | Orf2P (*C. thermocellum*) | 375-476 | 102 | "PT" and "G" -rich |
| Linker2 | CelA (*Caldicellulosiruptor bescii*) | 1040-1097 | 58 | "PT" -rich |
| Linker3 | CbhA (*C. thermocellum*) | 822-1004 | 183 | No unique feature (generic sequence) |

B.

Orf2P

| SP | Coh1 | Coh2 | Linker1 | Doc2 |
|---|---|---|---|---|

CelA

| SP | GH9 | CBM3 | CBM3 | CBM3 | Linker2 | GH48 |
|---|---|---|---|---|---|---|

CbhA

Linker 3

| SP | CBM4 | Ig | GH9 | X1$_1$ | X1$_2$ | CBM3b | Doc1 |
|---|---|---|---|---|---|---|---|

Figure 8
A.
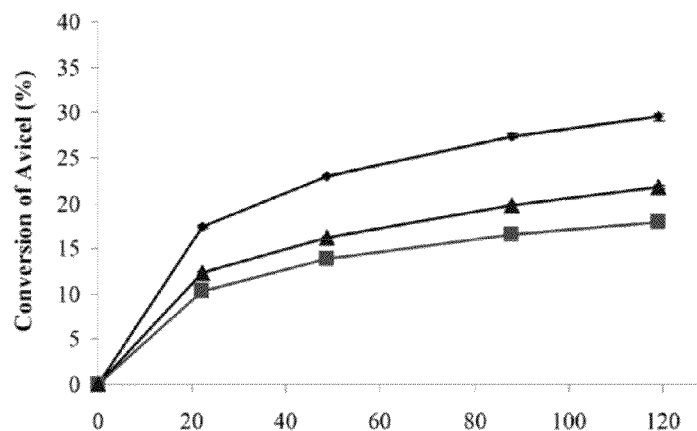
B.
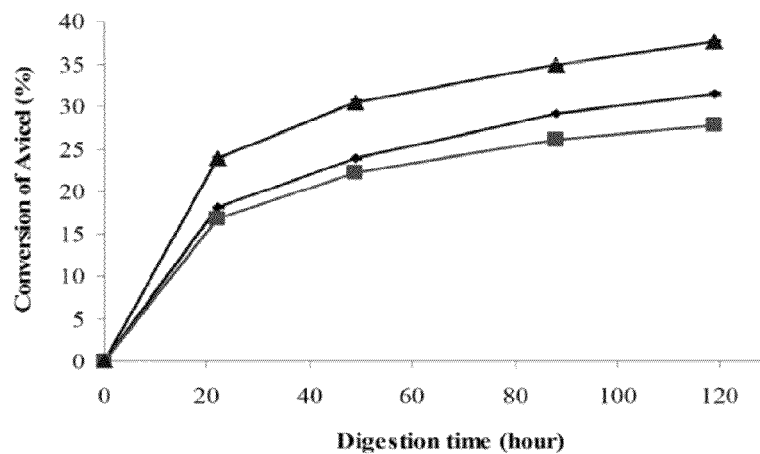
Digestion time (hour)
■ CBM4-Ig-GH9-linker1-CBM3b-Doc (CbhA chimera1)
◆ CBM4-Ig-GH9-linker3-CBM3b-Doc (Wild-type CbhA)
▲ CBM4-Ig-GH9-linker2-CBM3b-Doc (CbhA chimera2)

■ CBM4-Ig-GH9-linker1-Doc + Cohesin2-CBM3a

♦ GH5-Doc + Cohesin2-CBM3a

△ (Mixture of CBM4-Ig-GH9-linker1-Doc and GH5-Doc) + Cohesin2-CBM3a

X   CBM4-Ig-GH9-linker1-GH5-Doc + Cohesin2-CBM3a

SEQUENCE LISTING

<160> NUMBER OF SEQ IDS NOS: 23

<210> SEQ ID NO 1
<211> LENGTH: 3672
<212> TYPE: DNA
<213> ORGANISM: Clostridium thermocellum
<220> FEATURE:
<221> NAME/KEY: CDS
<222> LOCATION: (1)..(3672)

<400> SEQUENCE: 1

```
atg aaa ttt aga agg tca att tgt act gct gtt ttg ttg gcg gtt tta     48
Met Lys Phe Arg Arg Ser Ile Cys Thr Ala Val Leu Leu Ala Val Leu
1               5                   10                  15 ttg aca ctt ctg gta ccg aca tcc gtg ttt gcc tta gaa gat aat tct     96
Leu Thr Leu Leu Val Pro Thr Ser Val Phe Ala Leu Glu Asp Asn Ser
                20                  25                  30 tcg act ttg ccg ccg tat aaa aac gac ctt ttg tat gag agg act ttt    144
Ser Thr Leu Pro Pro Tyr Lys Asn Asp Leu Leu Tyr Glu Arg Thr Phe
            35                  40                  45 gat gag gga ctt tgt tat cca tgg cat acc tgt gaa gac agc gga gga    192
Asp Glu Gly Leu Cys Tyr Pro Trp His Thr Cys Glu Asp Ser Gly Gly
        50                  55                  60 aaa tgc tcc ttt gat gtg gtc gat gtt ccg ggg cag ccc ggt aat aaa    240
Lys Cys Ser Phe Asp Val Val Asp Val Pro Gly Gln Pro Gly Asn Lys
65                  70                  75                  80 gca ttt gcc gtt act gtt ctt gac aaa ggg caa aac aga tgg agc gtt    288
Ala Phe Ala Val Thr Val Leu Asp Lys Gly Gln Asn Arg Trp Ser Val
                85                  90                  95 cag atg aga cac cgt ggt ctt act ctt gaa cag gga cat aca tat aga    336
Gln Met Arg His Arg Gly Leu Thr Leu Glu Gln Gly His Thr Tyr Arg
                100                 105                 110 gta cgg ctt aag att tgg gca gat gcg tcc tgt aaa gtt tat ata aaa    384
Val Arg Leu Lys Ile Trp Ala Asp Ala Ser Cys Lys Val Tyr Ile Lys
            115                 120                 125 ata gga caa atg ggc gag ccc tat gct gaa tat tgg aac aac aag tgg    432
Ile Gly Gln Met Gly Glu Pro Tyr Ala Glu Tyr Trp Asn Asn Lys Trp
        130                 135                 140 agt cca tac aca ctg aca gca ggt aag gta ttg gaa att gac gag acg    480
Ser Pro Tyr Thr Leu Thr Ala Gly Lys Val Leu Glu Ile Asp Glu Thr
145                 150                 155                 160 ttt gtt atg gac aag cca act gac gac aca tgc gaa ttt aca ttc cat    528
Phe Val Met Asp Lys Pro Thr Asp Asp Thr Cys Glu Phe Thr Phe His
                165                 170                 175 tta ggt ggc gaa ttg gca gca act cct cca tat aca gtt tat ctt gat    576
Leu Gly Gly Glu Leu Ala Ala Thr Pro Pro Tyr Thr Val Tyr Leu Asp
                180                 185                 190 gat gta tcc ctt tat gac cca gaa tat acg aag cct gtt gaa tat ata    624
Asp Val Ser Leu Tyr Asp Pro Glu Tyr Thr Lys Pro Val Glu Tyr Ile
            195                 200                 205 ctt ccg cag cct gat gta cgt gtg aac cag gtt ggc tac ctg ccg gag    672
Leu Pro Gln Pro Asp Val Arg Val Asn Gln Val Gly Tyr Leu Pro Glu
        210                 215                 220 ggc aag aaa gtt gcc act gtg gta tgc aat tca act cag ccg gta aaa    720
Gly Lys Lys Val Ala Thr Val Val Cys Asn Ser Thr Gln Pro Val Lys
225                 230                 235                 240 tgg cag ctt aag aat gct gca ggc gtt gta gtt ttg gaa ggt tat acc    768
Trp Gln Leu Lys Asn Ala Ala Gly Val Val Val Leu Glu Gly Tyr Thr
                245                 250                 255 gaa cca aag ggt ctt gac aaa gac tcg cag gat tat gta cat tgg ctt    816
Glu Pro Lys Gly Leu Asp Lys Asp Ser Gln Asp Tyr Val His Trp Leu
```

-continued

```
                260                 265                 270
gat ttt tcc gat ttt gca acc gaa gga att ggt tac tat ttt gaa ctt      864
Asp Phe Ser Asp Phe Ala Thr Glu Gly Ile Gly Tyr Tyr Phe Glu Leu
            275                 280                 285 ccg act gta aac agt cct aca aac tac agt cat cca ttt gac att cgc      912
Pro Thr Val Asn Ser Pro Thr Asn Tyr Ser His Pro Phe Asp Ile Arg
290                 295                 300 aaa gac atc tat act cag atg aaa tat gat gca ttg gca ttc ttc tat      960
Lys Asp Ile Tyr Thr Gln Met Lys Tyr Asp Ala Leu Ala Phe Phe Tyr
305                 310                 315                 320 cac aag aga agc ggt att cct att gaa atg ccg tat gca gga gga gaa     1008
His Lys Arg Ser Gly Ile Pro Ile Glu Met Pro Tyr Ala Gly Gly Glu
                325                 330                 335 cag tgg acc aga cct gca gga cat atc gga att gag ccg aac aag gga     1056
Gln Trp Thr Arg Pro Ala Gly His Ile Gly Ile Glu Pro Asn Lys Gly
            340                 345                 350 gat aca aat gtt cct aca tgg cct cag gat gat gag tat gca gga ata     1104
Asp Thr Asn Val Pro Thr Trp Pro Gln Asp Asp Glu Tyr Ala Gly Ile
        355                 360                 365 cct cag aag aat tat aca aag gat gta acc ggt gga tgg tat gat gcc     1152
Pro Gln Lys Asn Tyr Thr Lys Asp Val Thr Gly Gly Trp Tyr Asp Ala
370                 375                 380 ggt gac cac ggt aaa tat gtt gta aac ggc ggt ata gcc gtc tgg aca     1200
Gly Asp His Gly Lys Tyr Val Val Asn Gly Gly Ile Ala Val Trp Thr
385                 390                 395                 400 tta atg aac atg tat gag agg gca aaa att aga ggt ctt gac aac tgg     1248
Leu Met Asn Met Tyr Glu Arg Ala Lys Ile Arg Gly Leu Asp Asn Trp
                405                 410                 415 gga cca tac agg gac ggc gga atg aac ata ccg gag cag aat aac ggt     1296
Gly Pro Tyr Arg Asp Gly Gly Met Asn Ile Pro Glu Gln Asn Asn Gly
            420                 425                 430 tat ccg gac att ctt gat gaa gca aga tgg gaa att gag ttc ttt aag     1344
Tyr Pro Asp Ile Leu Asp Glu Ala Arg Trp Glu Ile Glu Phe Phe Lys
        435                 440                 445 aaa atg cag gta act gaa aaa gag gat cct tcc ata gcc gga atg gta     1392
Lys Met Gln Val Thr Glu Lys Glu Asp Pro Ser Ile Ala Gly Met Val
450                 455                 460 cac cac aaa att cac gac ttc aga tgg act gct ttg ggt atg ttg cct     1440
His His Lys Ile His Asp Phe Arg Trp Thr Ala Leu Gly Met Leu Pro
465                 470                 475                 480 cac gaa gat ccc cag cca cgt tac tta agg ccg gta agt acg gct gcg     1488
His Glu Asp Pro Gln Pro Arg Tyr Leu Arg Pro Val Ser Thr Ala Ala
                485                 490                 495 act ttg aac ttt gcg gca act ttg gca caa agt gca cgt ctt tgg aaa     1536
Thr Leu Asn Phe Ala Ala Thr Leu Ala Gln Ser Ala Arg Leu Trp Lys
            500                 505                 510 gat tat gat ccg act ttt gct gct gac tgt ttg gaa aag gct gaa ata     1584
Asp Tyr Asp Pro Thr Phe Ala Ala Asp Cys Leu Glu Lys Ala Glu Ile
        515                 520                 525 gca tgg cag gcg gca tta aag cat cct gat att tat gct gag tat act     1632
Ala Trp Gln Ala Ala Leu Lys His Pro Asp Ile Tyr Ala Glu Tyr Thr
530                 535                 540 ccc ggt agc ggt ggt ccc gga ggc gga cca tac aat gac gac tat gtc     1680
Pro Gly Ser Gly Gly Pro Gly Gly Gly Pro Tyr Asn Asp Asp Tyr Val
545                 550                 555                 560 gga gac gaa ttc tac tgg gca gcc tgc gaa ctt tat gta aca aca gga     1728
Gly Asp Glu Phe Tyr Trp Ala Ala Cys Glu Leu Tyr Val Thr Thr Gly
                565                 570                 575 aaa gac gaa tat aag aat tac ctg atg aat tca cct cac tat ctt gaa     1776
```

```
                Lys Asp Glu Tyr Lys Asn Tyr Leu Met Asn Ser Pro His Tyr Leu Glu
                            580                 585                 590 atg cct gca aag atg ggt gaa aac ggt gga gca aac gga gaa gac aac           1824
Met Pro Ala Lys Met Gly Glu Asn Gly Gly Ala Asn Gly Glu Asp Asn
            595                 600                 605 gga ttg tgg gga tgc ttc acc tgg gga act act caa gga ttg gga acc           1872
Gly Leu Trp Gly Cys Phe Thr Trp Gly Thr Thr Gln Gly Leu Gly Thr
610                 615                 620 att act ctt gca ttg gtt gaa aac gga ttg cct gct aca gac att caa           1920
Ile Thr Leu Ala Leu Val Glu Asn Gly Leu Pro Ala Thr Asp Ile Gln
625                 630                 635                 640 aag gca aga aac aat ata gct aaa gct gct gac aga tgg ctt gag aat           1968
Lys Ala Arg Asn Asn Ile Ala Lys Ala Ala Asp Arg Trp Leu Glu Asn
                645                 650                 655 att gaa gag caa ggt tac aga ctg ccg atc aaa cag gcg gag gat gag           2016
Ile Glu Glu Gln Gly Tyr Arg Leu Pro Ile Lys Gln Ala Glu Asp Glu
            660                 665                 670 aga ggc ggt tat cca tgg ggt tca aac tcc ttc att ttg aac cag atg           2064
Arg Gly Gly Tyr Pro Trp Gly Ser Asn Ser Phe Ile Leu Asn Gln Met
        675                 680                 685 ata gtt atg gga tat gcc tat gac ttt aca ggt gac tcc aaa tat ctc           2112
Ile Val Met Gly Tyr Ala Tyr Asp Phe Thr Gly Asp Ser Lys Tyr Leu
    690                 695                 700 gat gga atg ttt gac ggc ata agc tac ctg ttg gga aga aac gca atg           2160
Asp Gly Met Phe Asp Gly Ile Ser Tyr Leu Leu Gly Arg Asn Ala Met
705                 710                 715                 720 gat cag tcc tat gta aca ggg tat ggt gag cgt ccg ctt cag aat cct           2208
Asp Gln Ser Tyr Val Thr Gly Tyr Gly Glu Arg Pro Leu Gln Asn Pro
                725                 730                 735 cat gac agg ttc tgg acg ccg cag aca agt aag aga ttc cct gct cca           2256
His Asp Arg Phe Trp Thr Pro Gln Thr Ser Lys Arg Phe Pro Ala Pro
            740                 745                 750 cct ccg ggt ata att tcc ggc ggt ccg aac tcc cgt ttc gag gac ccg           2304
Pro Pro Gly Ile Ile Ser Gly Gly Pro Asn Ser Arg Phe Glu Asp Pro
        755                 760                 765 aca ata aat gcg gcc gtt aag aag gat aca ccg cca cag aaa tgt ttt           2352
Thr Ile Asn Ala Ala Val Lys Lys Asp Thr Pro Pro Gln Lys Cys Phe
    770                 775                 780 atc gac cat aca gac tca tgg tca acc aac gag ata act gtt aac tgg           2400
Ile Asp His Thr Asp Ser Trp Ser Thr Asn Glu Ile Thr Val Asn Trp
785                 790                 795                 800 aat gct ccg ttt gca tgg gtt aca gct tat ctt gac gag cag tac aca           2448
Asn Ala Pro Phe Ala Trp Val Thr Ala Tyr Leu Asp Glu Gln Tyr Thr
                805                 810                 815 gac agt gaa acc gat aag gta act att gat tcg cct gtt gca gga gaa           2496
Asp Ser Glu Thr Asp Lys Val Thr Ile Asp Ser Pro Val Ala Gly Glu
            820                 825                 830 aga ttt gaa gcc ggt aaa gac att aat ata agc gca act gtt aaa tca           2544
Arg Phe Glu Ala Gly Lys Asp Ile Asn Ile Ser Ala Thr Val Lys Ser
        835                 840                 845 aaa act cct gta agc aaa gta gag ttt tac aat gga gat acg ctt att           2592
Lys Thr Pro Val Ser Lys Val Glu Phe Tyr Asn Gly Asp Thr Leu Ile
    850                 855                 860 tcc agt gac aca act gca cct tac aca gca aag ata aca gga gcc gct           2640
Ser Ser Asp Thr Thr Ala Pro Tyr Thr Ala Lys Ile Thr Gly Ala Ala
865                 870                 875                 880 gtc gga gca tat aac ctt aaa gcg gtt gca gtg ctg tct gac gga aga           2688
Val Gly Ala Tyr Asn Leu Lys Ala Val Ala Val Leu Ser Asp Gly Arg
                885                 890                 895
```

```
aga att gag tca ccg gta act cct gta ctt gtt aag gta att gtg aaa    2736
Arg Ile Glu Ser Pro Val Thr Pro Val Leu Val Lys Val Ile Val Lys
                900                 905                 910 cct act gta aaa ctt act gca ccc aag tca aat gtt gtg gct tat gga    2784
Pro Thr Val Lys Leu Thr Ala Pro Lys Ser Asn Val Val Ala Tyr Gly
            915                 920                 925 aat gag ttc ctg aag att aca gca aca gcc agt gac tct gac ggc aaa    2832
Asn Glu Phe Leu Lys Ile Thr Ala Thr Ala Ser Asp Ser Asp Gly Lys
        930                 935                 940 atc tcc agg gtt gat ttc ctt gtt gac ggt gaa gta atc ggt tca gac    2880
Ile Ser Arg Val Asp Phe Leu Val Asp Gly Glu Val Ile Gly Ser Asp
945                 950                 955                 960 agg gaa gca cct tat gaa tat gag tgg aaa gct gtg gaa ggc aat cac    2928
Arg Glu Ala Pro Tyr Glu Tyr Glu Trp Lys Ala Val Glu Gly Asn His
                965                 970                 975 gaa ata agt gta att gct tat gat gat gac gat gcg gct tca aca cct    2976
Glu Ile Ser Val Ile Ala Tyr Asp Asp Asp Asp Ala Ala Ser Thr Pro
            980                 985                 990 gat tcc gta aaa ata ttt gta aaa cag gca cgg gat gta aaa gta cag   3024
Asp Ser Val Lys Ile Phe Val Lys Gln Ala Arg Asp Val Lys Val Gln
        995                 1000                1005 tat ttg tgc gaa aat acg caa aca tcc act cag gaa atc aag ggt       3069
Tyr Leu Cys Glu Asn Thr Gln Thr Ser Thr Gln Glu Ile Lys Gly
    1010                1015                1020 aaa ttc aat ata gtt aac aca gga aac aga gat tat tcg ctg aaa       3114
Lys Phe Asn Ile Val Asn Thr Gly Asn Arg Asp Tyr Ser Leu Lys
1025                1030                1035 gat ata gta tta aga tac tac ttt acc aag gag cac aat tca cag       3159
Asp Ile Val Leu Arg Tyr Tyr Phe Thr Lys Glu His Asn Ser Gln
    1040                1045                1050 ctt cag ttt atc tgc tat tat aca ccc ata ggc tcc gga aat ctc       3204
Leu Gln Phe Ile Cys Tyr Tyr Thr Pro Ile Gly Ser Gly Asn Leu
1055                1060                1065 att ccg tcc ttt ggc ggc tcg ggt gac gag cat tat ctg cag ctg       3249
Ile Pro Ser Phe Gly Gly Ser Gly Asp Glu His Tyr Leu Gln Leu
    1070                1075                1080 gaa ttc aaa gat gtc aag ctg cct gcc ggc ggt cag act ggg gaa       3294
Glu Phe Lys Asp Val Lys Leu Pro Ala Gly Gly Gln Thr Gly Glu
1085                1090                1095 ata cag ttt gtt ata aga tat gca gat aac tcc ttc cat gat cag       3339
Ile Gln Phe Val Ile Arg Tyr Ala Asp Asn Ser Phe His Asp Gln
    1100                1105                1110 tcg aac gac tat tcg ttc gat cca act ata aaa gcg ttc cag gat       3384
Ser Asn Asp Tyr Ser Phe Asp Pro Thr Ile Lys Ala Phe Gln Asp
1115                1120                1125 tat ggc aag gtt acc ctg tat aag aat gga gaa ctt gtt tgg gga       3429
Tyr Gly Lys Val Thr Leu Tyr Lys Asn Gly Glu Leu Val Trp Gly
    1130                1135                1140 acg ccg ccg ggc ggt aca gaa cct gaa gaa ccg gaa gag cct gcg       3474
Thr Pro Pro Gly Gly Thr Glu Pro Glu Glu Pro Glu Glu Pro Ala
1145                1150                1155 ata gtt tac ggc gac tgt aat gat gac ggc aaa gta aat tca aca       3519
Ile Val Tyr Gly Asp Cys Asn Asp Asp Gly Lys Val Asn Ser Thr
    1160                1165                1170 gac gtc gca gta atg aag aga tat tta aag aaa gaa aat gtt aat       3564
Asp Val Ala Val Met Lys Arg Tyr Leu Lys Lys Glu Asn Val Asn
1175                1180                1185 att aat ctt gac aat gca gat gtg aat gcg gac ggc aaa gtt aac       3609
Ile Asn Leu Asp Asn Ala Asp Val Asn Ala Asp Gly Lys Val Asn
    1190                1195                1200
```

```
tca  aca  gac  ttc  tca  ata  ctt  aag  aga  tat  gtt  atg  aag  aac  ata         3654
Ser  Thr  Asp  Phe  Ser  Ile  Leu  Lys  Arg  Tyr  Val  Met  Lys  Asn  Ile
    1205                1210                1215 gaa  gaa  ttg  cca  tat  cga                                                      3672
Glu  Glu  Leu  Pro  Tyr  Arg
    1220
```

<210> SEQ ID NO 2
<211> LENGTH: 1224
<212> TYPE: PRT
<213> ORGANISM: Clostridium thermocellum

<400> SEQUENCE: 2

```
Met Lys Phe Arg Arg Ser Ile Cys Thr Ala Val Leu Leu Ala Val Leu
 1               5                  10                  15

Leu Thr Leu Leu Val Pro Thr Ser Val Phe Ala Leu Glu Asp Asn Ser
            20                  25                  30

Ser Thr Leu Pro Pro Tyr Lys Asn Asp Leu Leu Tyr Glu Arg Thr Phe
        35                  40                  45

Asp Glu Gly Leu Cys Tyr Pro Trp His Thr Cys Glu Asp Ser Gly Gly
     50                  55                  60

Lys Cys Ser Phe Asp Val Val Asp Val Pro Gly Gln Pro Gly Asn Lys
 65                  70                  75                  80

Ala Phe Ala Val Thr Val Leu Asp Lys Gly Gln Asn Arg Trp Ser Val
                 85                  90                  95

Gln Met Arg His Arg Gly Leu Thr Leu Glu Gln Gly His Thr Tyr Arg
            100                 105                 110

Val Arg Leu Lys Ile Trp Ala Asp Ala Ser Cys Lys Val Tyr Ile Lys
        115                 120                 125

Ile Gly Gln Met Gly Glu Pro Tyr Ala Glu Tyr Trp Asn Asn Lys Trp
    130                 135                 140

Ser Pro Tyr Thr Leu Thr Ala Gly Lys Val Leu Glu Ile Asp Glu Thr
145                 150                 155                 160

Phe Val Met Asp Lys Pro Thr Asp Asp Thr Cys Glu Phe Thr Phe His
                165                 170                 175

Leu Gly Gly Glu Leu Ala Ala Thr Pro Pro Tyr Thr Val Tyr Leu Asp
            180                 185                 190

Asp Val Ser Leu Tyr Asp Pro Glu Tyr Thr Lys Pro Val Glu Tyr Ile
        195                 200                 205

Leu Pro Gln Pro Asp Val Arg Val Asn Gln Val Gly Tyr Leu Pro Glu
    210                 215                 220

Gly Lys Lys Val Ala Thr Val Val Cys Asn Ser Thr Gln Pro Val Lys
225                 230                 235                 240

Trp Gln Leu Lys Asn Ala Ala Gly Val Val Leu Glu Gly Tyr Thr
                245                 250                 255

Glu Pro Lys Gly Leu Asp Lys Asp Ser Gln Asp Tyr Val His Trp Leu
            260                 265                 270

Asp Phe Ser Asp Phe Ala Thr Glu Gly Ile Gly Tyr Tyr Phe Glu Leu
        275                 280                 285

Pro Thr Val Asn Ser Pro Thr Asn Tyr Ser His Pro Phe Asp Ile Arg
    290                 295                 300

Lys Asp Ile Tyr Thr Gln Met Lys Tyr Asp Ala Leu Ala Phe Phe Tyr
305                 310                 315                 320

His Lys Arg Ser Gly Ile Pro Ile Glu Met Pro Tyr Ala Gly Gly Glu
                325                 330                 335
```

-continued

Gln Trp Thr Arg Pro Ala Gly His Ile Gly Ile Glu Pro Asn Lys Gly
            340                 345                 350

Asp Thr Asn Val Pro Thr Trp Pro Gln Asp Asp Glu Tyr Ala Gly Ile
            355                 360                 365

Pro Gln Lys Asn Tyr Thr Lys Asp Val Thr Gly Gly Trp Tyr Asp Ala
    370                 375                 380

Gly Asp His Gly Lys Tyr Val Val Asn Gly Ile Ala Val Trp Thr
385                 390                 395                 400

Leu Met Asn Met Tyr Glu Arg Ala Lys Ile Arg Gly Leu Asp Asn Trp
                405                 410                 415

Gly Pro Tyr Arg Asp Gly Met Asn Ile Pro Glu Gln Asn Asn Gly
            420                 425                 430

Tyr Pro Asp Ile Leu Asp Glu Ala Arg Trp Glu Ile Glu Phe Phe Lys
        435                 440                 445

Lys Met Gln Val Thr Glu Lys Glu Asp Pro Ser Ile Ala Gly Met Val
    450                 455                 460

His His Lys Ile His Asp Phe Arg Trp Thr Ala Leu Gly Met Leu Pro
465                 470                 475                 480

His Glu Asp Pro Gln Pro Arg Tyr Leu Arg Pro Val Ser Thr Ala Ala
                485                 490                 495

Thr Leu Asn Phe Ala Ala Thr Leu Ala Gln Ser Ala Arg Leu Trp Lys
            500                 505                 510

Asp Tyr Asp Pro Thr Phe Ala Ala Asp Cys Leu Glu Lys Ala Glu Ile
        515                 520                 525

Ala Trp Gln Ala Ala Leu Lys His Pro Asp Ile Tyr Ala Glu Tyr Thr
    530                 535                 540

Pro Gly Ser Gly Gly Pro Gly Gly Pro Tyr Asn Asp Asp Tyr Val
545                 550                 555                 560

Gly Asp Glu Phe Tyr Trp Ala Ala Cys Glu Leu Tyr Val Thr Thr Gly
                565                 570                 575

Lys Asp Glu Tyr Lys Asn Tyr Leu Met Asn Ser Pro His Tyr Leu Glu
            580                 585                 590

Met Pro Ala Lys Met Gly Glu Asn Gly Ala Asn Gly Glu Asp Asn
        595                 600                 605

Gly Leu Trp Gly Cys Phe Thr Trp Gly Thr Thr Gln Gly Leu Gly Thr
    610                 615                 620

Ile Thr Leu Ala Leu Val Glu Asn Gly Leu Pro Ala Thr Asp Ile Gln
625                 630                 635                 640

Lys Ala Arg Asn Asn Ile Ala Lys Ala Ala Asp Arg Trp Leu Glu Asn
                645                 650                 655

Ile Glu Glu Gln Gly Tyr Arg Leu Pro Ile Lys Gln Ala Glu Asp Glu
            660                 665                 670

Arg Gly Gly Tyr Pro Trp Gly Ser Asn Ser Phe Ile Leu Asn Gln Met
        675                 680                 685

Ile Val Met Gly Tyr Ala Tyr Asp Phe Thr Gly Asp Ser Lys Tyr Leu
    690                 695                 700

Asp Gly Met Phe Asp Gly Ile Ser Tyr Leu Leu Gly Arg Asn Ala Met
705                 710                 715                 720

Asp Gln Ser Tyr Val Thr Gly Tyr Gly Glu Arg Pro Leu Gln Asn Pro
                725                 730                 735

His Asp Arg Phe Trp Thr Pro Gln Thr Ser Lys Arg Phe Pro Ala Pro
            740                 745                 750

-continued

Pro Pro Gly Ile Ile Ser Gly Gly Pro Asn Ser Arg Phe Glu Asp Pro
            755                 760                 765

Thr Ile Asn Ala Ala Val Lys Lys Asp Thr Pro Pro Gln Lys Cys Phe
770                 775                 780

Ile Asp His Thr Asp Ser Trp Ser Thr Asn Glu Ile Thr Val Asn Trp
785                 790                 795                 800

Asn Ala Pro Phe Ala Trp Val Thr Ala Tyr Leu Asp Glu Gln Tyr Thr
                805                 810                 815

Asp Ser Glu Thr Asp Lys Val Thr Ile Asp Ser Pro Val Ala Gly Glu
            820                 825                 830

Arg Phe Glu Ala Gly Lys Asp Ile Asn Ile Ser Ala Thr Val Lys Ser
            835                 840                 845

Lys Thr Pro Val Ser Lys Val Glu Phe Tyr Asn Gly Asp Thr Leu Ile
850                 855                 860

Ser Ser Asp Thr Thr Ala Pro Tyr Thr Ala Lys Ile Thr Gly Ala Ala
865                 870                 875                 880

Val Gly Ala Tyr Asn Leu Lys Ala Val Ala Val Leu Ser Asp Gly Arg
                885                 890                 895

Arg Ile Glu Ser Pro Val Thr Pro Val Leu Val Lys Val Ile Val Lys
            900                 905                 910

Pro Thr Val Lys Leu Thr Ala Pro Lys Ser Asn Val Val Ala Tyr Gly
            915                 920                 925

Asn Glu Phe Leu Lys Ile Thr Ala Thr Ala Ser Asp Ser Asp Gly Lys
930                 935                 940

Ile Ser Arg Val Asp Phe Leu Val Asp Gly Glu Val Ile Gly Ser Asp
945                 950                 955                 960

Arg Glu Ala Pro Tyr Glu Tyr Glu Trp Lys Ala Val Glu Gly Asn His
                965                 970                 975

Glu Ile Ser Val Ile Ala Tyr Asp Asp Asp Ala Ala Ser Thr Pro
            980                 985                 990

Asp Ser Val Lys Ile Phe Val Lys Gln Ala Arg Asp Val Lys Val Gln
            995                 1000                 1005

Tyr Leu Cys Glu Asn Thr Gln Thr Ser Thr Gln Glu Ile Lys Gly
   1010                 1015                 1020

Lys Phe Asn Ile Val Asn Thr Gly Asn Arg Asp Tyr Ser Leu Lys
   1025                 1030                 1035

Asp Ile Val Leu Arg Tyr Tyr Phe Thr Lys Glu His Asn Ser Gln
   1040                 1045                 1050

Leu Gln Phe Ile Cys Tyr Tyr Thr Pro Ile Gly Ser Gly Asn Leu
   1055                 1060                 1065

Ile Pro Ser Phe Gly Gly Ser Gly Asp Glu His Tyr Leu Gln Leu
   1070                 1075                 1080

Glu Phe Lys Asp Val Lys Leu Pro Ala Gly Gly Gln Thr Gly Glu
   1085                 1090                 1095

Ile Gln Phe Val Ile Arg Tyr Ala Asp Asn Ser Phe His Asp Gln
   1100                 1105                 1110

Ser Asn Asp Tyr Ser Phe Asp Pro Thr Ile Lys Ala Phe Gln Asp
   1115                 1120                 1125

Tyr Gly Lys Val Thr Leu Tyr Lys Asn Gly Glu Leu Val Trp Gly
   1130                 1135                 1140

Thr Pro Pro Gly Gly Thr Glu Pro Glu Glu Pro Glu Glu Pro Ala
   1145                 1150                 1155

Ile Val Tyr Gly Asp Cys Asn Asp Asp Gly Lys Val Asn Ser Thr

```
                1160                1165                1170

Asp Val Ala Val Met Lys Arg Tyr Leu Lys Lys Glu Asn Val Asn
    1175                1180                1185

Ile Asn Leu Asp Asn Ala Asp Val Asn Ala Asp Gly Lys Val Asn
    1190                1195                1200

Ser Thr Asp Phe Ser Ile Leu Lys Arg Tyr Val Met Lys Asn Ile
    1205                1210                1215

Glu Glu Leu Pro Tyr Arg
    1220

<210> SEQ ID NO 3
<211> LENGTH: 5181
<212> TYPE: DNA
<213> ORGANISM: Caldicellulosiruptor bescii
<220> FEATURE:
<221> NAME/KEY: CDS
<222> LOCATION: (1)..(5181)

<400> SEQUENCE: 3 ggt tcg ttt aac tat ggg gaa gct tta caa aaa gct atc atg ttt tac    48
Gly Ser Phe Asn Tyr Gly Glu Ala Leu Gln Lys Ala Ile Met Phe Tyr
 1               5                  10                  15 gaa ttt caa atg tct ggt aaa ctt ccg aat tgg gta cgc aac aac tgg    96
Glu Phe Gln Met Ser Gly Lys Leu Pro Asn Trp Val Arg Asn Asn Trp
             20                  25                  30 cgt ggc gac tca gca tta aag gat ggt caa gac aat ggg ctt gat ttg   144
Arg Gly Asp Ser Ala Leu Lys Asp Gly Gln Asp Asn Gly Leu Asp Leu
         35                  40                  45 aca ggt ggt tgg ttt gac gca ggt gat cac gtc aag ttt aac ctt cca   192
Thr Gly Gly Trp Phe Asp Ala Gly Asp His Val Lys Phe Asn Leu Pro
     50                  55                  60 atg tca tac act ggt aca atg ttg tca tgg gca gtg tat gag tac aaa   240
Met Ser Tyr Thr Gly Thr Met Leu Ser Trp Ala Val Tyr Glu Tyr Lys
 65                  70                  75                  80 gat gca ttt gtc aag agt ggt caa ttg gaa cat atc tta aat caa atc   288
Asp Ala Phe Val Lys Ser Gly Gln Leu Glu His Ile Leu Asn Gln Ile
                 85                  90                  95 gaa tgg gtt aat gac tat ttt gta aaa tgt cat cca agc aaa tat gta   336
Glu Trp Val Asn Asp Tyr Phe Val Lys Cys His Pro Ser Lys Tyr Val
            100                 105                 110 tac tat tac cag gtt ggg gat gga agt aaa gat cat gca tgg tgg gga   384
Tyr Tyr Tyr Gln Val Gly Asp Gly Ser Lys Asp His Ala Trp Trp Gly
        115                 120                 125 cct gct gag gtt atg caa atg gag aga cct tca ttt aag gtc acc caa   432
Pro Ala Glu Val Met Gln Met Glu Arg Pro Ser Phe Lys Val Thr Gln
    130                 135                 140 agc agt cct gga tct aca gta gta gca gag aca gca gct tcc tta gca   480
Ser Ser Pro Gly Ser Thr Val Val Ala Glu Thr Ala Ala Ser Leu Ala
145                 150                 155                 160 gca gct tca att gtt ttg aaa gac aga aat ccc act aaa gca gca aca   528
Ala Ala Ser Ile Val Leu Lys Asp Arg Asn Pro Thr Lys Ala Ala Thr
                165                 170                 175 tat ctg caa cat gca aaa gaa tta tat gag ttt gca gaa gta aca aaa   576
Tyr Leu Gln His Ala Lys Glu Leu Tyr Glu Phe Ala Glu Val Thr Lys
            180                 185                 190 agc gat gca ggt tac act gct gca aat gga tat tac aat tca tgg agc   624
Ser Asp Ala Gly Tyr Thr Ala Ala Asn Gly Tyr Tyr Asn Ser Trp Ser
        195                 200                 205 ggt ttc tat gat gag ctt tct tgg gca gca gtt tgg ttg tat ttg gca   672
Gly Phe Tyr Asp Glu Leu Ser Trp Ala Ala Val Trp Leu Tyr Leu Ala
```

```
                    210                 215                 220
aca aat gat tca aca tat ctc aca aaa gct gag tca tat gtc caa aat       720
Thr Asn Asp Ser Thr Tyr Leu Thr Lys Ala Glu Ser Tyr Val Gln Asn
225                 230                 235                 240 tgg ccc aaa att tct ggc agt aac aca att gac tac aag tgg gct cat       768
Trp Pro Lys Ile Ser Gly Ser Asn Thr Ile Asp Tyr Lys Trp Ala His
                245                 250                 255 tgc tgg gat gat gtt cac aat gga gcg gca tta ttg tta gca aaa att       816
Cys Trp Asp Asp Val His Asn Gly Ala Ala Leu Leu Leu Ala Lys Ile
                260                 265                 270 acc ggt aag gat att tat aaa caa att att gaa agt cac tta gat tac       864
Thr Gly Lys Asp Ile Tyr Lys Gln Ile Ile Glu Ser His Leu Asp Tyr
            275                 280                 285 tgg act aca gga tac aat ggc gaa agg att aag tat aca cca aaa gga       912
Trp Thr Thr Gly Tyr Asn Gly Glu Arg Ile Lys Tyr Thr Pro Lys Gly
        290                 295                 300 tta gca tgg ctt gat caa tgg ggt tcg ttg aga tat gca aca act aca       960
Leu Ala Trp Leu Asp Gln Trp Gly Ser Leu Arg Tyr Ala Thr Thr Thr
305                 310                 315                 320 gca ttt ttg gca ttt gtt tat agc gat tgg gtt ggc tgt cca agc aca      1008
Ala Phe Leu Ala Phe Val Tyr Ser Asp Trp Val Gly Cys Pro Ser Thr
                325                 330                 335 aaa aaa gaa ata tat aga aaa ttt gga gaa agc cag att gat tat gcg      1056
Lys Lys Glu Ile Tyr Arg Lys Phe Gly Glu Ser Gln Ile Asp Tyr Ala
                340                 345                 350 tta ggc tca gct gga aga agc ttt gtt gtt gga ttt ggt aca aat cca      1104
Leu Gly Ser Ala Gly Arg Ser Phe Val Val Gly Phe Gly Thr Asn Pro
            355                 360                 365 cca aag aga ccg cat cac aga act gct cat agc tca tgg gca gac agt      1152
Pro Lys Arg Pro His His Arg Thr Ala His Ser Ser Trp Ala Asp Ser
        370                 375                 380 cag agt ata cct tca tat cac aga cat aca tta tat gga gcg ctt gtt      1200
Gln Ser Ile Pro Ser Tyr His Arg His Thr Leu Tyr Gly Ala Leu Val
385                 390                 395                 400 ggt ggt cca ggc tct gat gat agc tac aca gat gat ata agt aac tat      1248
Gly Gly Pro Gly Ser Asp Asp Ser Tyr Thr Asp Asp Ile Ser Asn Tyr
                405                 410                 415 gtg aac aat gag gtt gca tgt gat tat aat gca ggg ttt gtg ggt gca      1296
Val Asn Asn Glu Val Ala Cys Asp Tyr Asn Ala Gly Phe Val Gly Ala
                420                 425                 430 tta gca aag atg tat caa ttg tac ggt ggg aat cca ata cca gat ttc      1344
Leu Ala Lys Met Tyr Gln Leu Tyr Gly Gly Asn Pro Ile Pro Asp Phe
            435                 440                 445 aaa gct att gaa act cca aca aac gac gaa ttc ttt gtt gaa gct ggt      1392
Lys Ala Ile Glu Thr Pro Thr Asn Asp Glu Phe Phe Val Glu Ala Gly
        450                 455                 460 ata aat gca tcc gga act aac ttt att gaa att aaa gcg ata gtt aat      1440
Ile Asn Ala Ser Gly Thr Asn Phe Ile Glu Ile Lys Ala Ile Val Asn
465                 470                 475                 480 aac caa agt ggt tgg cct gcc aga gca aca gat aag ctt aaa ttt aga      1488
Asn Gln Ser Gly Trp Pro Ala Arg Ala Thr Asp Lys Leu Lys Phe Arg
                485                 490                 495 tat ttt gtt gac ctg agt gaa tta att aaa gca gga tat tca cca aat      1536
Tyr Phe Val Asp Leu Ser Glu Leu Ile Lys Ala Gly Tyr Ser Pro Asn
                500                 505                 510 caa tta acc ttg agc acc aat tat aat caa ggt gca aaa gta agt gga      1584
Gln Leu Thr Leu Ser Thr Asn Tyr Asn Gln Gly Ala Lys Val Ser Gly
            515                 520                 525 cct tat gta tgg gat gca agc aaa aat ata tac tac att tta gta gac      1632
```

-continued

```
                Pro Tyr Val Trp Asp Ala Ser Lys Asn Ile Tyr Tyr Ile Leu Val Asp
                    530                 535                 540 ttt act ggc aca ttg att tat cca ggt ggt caa gac aaa tat aag aaa            1680
Phe Thr Gly Thr Leu Ile Tyr Pro Gly Gly Gln Asp Lys Tyr Lys Lys
545                 550                 555                 560 gaa gtc caa ttc aga att gca gca cca cag aat gta cag tgg gat aat            1728
Glu Val Gln Phe Arg Ile Ala Ala Pro Gln Asn Val Gln Trp Asp Asn
                565                 570                 575 tct aac gac tat tct ttc cag gat ata aag gga gtt tca agt ggt tca            1776
Ser Asn Asp Tyr Ser Phe Gln Asp Ile Lys Gly Val Ser Ser Gly Ser
            580                 585                 590 gtt gtt aaa act aaa tat att cca ctt tat gat gga gat gtg aaa gta            1824
Val Val Lys Thr Lys Tyr Ile Pro Leu Tyr Asp Gly Asp Val Lys Val
        595                 600                 605 tgg ggt gaa gaa cca gga act tct gga gca aca ccg aca cca aca gca            1872
Trp Gly Glu Glu Pro Gly Thr Ser Gly Ala Thr Pro Thr Pro Thr Ala
    610                 615                 620 aca gca aca cca aca cca acg ccg aca gta aca cca aca ccg act cca            1920
Thr Ala Thr Pro Thr Pro Thr Pro Thr Val Thr Pro Thr Pro Thr Pro
625                 630                 635                 640 aca cca aca tca act gct aca cca aca ccg aca cca acg cca aca gta            1968
Thr Pro Thr Ser Thr Ala Thr Pro Thr Pro Thr Pro Thr Pro Thr Val
                645                 650                 655 aca cca acc ccg act ccg aca ccg act gct aca cca aca gca acg cca            2016
Thr Pro Thr Pro Thr Pro Thr Pro Thr Ala Thr Pro Thr Ala Thr Pro
            660                 665                 670 aca cca aca tcg acg ccg agc agc aca cct gta gca ggt gga cag ata            2064
Thr Pro Thr Ser Thr Pro Ser Ser Thr Pro Val Ala Gly Gly Gln Ile
        675                 680                 685 aag gta ttg tat gct aac aag gag aca aat agc aca act aat acg ata            2112
Lys Val Leu Tyr Ala Asn Lys Glu Thr Asn Ser Thr Thr Asn Thr Ile
    690                 695                 700 agg cca tgg ttg aag gta gtg aac act gga agc agc agc ata gat ttg            2160
Arg Pro Trp Leu Lys Val Val Asn Thr Gly Ser Ser Ser Ile Asp Leu
705                 710                 715                 720 agc agg gta acg ata agg tac tgg tac acg gta gat ggg gac aag gca            2208
Ser Arg Val Thr Ile Arg Tyr Trp Tyr Thr Val Asp Gly Asp Lys Ala
                725                 730                 735 cag agt gcg ata tca gac tgg gca cag ata gga gca agc aat gtg aca            2256
Gln Ser Ala Ile Ser Asp Trp Ala Gln Ile Gly Ala Ser Asn Val Thr
            740                 745                 750 ttc aag ttt gtg aag ctg agc agc agc gta agt gga gcg gac tat tat            2304
Phe Lys Phe Val Lys Leu Ser Ser Ser Val Ser Gly Ala Asp Tyr Tyr
        755                 760                 765 tta gag ata gga ttt aag agt gga gct ggg cag ttg cag gct ggc aaa            2352
Leu Glu Ile Gly Phe Lys Ser Gly Ala Gly Gln Leu Gln Ala Gly Lys
    770                 775                 780 gac aca ggg gag ata cag ata agg ttt aac aag agt gat tgg agc aat            2400
Asp Thr Gly Glu Ile Gln Ile Arg Phe Asn Lys Ser Asp Trp Ser Asn
785                 790                 795                 800 tac aat cag ggg aat gac tgg tca tgg atg cag agc atg acg aat tat            2448
Tyr Asn Gln Gly Asn Asp Trp Ser Trp Met Gln Ser Met Thr Asn Tyr
                805                 810                 815 gga gag aat gtg aag gta aca gcg tat ata gat ggt gta ttg gta tgg            2496
Gly Glu Asn Val Lys Val Thr Ala Tyr Ile Asp Gly Val Leu Val Trp
            820                 825                 830 gga cag gag ccg agt gga gcg aca cca aca ccg aca gcg aca cca gca            2544
Gly Gln Glu Pro Ser Gly Ala Thr Pro Thr Pro Thr Ala Thr Pro Ala
        835                 840                 845
```

```
ccg aca gtg aca ccg aca cct aca cca aca cca acg tca aca cca act      2592
Pro Thr Val Thr Pro Thr Pro Thr Pro Thr Pro Thr Ser Thr Pro Thr
850                 855                 860 gct aca cca aca gca acg cca aca cca aca ccg acg ccg agc agc aca      2640
Ala Thr Pro Thr Ala Thr Pro Thr Pro Thr Pro Thr Pro Ser Ser Thr
865                 870                 875                 880 cct gta gca ggc ggg cag ata aag gta ttg tat gct aac aag gag aca      2688
Pro Val Ala Gly Gly Gln Ile Lys Val Leu Tyr Ala Asn Lys Glu Thr
            885                 890                 895 aat agc aca aca aac acg ata agg cca tgg ttg aag gta gtg aac act      2736
Asn Ser Thr Thr Asn Thr Ile Arg Pro Trp Leu Lys Val Val Asn Thr
            900                 905                 910 gga agc agc agc ata gat ttg agc agg gta acg ata agg tac tgg tac      2784
Gly Ser Ser Ser Ile Asp Leu Ser Arg Val Thr Ile Arg Tyr Trp Tyr
            915                 920                 925 acg gta gat ggg gac aag gca cag agt gcg ata tca gac tgg gca cag      2832
Thr Val Asp Gly Asp Lys Ala Gln Ser Ala Ile Ser Asp Trp Ala Gln
930                 935                 940 ata gga gca agc aat gtg aca ttc aag ttt gtg aag ctg agc agt agc      2880
Ile Gly Ala Ser Asn Val Thr Phe Lys Phe Val Lys Leu Ser Ser Ser
945                 950                 955                 960 gta agt gga gcg gac tat tat tta gag ata gga ttt aag agt gga gct      2928
Val Ser Gly Ala Asp Tyr Tyr Leu Glu Ile Gly Phe Lys Ser Gly Ala
            965                 970                 975 ggg cag ttg cag gct ggt aaa gac aca ggg gag ata cag ata agg ttt      2976
Gly Gln Leu Gln Ala Gly Lys Asp Thr Gly Glu Ile Gln Ile Arg Phe
            980                 985                 990 aac aag agt gac tgg agc aat tac aat cag ggg aat gac tgg tca tgg      3024
Asn Lys Ser Asp Trp Ser Asn Tyr Asn Gln Gly Asn Asp Trp Ser Trp
            995                 1000                1005 atg cag agc atg acg aat tat gga gag aat gtg aag gta aca gcg           3069
Met Gln Ser Met Thr Asn Tyr Gly Glu Asn Val Lys Val Thr Ala
            1010                1015                1020 tat ata gat ggt gta ttg gta tgg gga cag gag ccg agt gga gcg           3114
Tyr Ile Asp Gly Val Leu Val Trp Gly Gln Glu Pro Ser Gly Ala
            1025                1030                1035 aca cca aca ccg aca gcg aca cca gca ccg aca gtg aca ccg aca           3159
Thr Pro Thr Pro Thr Ala Thr Pro Ala Pro Thr Val Thr Pro Thr
            1040                1045                1050 cct aca cca gca cca act cca acc ccg aca cca aca cca act gct           3204
Pro Thr Pro Ala Pro Thr Pro Thr Pro Thr Pro Thr Pro Thr Ala
            1055                1060                1065 aca cca aca cca acg cca aca cca acc cca acc gcg aca cca aca           3249
Thr Pro Thr Pro Thr Pro Thr Pro Thr Pro Thr Ala Thr Pro Thr
            1070                1075                1080 gta aca gca aca cca aca ccg acg ccg agc agc aca ccg agt gtg           3294
Val Thr Ala Thr Pro Thr Pro Thr Pro Ser Ser Thr Pro Ser Val
            1085                1090                1095 ctt ggc gaa tat ggg cag agg ttt atg tgg tta tgg aac aag ata           3339
Leu Gly Glu Tyr Gly Gln Arg Phe Met Trp Leu Trp Asn Lys Ile
            1100                1105                1110 cat gat cct gcg aac ggg tat ttt aac cag gat ggg ata cca tat           3384
His Asp Pro Ala Asn Gly Tyr Phe Asn Gln Asp Gly Ile Pro Tyr
            1115                1120                1125 cat tcg gta gag aca ttg ata tgc gaa gca cct gat tat ggt cat           3429
His Ser Val Glu Thr Leu Ile Cys Glu Ala Pro Asp Tyr Gly His
            1130                1135                1140 ttg acc acg agt gag gca ttt tcg tac tat gta tgg tta gag gca           3474
Leu Thr Thr Ser Glu Ala Phe Ser Tyr Tyr Val Trp Leu Glu Ala
            1145                1150                1155
```

-continued

| | | | | | | | | | | | | |
|---|---|---|---|---|---|---|---|---|---|---|---|---|
| gtg | tat | ggt | aag | tta | acg | ggt | gac | tgg | agc | aaa | ttt | aag aca gca | 3519 |
| Val | Tyr | Gly | Lys | Leu | Thr | Gly | Asp | Trp | Ser | Lys | Phe | Lys Thr Ala | |
| | 1160 | | | | 1165 | | | | 1170 | | | | |

```
gtg tat ggt aag tta acg ggt gac tgg agc aaa ttt aag aca gca       3519
Val Tyr Gly Lys Leu Thr Gly Asp Trp Ser Lys Phe Lys Thr Ala
    1160                1165                1170 tgg gac aca tta gag aag tat atg ata cca tca gcg gaa gat cag       3564
Trp Asp Thr Leu Glu Lys Tyr Met Ile Pro Ser Ala Glu Asp Gln
1175                1180                1185 ccg atg agg tca tat gat cct aac aag cca gcg aca tac gca ggg       3609
Pro Met Arg Ser Tyr Asp Pro Asn Lys Pro Ala Thr Tyr Ala Gly
    1190                1195                1200 gag tgg gag aca ccg gac aag tat cca tcg ccg ttg gag ttt aat       3654
Glu Trp Glu Thr Pro Asp Lys Tyr Pro Ser Pro Leu Glu Phe Asn
1205                1210                1215 gta cct gtt ggc aaa gac ccg ttg cat aat gaa ctt gtg agc aca       3699
Val Pro Val Gly Lys Asp Pro Leu His Asn Glu Leu Val Ser Thr
    1220                1225                1230 tat ggt agc aca tta atg tat ggt atg cac tgg ttg atg gac gta       3744
Tyr Gly Ser Thr Leu Met Tyr Gly Met His Trp Leu Met Asp Val
1235                1240                1245 gac aac tgg tat gga tat ggc aag aga ggg gac gga gta agt cgg       3789
Asp Asn Trp Tyr Gly Tyr Gly Lys Arg Gly Asp Gly Val Ser Arg
    1250                1255                1260 gca tca ttt atc aac acg ttc cag aga ggg cct gag gag tct gta       3834
Ala Ser Phe Ile Asn Thr Phe Gln Arg Gly Pro Glu Glu Ser Val
1265                1270                1275 tgg gag acg gtg ccg cat ccg agc tgg gag gaa ttc aag tgg ggc       3879
Trp Glu Thr Val Pro His Pro Ser Trp Glu Glu Phe Lys Trp Gly
    1280                1285                1290 gga ccg aat gga ttt tta gat ttg ttt att aag gat cag aac tat       3924
Gly Pro Asn Gly Phe Leu Asp Leu Phe Ile Lys Asp Gln Asn Tyr
1295                1300                1305 tcg aag cag tgg aga tat acg gat gca cca gat gct gat gcg aga       3969
Ser Lys Gln Trp Arg Tyr Thr Asp Ala Pro Asp Ala Asp Ala Arg
    1310                1315                1320 gct att cag gct act tat tgg gcg aaa gta tgg gcg aag gag caa       4014
Ala Ile Gln Ala Thr Tyr Trp Ala Lys Val Trp Ala Lys Glu Gln
1325                1330                1335 ggt aag ttt aat gag ata agc agc tat gta gcg aag gca gcg aag       4059
Gly Lys Phe Asn Glu Ile Ser Ser Tyr Val Ala Lys Ala Ala Lys
    1340                1345                1350 atg gga gac tat tta agg tat gcg atg ttt gac aag tat ttc aag       4104
Met Gly Asp Tyr Leu Arg Tyr Ala Met Phe Asp Lys Tyr Phe Lys
1355                1360                1365 cca tta gga tgt cag gat aag aat gcg gct gga gga acg ggg tat       4149
Pro Leu Gly Cys Gln Asp Lys Asn Ala Ala Gly Gly Thr Gly Tyr
    1370                1375                1380 gac agt gca cat tat ctg cta tca tgg tat tat gca tgg ggt gga       4194
Asp Ser Ala His Tyr Leu Leu Ser Trp Tyr Tyr Ala Trp Gly Gly
1385                1390                1395 gca ttg gat gga gca tgg tca tgg aag ata ggg agc agc cat gtg       4239
Ala Leu Asp Gly Ala Trp Ser Trp Lys Ile Gly Ser Ser His Val
    1400                1405                1410 cac ttt gga tat cag aat ccg atg gcg gca tgg gca tta gcg aat       4284
His Phe Gly Tyr Gln Asn Pro Met Ala Ala Trp Ala Leu Ala Asn
1415                1420                1425 gat agt gat atg aag ccg aag tcg ccg aat gga gcg agt gac tgg       4329
Asp Ser Asp Met Lys Pro Lys Ser Pro Asn Gly Ala Ser Asp Trp
    1430                1435                1440 gca aag agt ttg aag agg cag ata gaa ttt tac agg tgg tta cag       4374
Ala Lys Ser Leu Lys Arg Gln Ile Glu Phe Tyr Arg Trp Leu Gln
```

```
             1445                1450                1455
tca gcg gag gga gcg ata gca gga ggc gcg aca aat tca tgg aat      4419
Ser Ala Glu Gly Ala Ile Ala Gly Gly Ala Thr Asn Ser Trp Asn
1460                1465                1470 ggc aga tat gag aag tat cca gca ggg aca gca aca ttt tat gga      4464
Gly Arg Tyr Glu Lys Tyr Pro Ala Gly Thr Ala Thr Phe Tyr Gly
1475                1480                1485 atg gca tat gaa ccg aat ccg gta tat cat gat cct ggg agc aac      4509
Met Ala Tyr Glu Pro Asn Pro Val Tyr His Asp Pro Gly Ser Asn
1490                1495                1500 aca tgg ttt gga ttc cag gca tgg tcg atg cag agg gta gcg gag      4554
Thr Trp Phe Gly Phe Gln Ala Trp Ser Met Gln Arg Val Ala Glu
1505                1510                1515 tat tac tat gtg aca gga gat aag gac gca gga gca ctg ctt gag      4599
Tyr Tyr Tyr Val Thr Gly Asp Lys Asp Ala Gly Ala Leu Leu Glu
1520                1525                1530 aag tgg gta agc tgg gtt aag agt gta gtg aag ttg aat agt gat      4644
Lys Trp Val Ser Trp Val Lys Ser Val Val Lys Leu Asn Ser Asp
1535                1540                1545 ggt acg ttt gcg ata ccg tcg acg ctt gat tgg agc gga caa cct      4689
Gly Thr Phe Ala Ile Pro Ser Thr Leu Asp Trp Ser Gly Gln Pro
1550                1555                1560 gat aca tgg aac ggg gcg tat aca ggg aat agc aac tta cat gtt      4734
Asp Thr Trp Asn Gly Ala Tyr Thr Gly Asn Ser Asn Leu His Val
1565                1570                1575 aag gta gtg gac tat ggt act gac tta gga ata aca gcg tca ttg      4779
Lys Val Val Asp Tyr Gly Thr Asp Leu Gly Ile Thr Ala Ser Leu
1580                1585                1590 gcg aat gcg ttg ttg tac tat agt gca ggg acg aag aag tat ggg      4824
Ala Asn Ala Leu Leu Tyr Tyr Ser Ala Gly Thr Lys Lys Tyr Gly
1595                1600                1605 gta ttt gat gag gga gcg aag aat tta gcg aag gaa ttg ctg gac      4869
Val Phe Asp Glu Gly Ala Lys Asn Leu Ala Lys Glu Leu Leu Asp
1610                1615                1620 agg atg tgg aag ttg tac agg gat gag aag gga ttg tca gcg cca      4914
Arg Met Trp Lys Leu Tyr Arg Asp Glu Lys Gly Leu Ser Ala Pro
1625                1630                1635 gag aag aga gcg gac tac aag agg ttc ttt gag caa gag gta tat      4959
Glu Lys Arg Ala Asp Tyr Lys Arg Phe Phe Glu Gln Glu Val Tyr
1640                1645                1650 ata ccg gca gga tgg ata ggg aag atg ccg aat gga gat gta ata      5004
Ile Pro Ala Gly Trp Ile Gly Lys Met Pro Asn Gly Asp Val Ile
1655                1660                1665 aag agt gga gtt aag ttt ata gac ata agg agc aag tat aaa caa      5049
Lys Ser Gly Val Lys Phe Ile Asp Ile Arg Ser Lys Tyr Lys Gln
1670                1675                1680 gat cct gat tgg ccg aag tta gag gcg gca tac aag tca ggg cag      5094
Asp Pro Asp Trp Pro Lys Leu Glu Ala Ala Tyr Lys Ser Gly Gln
1685                1690                1695 gca cct gag ttc aga tat cac agg ttc tgg gca cag tgc gac ata      5139
Ala Pro Glu Phe Arg Tyr His Arg Phe Trp Ala Gln Cys Asp Ile
1700                1705                1710 gca ata gct aat gca aca tat gaa ata ctg ttt ggc aat caa          5181
Ala Ile Ala Asn Ala Thr Tyr Glu Ile Leu Phe Gly Asn Gln
1715                1720                1725

<210> SEQ ID NO 4
<211> LENGTH: 1727
<212> TYPE: PRT
<213> ORGANISM: Caldicellulosiruptor bescii
```

<400> SEQUENCE: 4

```
Gly Ser Phe Asn Tyr Gly Glu Ala Leu Gln Lys Ala Ile Met Phe Tyr
1               5                   10                  15

Glu Phe Gln Met Ser Gly Lys Leu Pro Asn Trp Val Arg Asn Asn Trp
            20                  25                  30

Arg Gly Asp Ser Ala Leu Lys Asp Gly Gln Asp Asn Gly Leu Asp Leu
        35                  40                  45

Thr Gly Gly Trp Phe Asp Ala Gly Asp His Val Lys Phe Asn Leu Pro
    50                  55                  60

Met Ser Tyr Thr Gly Thr Met Leu Ser Trp Ala Val Tyr Glu Tyr Lys
65                  70                  75                  80

Asp Ala Phe Val Lys Ser Gly Gln Leu Glu His Ile Leu Asn Gln Ile
                85                  90                  95

Glu Trp Val Asn Asp Tyr Phe Val Lys Cys His Pro Ser Lys Tyr Val
            100                 105                 110

Tyr Tyr Tyr Gln Val Gly Asp Gly Ser Lys Asp His Ala Trp Trp Gly
        115                 120                 125

Pro Ala Glu Val Met Gln Met Glu Arg Pro Ser Phe Lys Val Thr Gln
130                 135                 140

Ser Ser Pro Gly Ser Thr Val Val Ala Glu Thr Ala Ala Ser Leu Ala
145                 150                 155                 160

Ala Ala Ser Ile Val Leu Lys Asp Arg Asn Pro Thr Lys Ala Ala Thr
                165                 170                 175

Tyr Leu Gln His Ala Lys Glu Leu Tyr Glu Phe Ala Glu Val Thr Lys
            180                 185                 190

Ser Asp Ala Gly Tyr Thr Ala Ala Asn Gly Tyr Tyr Asn Ser Trp Ser
        195                 200                 205

Gly Phe Tyr Asp Glu Leu Ser Trp Ala Ala Val Trp Leu Tyr Leu Ala
    210                 215                 220

Thr Asn Asp Ser Thr Tyr Leu Thr Lys Ala Glu Ser Tyr Val Gln Asn
225                 230                 235                 240

Trp Pro Lys Ile Ser Gly Ser Asn Thr Ile Asp Tyr Lys Trp Ala His
                245                 250                 255

Cys Trp Asp Asp Val His Asn Gly Ala Ala Leu Leu Leu Ala Lys Ile
            260                 265                 270

Thr Gly Lys Asp Ile Tyr Lys Gln Ile Ile Glu Ser His Leu Asp Tyr
        275                 280                 285

Trp Thr Thr Gly Tyr Asn Gly Glu Arg Ile Lys Tyr Thr Pro Lys Gly
    290                 295                 300

Leu Ala Trp Leu Asp Gln Trp Gly Ser Leu Arg Tyr Ala Thr Thr Thr
305                 310                 315                 320

Ala Phe Leu Ala Phe Val Tyr Ser Asp Trp Val Gly Cys Pro Ser Thr
                325                 330                 335

Lys Lys Glu Ile Tyr Arg Lys Phe Gly Glu Ser Gln Ile Asp Tyr Ala
            340                 345                 350

Leu Gly Ser Ala Gly Arg Ser Phe Val Val Gly Phe Gly Thr Asn Pro
        355                 360                 365

Pro Lys Arg Pro His His Arg Thr Ala His Ser Ser Trp Ala Asp Ser
    370                 375                 380

Gln Ser Ile Pro Ser Tyr His Arg His Thr Leu Tyr Gly Ala Leu Val
385                 390                 395                 400

Gly Gly Pro Gly Ser Asp Asp Ser Tyr Thr Asp Asp Ile Ser Asn Tyr
```

```
                405                 410                 415
Val Asn Asn Glu Val Ala Cys Asp Tyr Asn Ala Gly Phe Val Gly Ala
            420                 425                 430
Leu Ala Lys Met Tyr Gln Leu Tyr Gly Gly Asn Pro Ile Pro Asp Phe
            435                 440                 445
Lys Ala Ile Glu Thr Pro Thr Asn Asp Glu Phe Phe Val Glu Ala Gly
            450                 455                 460
Ile Asn Ala Ser Gly Thr Asn Phe Ile Glu Ile Lys Ala Ile Val Asn
465                 470                 475                 480
Asn Gln Ser Gly Trp Pro Ala Arg Ala Thr Asp Lys Leu Lys Phe Arg
            485                 490                 495
Tyr Phe Val Asp Leu Ser Glu Leu Ile Lys Ala Gly Tyr Ser Pro Asn
            500                 505                 510
Gln Leu Thr Leu Ser Thr Asn Tyr Asn Gln Gly Ala Lys Val Ser Gly
            515                 520                 525
Pro Tyr Val Trp Asp Ala Ser Lys Asn Ile Tyr Tyr Ile Leu Val Asp
            530                 535                 540
Phe Thr Gly Thr Leu Ile Tyr Pro Gly Gly Gln Asp Lys Tyr Lys Lys
545                 550                 555                 560
Glu Val Gln Phe Arg Ile Ala Ala Pro Gln Asn Val Gln Trp Asp Asn
            565                 570                 575
Ser Asn Asp Tyr Ser Phe Gln Asp Ile Lys Gly Val Ser Gly Ser
            580                 585                 590
Val Val Lys Thr Lys Tyr Ile Pro Leu Tyr Asp Gly Asp Val Lys Val
            595                 600                 605
Trp Gly Glu Glu Pro Gly Thr Ser Gly Ala Thr Pro Thr Pro Thr Ala
            610                 615                 620
Thr Ala Thr Pro Thr Pro Thr Pro Thr Val Thr Pro Thr Pro Thr Pro
625                 630                 635                 640
Thr Pro Thr Ser Thr Ala Thr Pro Thr Pro Thr Pro Thr Pro Thr Val
            645                 650                 655
Thr Pro Thr Pro Thr Pro Thr Pro Thr Ala Thr Pro Thr Ala Thr Pro
            660                 665                 670
Thr Pro Thr Ser Thr Pro Ser Ser Thr Pro Val Ala Gly Gly Gln Ile
            675                 680                 685
Lys Val Leu Tyr Ala Asn Lys Glu Thr Asn Ser Thr Thr Asn Thr Ile
            690                 695                 700
Arg Pro Trp Leu Lys Val Val Asn Thr Gly Ser Ser Ser Ile Asp Leu
705                 710                 715                 720
Ser Arg Val Thr Ile Arg Tyr Trp Tyr Thr Val Asp Gly Asp Lys Ala
            725                 730                 735
Gln Ser Ala Ile Ser Asp Trp Ala Gln Ile Gly Ala Ser Asn Val Thr
            740                 745                 750
Phe Lys Phe Val Lys Leu Ser Ser Ser Val Ser Gly Ala Asp Tyr Tyr
            755                 760                 765
Leu Glu Ile Gly Phe Lys Ser Gly Ala Gly Gln Leu Gln Ala Gly Lys
            770                 775                 780
Asp Thr Gly Glu Ile Gln Ile Arg Phe Asn Lys Ser Asp Trp Ser Asn
785                 790                 795                 800
Tyr Asn Gln Gly Asn Asp Trp Ser Trp Met Gln Ser Met Thr Asn Tyr
            805                 810                 815
Gly Glu Asn Val Lys Val Thr Ala Tyr Ile Asp Gly Val Leu Val Trp
            820                 825                 830
```

```
Gly Gln Glu Pro Ser Gly Ala Thr Pro Thr Pro Thr Ala Thr Pro Ala
            835                 840                 845

Pro Thr Val Thr Pro Thr Pro Thr Pro Thr Pro Thr Ser Thr Pro Thr
850                 855                 860

Ala Thr Pro Thr Ala Thr Pro Thr Pro Thr Pro Thr Pro Ser Ser Thr
865                 870                 875                 880

Pro Val Ala Gly Gly Gln Ile Lys Val Leu Tyr Ala Asn Lys Glu Thr
                885                 890                 895

Asn Ser Thr Thr Asn Thr Ile Arg Pro Trp Leu Lys Val Val Asn Thr
                900                 905                 910

Gly Ser Ser Ile Asp Leu Ser Arg Val Thr Ile Arg Tyr Trp Tyr
                915                 920                 925

Thr Val Asp Gly Asp Lys Ala Gln Ser Ala Ile Ser Asp Trp Ala Gln
            930                 935                 940

Ile Gly Ala Ser Asn Val Thr Phe Lys Phe Val Lys Leu Ser Ser Ser
945                 950                 955                 960

Val Ser Gly Ala Asp Tyr Tyr Leu Glu Ile Gly Phe Lys Ser Gly Ala
                965                 970                 975

Gly Gln Leu Gln Ala Gly Lys Asp Thr Gly Glu Ile Gln Ile Arg Phe
            980                 985                 990

Asn Lys Ser Asp Trp Ser Asn Tyr  Asn Gln Gly Asn Asp  Trp Ser Trp
            995                 1000                1005

Met Gln Ser Met Thr Asn Tyr  Gly Glu Asn Val Lys  Val Thr Ala
            1010                1015                1020

Tyr Ile Asp Gly Val Leu Val  Trp Gly Gln Glu Pro  Ser Gly Ala
            1025                1030                1035

Thr Pro Thr Pro Thr Ala Thr  Pro Ala Pro Thr Val  Thr Pro Thr
            1040                1045                1050

Pro Thr Pro Ala Pro Thr Pro  Thr Pro Thr Pro Thr  Pro Thr Ala
            1055                1060                1065

Thr Pro Thr Pro Thr Pro Thr  Pro Thr Pro Thr Ala  Thr Pro Thr
            1070                1075                1080

Val Thr Ala Thr Pro Thr Pro  Thr Pro Ser Ser Thr  Pro Ser Val
            1085                1090                1095

Leu Gly Glu Tyr Gly Gln Arg  Phe Met Trp Leu Trp  Asn Lys Ile
            1100                1105                1110

His Asp Pro Ala Asn Gly Tyr  Phe Asn Gln Asp Gly  Ile Pro Tyr
            1115                1120                1125

His Ser Val Glu Thr Leu Ile  Cys Glu Ala Pro Asp  Tyr Gly His
            1130                1135                1140

Leu Thr Thr Ser Glu Ala Phe  Ser Tyr Tyr Val Trp  Leu Glu Ala
            1145                1150                1155

Val Tyr Gly Lys Leu Thr Gly  Asp Trp Ser Lys Phe  Lys Thr Ala
            1160                1165                1170

Trp Asp Thr Leu Glu Lys Tyr  Met Ile Pro Ser Ala  Glu Asp Gln
            1175                1180                1185

Pro Met Arg Ser Tyr Asp Pro  Asn Lys Pro Ala Thr  Tyr Ala Gly
            1190                1195                1200

Glu Trp Glu Thr Pro Asp Lys  Tyr Pro Ser Pro Leu  Glu Phe Asn
            1205                1210                1215

Val Pro Val Gly Lys Asp Pro  Leu His Asn Glu Leu  Val Ser Thr
            1220                1225                1230
```

```
Tyr Gly Ser Thr Leu Met Tyr Gly Met His Trp Leu Met Asp Val
    1235             1240             1245

Asp Asn Trp Tyr Gly Tyr Gly Lys Arg Gly Asp Gly Val Ser Arg
    1250             1255             1260

Ala Ser Phe Ile Asn Thr Phe Gln Arg Gly Pro Glu Glu Ser Val
    1265             1270             1275

Trp Glu Thr Val Pro His Pro Ser Trp Glu Glu Phe Lys Trp Gly
    1280             1285             1290

Gly Pro Asn Gly Phe Leu Asp Leu Phe Ile Lys Asp Gln Asn Tyr
    1295             1300             1305

Ser Lys Gln Trp Arg Tyr Thr Asp Ala Pro Asp Ala Asp Ala Arg
    1310             1315             1320

Ala Ile Gln Ala Thr Tyr Trp Ala Lys Val Trp Ala Lys Glu Gln
    1325             1330             1335

Gly Lys Phe Asn Glu Ile Ser Ser Tyr Val Ala Lys Ala Ala Lys
    1340             1345             1350

Met Gly Asp Tyr Leu Arg Tyr Ala Met Phe Asp Lys Tyr Phe Lys
    1355             1360             1365

Pro Leu Gly Cys Gln Asp Lys Asn Ala Ala Gly Gly Thr Gly Tyr
    1370             1375             1380

Asp Ser Ala His Tyr Leu Leu Ser Trp Tyr Tyr Ala Trp Gly Gly
    1385             1390             1395

Ala Leu Asp Gly Ala Trp Ser Trp Lys Ile Gly Ser Ser His Val
    1400             1405             1410

His Phe Gly Tyr Gln Asn Pro Met Ala Trp Ala Leu Ala Asn
    1415             1420             1425

Asp Ser Asp Met Lys Pro Lys Ser Pro Asn Gly Ala Ser Asp Trp
    1430             1435             1440

Ala Lys Ser Leu Lys Arg Gln Ile Glu Phe Tyr Arg Trp Leu Gln
    1445             1450             1455

Ser Ala Glu Gly Ala Ile Ala Gly Gly Ala Thr Asn Ser Trp Asn
    1460             1465             1470

Gly Arg Tyr Glu Lys Tyr Pro Ala Gly Thr Ala Thr Phe Tyr Gly
    1475             1480             1485

Met Ala Tyr Glu Pro Asn Pro Val Tyr His Asp Pro Gly Ser Asn
    1490             1495             1500

Thr Trp Phe Gly Phe Gln Ala Trp Ser Met Gln Arg Val Ala Glu
    1505             1510             1515

Tyr Tyr Tyr Val Thr Gly Asp Lys Asp Ala Gly Ala Leu Leu Glu
    1520             1525             1530

Lys Trp Val Ser Trp Val Lys Ser Val Val Lys Leu Asn Ser Asp
    1535             1540             1545

Gly Thr Phe Ala Ile Pro Ser Thr Leu Asp Trp Ser Gly Gln Pro
    1550             1555             1560

Asp Thr Trp Asn Gly Ala Tyr Thr Gly Asn Ser Asn Leu His Val
    1565             1570             1575

Lys Val Val Asp Tyr Gly Thr Asp Leu Gly Ile Thr Ala Ser Leu
    1580             1585             1590

Ala Asn Ala Leu Leu Tyr Tyr Ser Ala Gly Thr Lys Lys Tyr Gly
    1595             1600             1605

Val Phe Asp Glu Gly Ala Lys Asn Leu Ala Lys Glu Leu Leu Asp
    1610             1615             1620

Arg Met Trp Lys Leu Tyr Arg Asp Glu Lys Gly Leu Ser Ala Pro
```

```
                    1625                1630                1635

Glu Lys Arg Ala Asp Tyr Lys Arg Phe Phe Gln Glu Val Tyr
        1640                1645                1650

Ile Pro Ala Gly Trp Ile Gly Lys Met Pro Asn Gly Asp Val Ile
        1655                1660                1665

Lys Ser Gly Val Lys Phe Ile Asp Ile Arg Ser Lys Tyr Lys Gln
        1670                1675                1680

Asp Pro Asp Trp Pro Lys Leu Glu Ala Ala Tyr Lys Ser Gly Gln
        1685                1690                1695

Ala Pro Glu Phe Arg Tyr His Arg Phe Trp Ala Gln Cys Asp Ile
        1700                1705                1710

Ala Ile Ala Asn Ala Thr Tyr Glu Ile Leu Phe Gly Asn Gln
        1715                1720                1725

<210> SEQ ID NO 5
<211> LENGTH: 3216
<212> TYPE: DNA
<213> ORGANISM: Artificial Sequence
<220> FEATURE:
<223> OTHER INFORMATION: Chimeric Sequence
<220> FEATURE:
<221> NAME/KEY: CDS
<222> LOCATION: (1)..(3216)

<400> SEQUENCE: 5 tta gaa gat aat tct tcg act ttg ccg ccg tat aaa aac gac ctt ttg      48
Leu Glu Asp Asn Ser Ser Thr Leu Pro Pro Tyr Lys Asn Asp Leu Leu
1               5                   10                  15 tat gag agg act ttt gat gag gga ctt tgt tat cca tgg cat acc tgt     96
Tyr Glu Arg Thr Phe Asp Glu Gly Leu Cys Tyr Pro Trp His Thr Cys
            20                  25                  30 gaa gac agc gga gga aaa tgc tcc ttt gat gtg gtc gat gtt ccg ggg    144
Glu Asp Ser Gly Gly Lys Cys Ser Phe Asp Val Val Asp Val Pro Gly
        35                  40                  45 cag ccc ggt aat aaa gca ttt gcc gtt act gtt ctt gac aaa ggg caa    192
Gln Pro Gly Asn Lys Ala Phe Ala Val Thr Val Leu Asp Lys Gly Gln
    50                  55                  60 aac aga tgg agc gtt cag atg aga cac cgt ggt ctt act ctt gaa cag    240
Asn Arg Trp Ser Val Gln Met Arg His Arg Gly Leu Thr Leu Glu Gln
65                  70                  75                  80 gga cat aca tat aga gta cgg ctt aag att tgg gca gat gcg tcc tgt    288
Gly His Thr Tyr Arg Val Arg Leu Lys Ile Trp Ala Asp Ala Ser Cys
                85                  90                  95 aaa gtt tat ata aaa ata gga caa atg ggc gag ccc tat gct gaa tat    336
Lys Val Tyr Ile Lys Ile Gly Gln Met Gly Glu Pro Tyr Ala Glu Tyr
            100                 105                 110 tgg aac aac aag tgg agt cca tac aca ctg aca gca ggt aag gta ttg    384
Trp Asn Asn Lys Trp Ser Pro Tyr Thr Leu Thr Ala Gly Lys Val Leu
        115                 120                 125 gaa att gac gag acg ttt gtt atg gac aag cca act gac gac aca tgc    432
Glu Ile Asp Glu Thr Phe Val Met Asp Lys Pro Thr Asp Asp Thr Cys
    130                 135                 140 gaa ttt aca ttc cat tta ggt ggc gaa ttg gca gca act cct cca tat    480
Glu Phe Thr Phe His Leu Gly Gly Glu Leu Ala Ala Thr Pro Pro Tyr
145                 150                 155                 160 aca gtt tat ctt gat gat gta tcc ctt tat gac cca gaa tat acg aag    528
Thr Val Tyr Leu Asp Asp Val Ser Leu Tyr Asp Pro Glu Tyr Thr Lys
                165                 170                 175 cct gtt gaa tat ata ctt ccg cag cct gat gta cgt gtg aac cag gtt    576
Pro Val Glu Tyr Ile Leu Pro Gln Pro Asp Val Arg Val Asn Gln Val
```

|   |   |   |   |   |   |   |   |   |   |   |   |   |   |   |   |   |
|---|---|---|---|---|---|---|---|---|---|---|---|---|---|---|---|---|
|   |   |   | 180 |   |   |   |   | 185 |   |   |   |   | 190 |   |   |   |
| ggc | tac | ctg | ccg | gag | ggc | aag | aaa | gtt | gcc | act | gtg | gta | tgc | aat | tca | 624 |
| Gly | Tyr | Leu | Pro | Glu | Gly | Lys | Lys | Val | Ala | Thr | Val | Val | Cys | Asn | Ser |   |
|   |   | 195 |   |   |   |   | 200 |   |   |   |   | 205 |   |   |   |   |
| act | cag | ccg | gta | aaa | tgg | cag | ctt | aag | aat | gct | gca | ggc | gtt | gta | gtt | 672 |
| Thr | Gln | Pro | Val | Lys | Trp | Gln | Leu | Lys | Asn | Ala | Ala | Gly | Val | Val | Val |   |
|   | 210 |   |   |   |   | 215 |   |   |   |   | 220 |   |   |   |   |   |
| ttg | gaa | ggt | tat | acc | gaa | cca | aag | ggt | ctt | gac | aaa | gac | tcg | cag | gat | 720 |
| Leu | Glu | Gly | Tyr | Thr | Glu | Pro | Lys | Gly | Leu | Asp | Lys | Asp | Ser | Gln | Asp |   |
| 225 |   |   |   |   | 230 |   |   |   |   | 235 |   |   |   |   | 240 |   |
| tat | gta | cat | tgg | ctt | gat | ttt | tcc | gat | ttt | gca | acc | gaa | gga | att | ggt | 768 |
| Tyr | Val | His | Trp | Leu | Asp | Phe | Ser | Asp | Phe | Ala | Thr | Glu | Gly | Ile | Gly |   |
|   |   |   |   | 245 |   |   |   |   | 250 |   |   |   |   | 255 |   |   |
| tac | tat | ttt | gaa | ctt | ccg | act | gta | aac | agt | cct | aca | aac | tac | agt | cat | 816 |
| Tyr | Tyr | Phe | Glu | Leu | Pro | Thr | Val | Asn | Ser | Pro | Thr | Asn | Tyr | Ser | His |   |
|   |   |   | 260 |   |   |   |   | 265 |   |   |   |   | 270 |   |   |   |
| cca | ttt | gac | att | cgc | aaa | gac | atc | tat | act | cag | atg | aaa | tat | gat | gca | 864 |
| Pro | Phe | Asp | Ile | Arg | Lys | Asp | Ile | Tyr | Thr | Gln | Met | Lys | Tyr | Asp | Ala |   |
|   |   | 275 |   |   |   |   | 280 |   |   |   |   | 285 |   |   |   |   |
| ttg | gca | ttc | ttc | tat | cac | aag | aga | agc | ggt | att | cct | att | gaa | atg | ccg | 912 |
| Leu | Ala | Phe | Phe | Tyr | His | Lys | Arg | Ser | Gly | Ile | Pro | Ile | Glu | Met | Pro |   |
|   | 290 |   |   |   |   | 295 |   |   |   |   | 300 |   |   |   |   |   |
| tat | gca | gga | gga | gaa | cag | tgg | acc | aga | cct | gca | gga | cat | atc | gga | att | 960 |
| Tyr | Ala | Gly | Gly | Glu | Gln | Trp | Thr | Arg | Pro | Ala | Gly | His | Ile | Gly | Ile |   |
| 305 |   |   |   |   | 310 |   |   |   |   | 315 |   |   |   |   | 320 |   |
| gag | ccg | aac | aag | gga | gat | aca | aat | gtt | cct | aca | tgg | cct | cag | gat | gat | 1008 |
| Glu | Pro | Asn | Lys | Gly | Asp | Thr | Asn | Val | Pro | Thr | Trp | Pro | Gln | Asp | Asp |   |
|   |   |   |   | 325 |   |   |   |   | 330 |   |   |   |   | 335 |   |   |
| gag | tat | gca | gga | ata | cct | cag | aag | aat | tat | aca | aag | gat | gta | acc | ggt | 1056 |
| Glu | Tyr | Ala | Gly | Ile | Pro | Gln | Lys | Asn | Tyr | Thr | Lys | Asp | Val | Thr | Gly |   |
|   |   |   | 340 |   |   |   |   | 345 |   |   |   |   | 350 |   |   |   |
| gga | tgg | tat | gat | gcc | ggt | gac | cac | ggt | aaa | tat | gtt | gta | aac | ggc | ggt | 1104 |
| Gly | Trp | Tyr | Asp | Ala | Gly | Asp | His | Gly | Lys | Tyr | Val | Val | Asn | Gly | Gly |   |
|   |   | 355 |   |   |   |   | 360 |   |   |   |   | 365 |   |   |   |   |
| ata | gcc | gtc | tgg | aca | tta | atg | aac | atg | tat | gag | agg | gca | aaa | att | aga | 1152 |
| Ile | Ala | Val | Trp | Thr | Leu | Met | Asn | Met | Tyr | Glu | Arg | Ala | Lys | Ile | Arg |   |
|   | 370 |   |   |   |   | 375 |   |   |   |   | 380 |   |   |   |   |   |
| ggt | ctt | gac | aac | tgg | gga | cca | tac | agg | gac | ggc | gga | atg | aac | ata | ccg | 1200 |
| Gly | Leu | Asp | Asn | Trp | Gly | Pro | Tyr | Arg | Asp | Gly | Gly | Met | Asn | Ile | Pro |   |
| 385 |   |   |   |   | 390 |   |   |   |   | 395 |   |   |   |   | 400 |   |
| gag | cag | aat | aac | ggt | tat | ccg | gac | att | ctt | gat | gaa | gca | aga | tgg | gaa | 1248 |
| Glu | Gln | Asn | Asn | Gly | Tyr | Pro | Asp | Ile | Leu | Asp | Glu | Ala | Arg | Trp | Glu |   |
|   |   |   |   | 405 |   |   |   |   | 410 |   |   |   |   | 415 |   |   |
| att | gag | ttc | ttt | aag | aaa | atg | cag | gta | act | gaa | aaa | gag | gat | cct | tcc | 1296 |
| Ile | Glu | Phe | Phe | Lys | Lys | Met | Gln | Val | Thr | Glu | Lys | Glu | Asp | Pro | Ser |   |
|   |   |   | 420 |   |   |   |   | 425 |   |   |   |   | 430 |   |   |   |
| ata | gcc | gga | atg | gta | cac | cac | aaa | att | cac | gac | ttc | aga | tgg | act | gct | 1344 |
| Ile | Ala | Gly | Met | Val | His | His | Lys | Ile | His | Asp | Phe | Arg | Trp | Thr | Ala |   |
|   |   | 435 |   |   |   |   | 440 |   |   |   |   | 445 |   |   |   |   |
| ttg | ggt | atg | ttg | cct | cac | gaa | gat | ccc | cag | cca | cgt | tac | tta | agg | ccg | 1392 |
| Leu | Gly | Met | Leu | Pro | His | Glu | Asp | Pro | Gln | Pro | Arg | Tyr | Leu | Arg | Pro |   |
|   | 450 |   |   |   |   | 455 |   |   |   |   | 460 |   |   |   |   |   |
| gta | agt | acg | gct | gcg | act | ttg | aac | ttt | gcg | gca | act | ttg | gca | caa | agt | 1440 |
| Val | Ser | Thr | Ala | Ala | Thr | Leu | Asn | Phe | Ala | Ala | Thr | Leu | Ala | Gln | Ser |   |
| 465 |   |   |   |   | 470 |   |   |   |   | 475 |   |   |   |   | 480 |   |
| gca | cgt | ctt | tgg | aaa | gat | tat | gat | ccg | act | ttt | gct | gct | gac | tgt | ttg | 1488 |
| Ala | Arg | Leu | Trp | Lys | Asp | Tyr | Asp | Pro | Thr | Phe | Ala | Ala | Asp | Cys | Leu |   |
|   |   |   |   | 485 |   |   |   |   | 490 |   |   |   |   | 495 |   |   |
| gaa | aag | gct | gaa | ata | gca | tgg | cag | gcg | gca | tta | aag | cat | cct | gat | att | 1536 |

|     |     |     |     |     |     |     |     |     |     |     |     |     |     |     |      |
|-----|-----|-----|-----|-----|-----|-----|-----|-----|-----|-----|-----|-----|-----|-----|------|
| Glu | Lys | Ala | Glu | Ile | Ala | Trp | Gln | Ala | Ala | Leu | Lys | His | Pro | Asp | Ile  |
|     |     |     |     | 500 |     |     |     | 505 |     |     |     |     | 510 |     |      |

```
tat gct gag tat act ccc ggt agc ggt ggt ccc gga ggc gga cca tac        1584
Tyr Ala Glu Tyr Thr Pro Gly Ser Gly Gly Pro Gly Gly Gly Pro Tyr
            515                 520                 525 aat gac gac tat gtc gga gac gaa ttc tac tgg gca gcc tgc gaa ctt        1632
Asn Asp Asp Tyr Val Gly Asp Glu Phe Tyr Trp Ala Ala Cys Glu Leu
530                 535                 540 tat gta aca aca gga aaa gac gaa tat aag aat tac ctg atg aat tca        1680
Tyr Val Thr Thr Gly Lys Asp Glu Tyr Lys Asn Tyr Leu Met Asn Ser
545                 550                 555                 560 cct cac tat ctt gaa atg cct gca aag atg ggt gaa aac ggt gga gca        1728
Pro His Tyr Leu Glu Met Pro Ala Lys Met Gly Glu Asn Gly Gly Ala
            565                 570                 575 aac gga gaa gac aac gga ttg tgg gga tgc ttc acc tgg gga act act        1776
Asn Gly Glu Asp Asn Gly Leu Trp Gly Cys Phe Thr Trp Gly Thr Thr
                580                 585                 590 caa gga ttg gga acc att act ctt gca ttg gtt gaa aac gga ttg cct        1824
Gln Gly Leu Gly Thr Ile Thr Leu Ala Leu Val Glu Asn Gly Leu Pro
            595                 600                 605 gct aca gac att caa aag gca aga aac aat ata gct aaa gct gct gac        1872
Ala Thr Asp Ile Gln Lys Ala Arg Asn Asn Ile Ala Lys Ala Ala Asp
610                 615                 620 aga tgg ctt gag aat att gaa gag caa ggt tac aga ctg ccg atc aaa        1920
Arg Trp Leu Glu Asn Ile Glu Glu Gln Gly Tyr Arg Leu Pro Ile Lys
625                 630                 635                 640 cag gcg gag gat gag aga ggc ggt tat cca tgg ggt tca aac tcc ttc        1968
Gln Ala Glu Asp Glu Arg Gly Gly Tyr Pro Trp Gly Ser Asn Ser Phe
            645                 650                 655 att ttg aac cag atg ata gtt atg gga tat gcc tat gac ttt aca ggt        2016
Ile Leu Asn Gln Met Ile Val Met Gly Tyr Ala Tyr Asp Phe Thr Gly
                660                 665                 670 gac tcc aaa tat ctc gat gga atg ttt gac ggc ata agc tac ctg ttg        2064
Asp Ser Lys Tyr Leu Asp Gly Met Phe Asp Gly Ile Ser Tyr Leu Leu
            675                 680                 685 gga aga aac gca atg gat cag tcc tat gta aca ggg tat ggt gag cgt        2112
Gly Arg Asn Ala Met Asp Gln Ser Tyr Val Thr Gly Tyr Gly Glu Arg
690                 695                 700 ccg ctt cag aat cct cat gac agg ttc tgg acg ccg cag aca agt aag        2160
Pro Leu Gln Asn Pro His Asp Arg Phe Trp Thr Pro Gln Thr Ser Lys
705                 710                 715                 720 aga ttc cct gct cca cct ccg ggt ata att tcc ggc ggt ccg aac tcc        2208
Arg Phe Pro Ala Pro Pro Pro Gly Ile Ile Ser Gly Gly Pro Asn Ser
            725                 730                 735 cgt ttc gag gac ccg aca ata aat gcg gcc gtt aag aag gat aca ccg        2256
Arg Phe Glu Asp Pro Thr Ile Asn Ala Ala Val Lys Lys Asp Thr Pro
                740                 745                 750 cca cag aaa tgt ttt atc gac cat aca gac tca tgg tca acc aac gag        2304
Pro Gln Lys Cys Phe Ile Asp His Thr Asp Ser Trp Ser Thr Asn Glu
            755                 760                 765 ata act gtt aac tgg aat gct ccg ttt gca tgg gtt aca gct tat ctt        2352
Ile Thr Val Asn Trp Asn Ala Pro Phe Ala Trp Val Thr Ala Tyr Leu
770                 775                 780 gac gag cag tac aca gac agt gaa acc gat aca cca aca ccg aca gcg        2400
Asp Glu Gln Tyr Thr Asp Ser Glu Thr Asp Thr Pro Thr Pro Thr Ala
785                 790                 795                 800 aca cca gca ccg aca gtg aca ccg aca cct aca cca gca cca act cca        2448
Thr Pro Ala Pro Thr Val Thr Pro Thr Pro Thr Pro Ala Pro Thr Pro
            805                 810                 815
```

| | | |
|---|---|---|
| acc ccg aca cca aca cca act gct aca cca aca cca acg cca aca cca<br>Thr Pro Thr Pro Thr Pro Thr Ala Thr Pro Thr Pro Thr Pro Thr Pro<br>    820              825              830 | 2496 |
| acc cca acc gcg aca cca aca gta aca gca aca cca aca ccg acg ccg<br>Thr Pro Thr Ala Thr Pro Thr Val Thr Ala Thr Pro Thr Pro Thr Pro<br>835              840              845 | 2544 |
| agc agc aca ccg gta aaa gta cag tat ttg tgc gaa aat acg caa aca<br>Ser Ser Thr Pro Val Lys Val Gln Tyr Leu Cys Glu Asn Thr Gln Thr<br>850              855              860 | 2592 |
| tcc act cag gaa atc aag ggt aaa ttc aat ata gtt aac aca gga aac<br>Ser Thr Gln Glu Ile Lys Gly Lys Phe Asn Ile Val Asn Thr Gly Asn<br>865              870              875              880 | 2640 |
| aga gat tat tcg ctg aaa gat ata gta tta aga tac tac ttt acc aag<br>Arg Asp Tyr Ser Leu Lys Asp Ile Val Leu Arg Tyr Tyr Phe Thr Lys<br>            885              890              895 | 2688 |
| gag cac aat tca cag ctt cag ttt atc tgc tat tat aca ccc ata ggc<br>Glu His Asn Ser Gln Leu Gln Phe Ile Cys Tyr Tyr Thr Pro Ile Gly<br>        900              905              910 | 2736 |
| tcc gga aat ctc att ccg tcc ttt ggc ggc tcg ggt gac gag cat tat<br>Ser Gly Asn Leu Ile Pro Ser Phe Gly Gly Ser Gly Asp Glu His Tyr<br>        915              920              925 | 2784 |
| ctg cag ctg gaa ttc aaa gat gtc aag ctg cct gcc ggc ggt cag act<br>Leu Gln Leu Glu Phe Lys Asp Val Lys Leu Pro Ala Gly Gly Gln Thr<br>930              935              940 | 2832 |
| ggg gaa ata cag ttt gtt ata aga tat gca gat aac tcc ttc cat gat<br>Gly Glu Ile Gln Phe Val Ile Arg Tyr Ala Asp Asn Ser Phe His Asp<br>945              950              955              960 | 2880 |
| cag tcg aac gac tat tcg ttc gat cca act ata aaa gcg ttc cag gat<br>Gln Ser Asn Asp Tyr Ser Phe Asp Pro Thr Ile Lys Ala Phe Gln Asp<br>            965              970              975 | 2928 |
| tat ggc aag gtt acc ctg tat aag aat gga gaa ctt gtt tgg gga acg<br>Tyr Gly Lys Val Thr Leu Tyr Lys Asn Gly Glu Leu Val Trp Gly Thr<br>        980              985              990 | 2976 |
| ccg ccg ggc ggt aca gaa cct gaa  gaa ccg gaa gag cct  gcg ata gtt<br>Pro Pro Gly Gly Thr Glu Pro Glu  Glu Pro Glu Glu Pro  Ala Ile Val<br>        995              1000              1005 | 3024 |
| tac ggc  gac tgt aat gat gac  ggc aaa gta aat tca  aca gac gtc<br>Tyr Gly  Asp Cys Asn Asp Asp  Gly Lys Val Asn Ser   Thr Asp Val<br>    1010              1015              1020 | 3069 |
| gca gta  atg aag aga tat tta  aag aaa gaa aat gtt  aat att aat<br>Ala Val  Met Lys Arg Tyr Leu  Lys Lys Glu Asn Val   Asn Ile Asn<br>    1025              1030              1035 | 3114 |
| ctt gac  aat gca gat gtg aat  gcg gac ggc aaa gtt  aac tca aca<br>Leu Asp  Asn Ala Asp Val Asn  Ala Asp Gly Lys Val   Asn Ser Thr<br>    1040              1045              1050 | 3159 |
| gac ttc tca ata ctt aag aga tat gtt atg aag aac  ata gaa gaa<br>Asp Phe Ser Ile Leu Lys Arg Tyr Val Met Lys Asn  Ile Glu Glu<br>    1055              1060              1065 | 3204 |
| ttg cca tat cga<br>Leu Pro Tyr Arg<br>    1070 | 3216 |

<210> SEQ ID NO 6
<211> LENGTH: 1072
<212> TYPE: PRT
<213> ORGANISM: Artificial Sequence
<220> FEATURE:
<223> OTHER INFORMATION: Synthetic Construct

<400> SEQUENCE: 6

Leu Glu Asp Asn Ser Ser Thr Leu Pro Pro Tyr Lys Asn Asp Leu Leu

```
1               5                   10                  15
Tyr Glu Arg Thr Phe Asp Glu Gly Leu Cys Tyr Pro Trp His Thr Cys
                20                  25                  30
Glu Asp Ser Gly Gly Lys Cys Ser Phe Asp Val Val Asp Val Pro Gly
            35                  40                  45
Gln Pro Gly Asn Lys Ala Phe Ala Val Thr Val Leu Asp Lys Gly Gln
        50                  55                  60
Asn Arg Trp Ser Val Gln Met Arg His Arg Gly Leu Thr Leu Glu Gln
65                  70                  75                  80
Gly His Thr Tyr Arg Val Arg Leu Lys Ile Trp Ala Asp Ala Ser Cys
                85                  90                  95
Lys Val Tyr Ile Lys Ile Gly Gln Met Gly Glu Pro Tyr Ala Glu Tyr
            100                 105                 110
Trp Asn Asn Lys Trp Ser Pro Tyr Thr Leu Thr Ala Gly Lys Val Leu
        115                 120                 125
Glu Ile Asp Glu Thr Phe Val Met Asp Lys Pro Thr Asp Asp Thr Cys
        130                 135                 140
Glu Phe Thr Phe His Leu Gly Gly Glu Leu Ala Ala Thr Pro Pro Tyr
145                 150                 155                 160
Thr Val Tyr Leu Asp Asp Val Ser Leu Tyr Asp Pro Glu Tyr Thr Lys
                165                 170                 175
Pro Val Glu Tyr Ile Leu Pro Gln Pro Asp Val Arg Val Asn Gln Val
            180                 185                 190
Gly Tyr Leu Pro Glu Gly Lys Lys Val Ala Thr Val Val Cys Asn Ser
        195                 200                 205
Thr Gln Pro Val Lys Trp Gln Leu Lys Asn Ala Ala Gly Val Val Val
        210                 215                 220
Leu Glu Gly Tyr Thr Glu Pro Lys Gly Leu Asp Lys Asp Ser Gln Asp
225                 230                 235                 240
Tyr Val His Trp Leu Asp Phe Ser Asp Phe Ala Thr Glu Gly Ile Gly
                245                 250                 255
Tyr Tyr Phe Glu Leu Pro Thr Val Asn Ser Pro Thr Asn Tyr Ser His
            260                 265                 270
Pro Phe Asp Ile Arg Lys Asp Ile Tyr Thr Gln Met Lys Tyr Asp Ala
        275                 280                 285
Leu Ala Phe Phe Tyr His Lys Arg Ser Gly Ile Pro Ile Glu Met Pro
        290                 295                 300
Tyr Ala Gly Gly Glu Gln Trp Thr Arg Pro Ala Gly His Ile Gly Ile
305                 310                 315                 320
Glu Pro Asn Lys Gly Asp Thr Asn Val Pro Thr Trp Pro Gln Asp Asp
                325                 330                 335
Glu Tyr Ala Gly Ile Pro Gln Lys Asn Tyr Thr Lys Asp Val Thr Gly
            340                 345                 350
Gly Trp Tyr Asp Ala Gly Asp His Gly Lys Tyr Val Val Asn Gly Gly
        355                 360                 365
Ile Ala Val Trp Thr Leu Met Asn Met Tyr Glu Arg Ala Lys Ile Arg
        370                 375                 380
Gly Leu Asp Asn Trp Gly Pro Tyr Arg Asp Gly Gly Met Asn Ile Pro
385                 390                 395                 400
Glu Gln Asn Asn Gly Tyr Pro Asp Ile Leu Asp Glu Ala Arg Trp Glu
                405                 410                 415
Ile Glu Phe Phe Lys Lys Met Gln Val Thr Glu Lys Glu Asp Pro Ser
            420                 425                 430
```

```
Ile Ala Gly Met Val His His Lys Ile His Asp Phe Arg Trp Thr Ala
            435                 440                 445
Leu Gly Met Leu Pro His Glu Asp Pro Gln Pro Arg Tyr Leu Arg Pro
        450                 455                 460
Val Ser Thr Ala Ala Thr Leu Asn Phe Ala Ala Thr Leu Ala Gln Ser
465                 470                 475                 480
Ala Arg Leu Trp Lys Asp Tyr Asp Pro Thr Phe Ala Ala Asp Cys Leu
                485                 490                 495
Glu Lys Ala Glu Ile Ala Trp Gln Ala Ala Leu Lys His Pro Asp Ile
            500                 505                 510
Tyr Ala Glu Tyr Thr Pro Gly Ser Gly Pro Gly Gly Gly Pro Tyr
        515                 520                 525
Asn Asp Asp Tyr Val Gly Asp Glu Phe Tyr Trp Ala Ala Cys Glu Leu
            530                 535                 540
Tyr Val Thr Thr Gly Lys Asp Glu Tyr Lys Asn Tyr Leu Met Asn Ser
545                 550                 555                 560
Pro His Tyr Leu Glu Met Pro Ala Lys Met Gly Glu Asn Gly Gly Ala
                565                 570                 575
Asn Gly Glu Asp Asn Gly Leu Trp Gly Cys Phe Thr Trp Gly Thr Thr
                580                 585                 590
Gln Gly Leu Gly Thr Ile Thr Leu Ala Leu Val Glu Asn Gly Leu Pro
        595                 600                 605
Ala Thr Asp Ile Gln Lys Ala Arg Asn Asn Ile Ala Lys Ala Ala Asp
610                 615                 620
Arg Trp Leu Glu Asn Ile Glu Glu Gln Gly Tyr Arg Leu Pro Ile Lys
625                 630                 635                 640
Gln Ala Glu Asp Glu Arg Gly Gly Tyr Pro Trp Gly Ser Asn Ser Phe
                645                 650                 655
Ile Leu Asn Gln Met Ile Val Met Gly Tyr Ala Tyr Asp Phe Thr Gly
                660                 665                 670
Asp Ser Lys Tyr Leu Asp Gly Met Phe Asp Gly Ile Ser Tyr Leu Leu
        675                 680                 685
Gly Arg Asn Ala Met Asp Gln Ser Tyr Val Thr Gly Tyr Gly Glu Arg
        690                 695                 700
Pro Leu Gln Asn Pro His Asp Arg Phe Trp Thr Pro Gln Thr Ser Lys
705                 710                 715                 720
Arg Phe Pro Ala Pro Pro Gly Ile Ser Gly Gly Pro Asn Ser
                725                 730                 735
Arg Phe Glu Asp Pro Thr Ile Asn Ala Ala Val Lys Lys Asp Thr Pro
                740                 745                 750
Pro Gln Lys Cys Phe Ile Asp His Thr Asp Ser Trp Ser Thr Asn Glu
            755                 760                 765
Ile Thr Val Asn Trp Asn Ala Pro Phe Ala Trp Val Thr Ala Tyr Leu
        770                 775                 780
Asp Glu Gln Tyr Thr Asp Ser Glu Thr Asp Thr Pro Thr Pro Thr Ala
785                 790                 795                 800
Thr Pro Ala Pro Thr Val Thr Pro Thr Pro Thr Ala Pro Thr Pro
                805                 810                 815
Thr Pro Thr Pro Thr Pro Thr Ala Thr Pro Thr Pro Thr Pro Thr Pro
            820                 825                 830
Thr Pro Thr Ala Thr Pro Thr Val Thr Ala Thr Pro Thr Pro Thr Pro
                835                 840                 845
```

```
Ser Ser Thr Pro Val Lys Val Gln Tyr Leu Cys Glu Asn Thr Gln Thr
    850             855             860

Ser Thr Gln Glu Ile Lys Gly Lys Phe Asn Ile Val Asn Thr Gly Asn
865             870             875             880

Arg Asp Tyr Ser Leu Lys Asp Ile Val Leu Arg Tyr Tyr Phe Thr Lys
            885             890             895

Glu His Asn Ser Gln Leu Gln Phe Ile Cys Tyr Tyr Thr Pro Ile Gly
        900             905             910

Ser Gly Asn Leu Ile Pro Ser Phe Gly Gly Ser Gly Asp Glu His Tyr
    915             920             925

Leu Gln Leu Glu Phe Lys Asp Val Lys Leu Pro Ala Gly Gly Gln Thr
930             935             940

Gly Glu Ile Gln Phe Val Ile Arg Tyr Ala Asp Asn Ser Phe His Asp
945             950             955             960

Gln Ser Asn Asp Tyr Ser Phe Asp Pro Thr Ile Lys Ala Phe Gln Asp
            965             970             975

Tyr Gly Lys Val Thr Leu Tyr Lys Asn Gly Glu Leu Val Trp Gly Thr
        980             985             990

Pro Pro Gly Gly Thr Glu Pro Glu  Glu Pro Glu Glu Pro  Ala Ile Val
    995             1000            1005

Tyr Gly  Asp Cys Asn Asp  Asp Gly Lys Val Asn Ser  Thr Asp Val
    1010            1015            1020

Ala Val Met Lys Arg Tyr Leu  Lys Lys Glu Asn Val  Asn Ile Asn
    1025            1030            1035

Leu Asp Asn Ala Asp Val Asn  Ala Asp Gly Lys Val  Asn Ser Thr
    1040            1045            1050

Asp Phe Ser Ile Leu Lys Arg  Tyr Val Met Lys Asn  Ile Glu Glu
    1055            1060            1065

Leu Pro  Tyr Arg
    1070

<210> SEQ ID NO 7
<211> LENGTH: 174
<212> TYPE: DNA
<213> ORGANISM: Caldicellulosiruptor bescii
<220> FEATURE:
<221> NAME/KEY: CDS
<222> LOCATION: (1)..(174)

<400> SEQUENCE: 7 aca cca aca ccg aca gcg aca cca gca ccg aca gtg aca ccg aca cct       48
Thr Pro Thr Pro Thr Ala Thr Pro Ala Pro Thr Val Thr Pro Thr Pro
1               5                   10                  15 aca cca gca cca act cca acc ccg aca cca aca cca act gct aca cca       96
Thr Pro Ala Pro Thr Pro Thr Pro Thr Pro Thr Pro Thr Ala Thr Pro
            20                  25                  30 aca cca acg cca aca cca acc cca acc gcg aca cca aca gta aca gca      144
Thr Pro Thr Pro Thr Pro Thr Pro Thr Ala Thr Pro Thr Val Thr Ala
        35                  40                  45 aca cca aca ccg acg ccg agc agc aca ccg                              174
Thr Pro Thr Pro Thr Pro Ser Ser Thr Pro
    50                  55

<210> SEQ ID NO 8
<211> LENGTH: 58
<212> TYPE: PRT
<213> ORGANISM: Caldicellulosiruptor bescii

<400> SEQUENCE: 8
```

```
Thr Pro Thr Pro Thr Ala Thr Pro Ala Pro Thr Val Thr Pro Thr Pro
1               5                   10                  15

Thr Pro Ala Pro Thr Pro Thr Pro Thr Pro Thr Pro Thr Ala Thr Pro
            20              25              30

Thr Pro Thr Pro Thr Pro Thr Pro Thr Ala Thr Pro Thr Val Thr Ala
        35              40                  45

Thr Pro Thr Pro Thr Pro Ser Ser Thr Pro
        50              55

<210> SEQ ID NO 9
<211> LENGTH: 31
<212> TYPE: DNA
<213> ORGANISM: Artificial Sequence
<220> FEATURE:
<223> OTHER INFORMATION: PCR Primer

<400> SEQUENCE: 9
acagcagcta gcgccgtcga cagcaacaac g                                31

<210> SEQ ID NO 10
<211> LENGTH: 33
<212> TYPE: DNA
<213> ORGANISM: Artificial Sequence
<220> FEATURE:
<223> OTHER INFORMATION: PCR Primer

<400> SEQUENCE: 10
tgttgactcg agggtggtgt gcggcagttt gtc                              33

<210> SEQ ID NO 11
<211> LENGTH: 30
<212> TYPE: DNA
<213> ORGANISM: Artificial Sequence
<220> FEATURE:
<223> OTHER INFORMATION: PCR Primer

<400> SEQUENCE: 11
acagcactcg aggccgtcga cagcaacaac                                  30

<210> SEQ ID NO 12
<211> LENGTH: 32
<212> TYPE: DNA
<213> ORGANISM: Artificial Sequence
<220> FEATURE:
<223> OTHER INFORMATION: PCR Primer

<400> SEQUENCE: 12
ctgtgtccat ggcaggtgtg cctttttaaca ca                              32

<210> SEQ ID NO 13
<211> LENGTH: 32
<212> TYPE: DNA
<213> ORGANISM: Artificial Sequence
<220> FEATURE:
<223> OTHER INFORMATION: PCR Primer

<400> SEQUENCE: 13
cccattctcg agataaggta ggtgggggtat gc                              32

<210> SEQ ID NO 14
<211> LENGTH: 29
<212> TYPE: DNA
<213> ORGANISM: Artificial Sequence
<220> FEATURE:
```

```
<223> OTHER INFORMATION: PCR Primer

<400> SEQUENCE: 14
actgtgctcg aggcaggtgt gccttttaa                                         29

<210> SEQ ID NO 15
<211> LENGTH: 32
<212> TYPE: DNA
<213> ORGANISM: Artificial Sequence
<220> FEATURE:
<223> OTHER INFORMATION: PCR Primer

<400> SEQUENCE: 15
ctgtttccat ggcagactat aactatggag aa                                     32

<210> SEQ ID NO 16
<211> LENGTH: 32
<212> TYPE: DNA
<213> ORGANISM: Artificial Sequence
<220> FEATURE:
<223> OTHER INFORMATION: PCR Primer

<400> SEQUENCE: 16
acgatactcg agtgaatttc cgggtatggt tg                                     32

<210> SEQ ID NO 17
<211> LENGTH: 31
<212> TYPE: DNA
<213> ORGANISM: Artificial Sequence
<220> FEATURE:
<223> OTHER INFORMATION: PCR Primer

<400> SEQUENCE: 17
cctgttctcg aggcagacta taactatgga g                                      31

<210> SEQ ID NO 18
<211> LENGTH: 31
<212> TYPE: DNA
<213> ORGANISM: Artificial Sequence
<220> FEATURE:
<223> OTHER INFORMATION: PCR Primer

<400> SEQUENCE: 18
actgcactcg agggtcctac aaaggcacct a                                      31

<210> SEQ ID NO 19
<211> LENGTH: 36
<212> TYPE: DNA
<213> ORGANISM: Artificial Sequence
<220> FEATURE:
<223> OTHER INFORMATION: PCR Primer

<400> SEQUENCE: 19
atcagttttg ctcgaggttc ttgtacggca atgtat                                 36

<210> SEQ ID NO 20
<211> LENGTH: 32
<212> TYPE: DNA
<213> ORGANISM: Artificial Sequence
<220> FEATURE:
<223> OTHER INFORMATION: PCR Primer

<400> SEQUENCE: 20
agctttctcg agtccagaca atcatccaat tc                                     32
```

```
<210> SEQ ID NO 21
<211> LENGTH: 32
<212> TYPE: DNA
<213> ORGANISM: Artificial Sequence
<220> FEATURE:
<223> OTHER INFORMATION: PCR Primer

<400> SEQUENCE: 21
agtttcctcg agtgaattgc tgtcatcaga gt                                   32

<210> SEQ ID NO 22
<211> LENGTH: 33
<212> TYPE: DNA
<213> ORGANISM: Artificial Sequence
<220> FEATURE:
<223> OTHER INFORMATION: PCR Primer

<400> SEQUENCE: 22
tccgtgcata tgttagaaga taattcttcg act                                  33

<210> SEQ ID NO 23
<211> LENGTH: 33
<212> TYPE: DNA
<213> ORGANISM: Artificial Sequence
<220> FEATURE:
<223> OTHER INFORMATION: PCR Primer

<400> SEQUENCE: 23
cagattctcg agtcgatatg gcaattcttc tat                                  33
```

CHIMERIC ENZYMES WITH IMPROVED CELLULASE ACTIVITIES

CROSS-REFERENCE TO RELATED APPLICATIONS

This application claims priority to U.S. Provisional Application No. 61/671,454, filed Jul. 13, 2012, the contents of which are incorporated by reference in their entirety.

CONTRACTUAL ORIGIN

The United States Government has rights in this invention under Contract No. DE-AC36-08GO28308 between the United States Department of Energy and Alliance for Sustainable Energy, LLC, the Manager and Operator of the National Renewable Energy Laboratory.

REFERENCE TO SEQUENCE LISTING

This application contains a Sequence Listing submitted as an electronic text file entitled "12-33_ST25.txt," having a size in bytes of 100 kb and created on Jul. 12, 2013. Pursuant to 37 CFR §1.52(e)(5), the information contained in the above electronic file is hereby incorporated by reference in its entirety.

BACKGROUND

Biofuel is a promising renewable energy technology in part because of the large amount and low cost of its biomass feedstock. Efficient action of cellulases to release fermentable sugars from biomass cellulose is an important step in making this conversion economically viable. The major strategies to improve cellulase activity include rational design and directed evolution. Rational design is based on knowledge of the structure of cellulases, and presumes a detailed understanding of the relationship between enzyme structure and its function, but directed evolution does not require understanding of structure and function.

*Clostridium thermocellum* is an anaerobic, thermophilic, cellulolytic, and ethanogenic bacterium that shows potential for use in bioenergy production because it is capable of directly converting cellulose into ethanol. Degradation of cellulosic materials by *Clostridium thermocellum* is carried out by a large extracellular cellulase system called the cellulosome, a complicated protein complex consisting of nearly 20 different catalytic subunits. One feature of the cellulosome is the nonhydrolytic scaffoldin subunit that integrates the various catalytic subunits into the complex via interactions between its repetitive cohesin domains and complementary dockerin domains on the catalytic subunits. Several cellulolytic bacteria and fungi are known to produce extracellular multienzyme complexes similar to the cellulosome.

The foregoing examples of the related art and limitations related therewith are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods that are meant to be exemplary and illustrative, not limiting in scope. In various embodiments, one or more of the above-described problems have been reduced or eliminated, while other embodiments are directed to other improvements.

Exemplary embodiments provide isolated nucleic acid molecules that encode chimeric CbhA polypeptides that have cellulase activities greater than wild-type CbhA polypeptides. In certain embodiments, the chimeric CbhA polypeptides comprise domains from *Clostridium thermocellum* CbhA and *Caldicellulosiruptor bescii* CelA polypeptides, such as the linker domain from the *Caldicellulosiruptor bescii* CelA polypeptide.

Additional embodiments provide chimeric CbhA polypeptides that have cellulase activities at least 2-fold greater than wild-type CbhA polypeptides and methods for degrading cellulose or lignocellulosic biomass by contacting a cellulose containing material or lignocellulosic biomass with the isolated chimeric CbhA polypeptides.

In addition to the exemplary aspects and embodiments described above, further aspects and embodiments will become apparent by reference to the drawings and by study of the following descriptions.

BRIEF DESCRIPTION OF THE DRAWINGS

Exemplary embodiments are illustrated in referenced figures of the drawings. It is intended that the embodiments and figures disclosed herein are to be considered illustrative rather than limiting.

FIG. 1 shows the nucleic acid sequence for wild-type CbhA from *Clostridium thermocellum* (SEQ ID NO:1).

FIG. 2 shows the amino acid sequence for wild-type CbhA from *Clostridium thermocellum* (SEQ ID NO:2). The putative signal sequence is indicated in bold and the linker domain is underlined.

FIG. 3 shows the nucleic acid sequence for wild-type CelA from *Caldicellulosiruptor bescii* (SEQ ID NO:3).

FIG. 4 shows the amino acid sequence for wild-type CelA from *Caldicellulosiruptor bescii* (SEQ ID NO:4). The linker domain is underlined.

FIG. 5 shows the nucleic acid (A; SEQ ID NO:5) amino acid (B; SEQ ID NO:6) sequence for a chimeric CbhA polypeptide wherein the linker domain from CbhA has been replaced with the linker from *Caldicellulosiruptor bescii* CelA. The linker domain is underlined in each sequence and the nucleic acid (C; SEQ ID NO:7) and amino acid (D; SEQ ID NO:8) sequence of the linker domain are also provided.

FIG. 6A shows details of three exemplary linkers for the construction of chimeric enzymes. SP, signal peptide; Coh, type-II cohesin; Doc 1, type-I dockerin; Doc 2, type-II dockerin; GH, glycosyl hydrolase family; CBM, family of carbohydrate-binding modules; Ig, immunoglobulin-like fold; X, family of unknown function. FIG. 6B illustrates the domains of the three proteins that contain the linkers.

FIG. 8 shows the contribution of linkers to activity of CbhA and its chimeras. A, activity of cellulosomal cellulase was assayed directly; B, cellulosomal cellulase was combined with monoscaffoldin of cohesin2-CBM3a to generate minicellulosome first, and then its activity was assayed.

DETAILED DESCRIPTION

Figure 7:
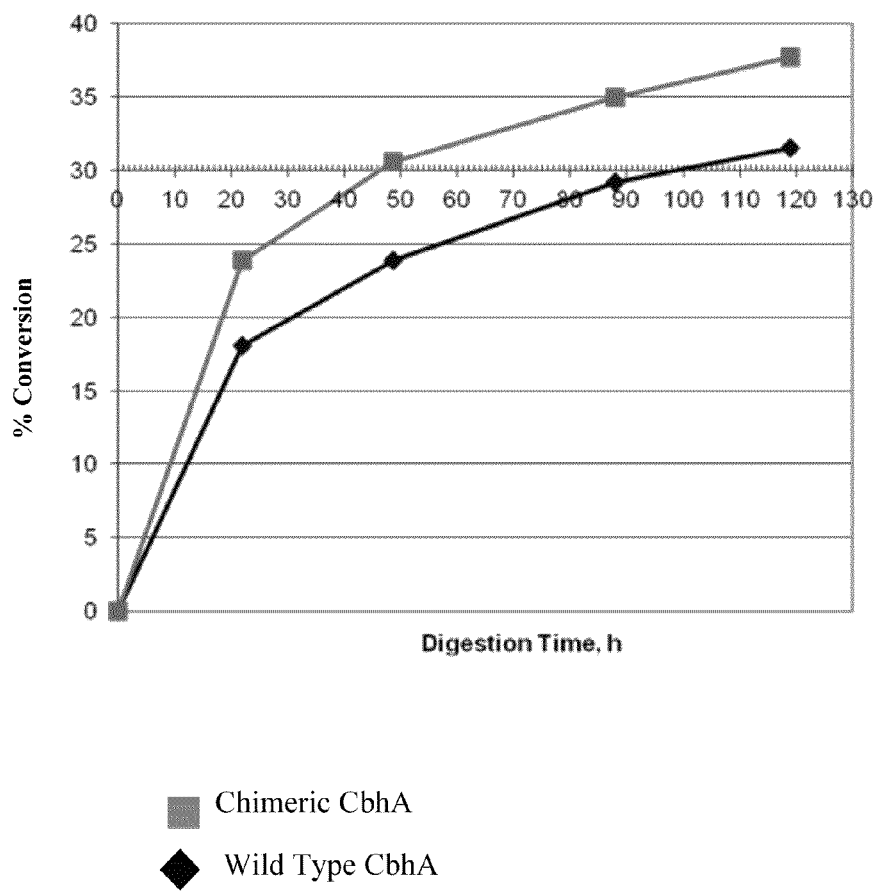
FIG. 7 shows digestion curves for chimeric and wild-type CbhA enzymes on pretreated corn stover substrates.

Nucleic acid molecules encoding chimeric cellulase polypeptides that exhibit improved cellulase activities are disclosed herein. The chimeric cellulase polypeptides encoded by these nucleic acids and methods to produce the cellulases are also described, along with methods of using chimeric cellulases for the conversion of cellulose to sugars such as glucose.

Despite efforts to engineer cellulases with significantly improved activities, few successes have been demonstrated. The results of past efforts have been summarized, for example, in a review article by Wilson (*Curr. Opin. Biotechnol.* 20:295-299 (2009) (noting that "[a]t this time there are no published reports of engineered cellulases with major (greater than 1.5-fold) increases in activity on crystalline cellulose."). Prior cellulase engineering has focused upon screening small sets of rationally guided mutations for higher thermal stability and subsequent modest gains in activity at higher conversion temperatures. Significant activity improvement in processive cellulase enzymes on realistic substrates at industrially relevant enzyme loadings and substrate conversion levels remains to be demonstrated.

Disclosed herein are methods for dramatically improving the activity of cellulosomal cellulases (e.g., *C. thermocellum* CbhA) by exchanging domains with other cellulases to form chimeric polypeptides. In particular, exchanging linker domains in the chimeric polypeptides results in a surprising increase in cellulase activity when compared with the wild-type polypeptides.

CbhA is one of the key cellulosomal cellulases in the *C. thermocellum* cellulosome system. The nucleic acid (SEQ ID NO:1) and amino acid (SEQ ID NO:2) sequences for wild type CbhA are depicted in FIGS. 1 and 2, respectively.

The improvements in activity exhibited in chimeras by substituting the long linker from *C. bescii* CelA demonstrates the potential of this new approach exploiting modular cooperation to enhance activity of a large cellulosomal cellulase, but also supports applying this new approach to improvement of other multimodular cellulases. The high activity and high intramolecular synergy displayed by the chimeric cellulases also demonstrates the promise of enhancing the activity of cellulases (and possibly also that of metabolic enzymes related to biomass conversion) by linking catalytic domains not combined in nature.

The activity enhancement in the chimeras of CbhA and in other artificial multifunctional cellulases may reflect the differing abilities of the linkers to provide the spacing and the flexibility that allow individual modules of the multifunctional peptide to interact productively with the cellulose surface.

Various linkers have been found in cellulases and cellulosomal components such as scaffoldins, the major composition being "PT" or "G" repeats based on their amino acid sequences. It has been suggested that these linkers do not typically form defined structures. Their function may include increasing the solubility of peptides due to glycosylation on the amino acid of "T", and making the peptide flexible. The supramolecular cellulosome protein complex keeps many cellulases together, and while it seems that so highly organized a complex would limit the mobility of tethered cellulases, the cellulosome has extremely high activity on insoluble and recalcitrant crystalline cellulose. Having linkers between modules and between peptides may make the attached catalytic modules flexible, resulting in greater mobility of cellulases on insoluble substrates.

What is referred to herein as the "linker domain" of CbhA is two consecutive X1 domains of CbhA. The X1 module may have disruption function in the digestion of crystalline cellulose, but these two X1 domains may also form a spacer or linker in the large peptide. Substituting a large linker of *C. bescii* CelA for two X1 domains in CbhA resulted in a chimera that was more stable when expressed in *E. coli*, and exhibited a higher activity than that of wild-type CbhA.

Compared to linkers with "PT" or "G" compositions, linker 3 showed normal amino acid composition, and was very stable in CbhA or truncated CbhA, as well as in artificial multifunctional cellulases. This linker is not easily digested or broken during its overexpression in *E. coli*t, or in storage buffers. Therefore, it is expected that this linker could be used widely in the construction of multifunctional cellulases, and furthermore it could be used for construction of multifunctional metabolic enzymes to this module has been used to construct multifunctional cellulases, and obtain high intramolecular synergy.

As used herein, the terms "chimeric polypeptide" or "chimera" refer to a polypeptide composed of parts of different wild-type polypeptides and typically composed of discrete functional domains from different polypeptides. For example, a chimeric CbhA polypeptide may comprise a linker domain from a distinct polypeptide. For exemplary purposes, the present disclosure is directed to chimeric *C. thermocellum* CbhA polypeptides comprising a linker domain from the CelA polypeptide of *C. bescii*, such as those depicted in FIG. 5 and represented by SEQ ID NOS:5 and 6. However, the concepts disclosed herein encompass chimeras of CbhA or CelA polypeptides from other bacteria that exhibit enhanced enzymatic activities. The amino acid sequences for the wild-type *C. thermocellum* CbhA (SEQ ID NO:2) and *C. bescii* CelA (SEQ ID NO:4) polypeptides and the linker domains of each are illustrated in FIGS. 2 and 4, respectively.

In some embodiments, the chimeras may further comprise one or more binding adaptors bound to the chimeric polypeptide. Binding adaptors may comprise a fusion of a cohesion molecule with a carbohydrate binding module (CBM). One exemplary binding adaptor comprises a fusion of cohesin 2 (the second of the nine Type-I cohesins in the *C. thermocellum* scaffoldin protein CipA) with a with a CBM3a module. However, other cohesions and CBMs are also suitable.

The chimeric CbhA polypeptides exhibit surprisingly improved cellulase activities when compared to the wild-type CbhA polypeptides. The term "improved cellulase activity" refers to an increased rate of hydrolysis of a cellulosic substrate. Relative activities for chimeric and wild-type CbhA polypeptides can be determined using conventional assays, including those discussed in the Examples below. Additional assays suitable for determining cellulase activity include hydrolysis assays on industrially relevant cellulose-containing substrates such as pretreated corn stover. Hydrolysis assays on crystalline cellulose or amorphous cellulose or on small molecule fluorescent reporters may also be used to determine cellulase activity. In certain embodiments, cellulase activity is expressed as the amount of time or enzyme concentration needed to reach a certain percentage (e.g., 30%) of cellulose conversion to sugars. For example, as shown in FIG. 7, the digestion times to achieve 30% conversion of a pretreated corn stover cellulose substrate are approximately 46.4 hours for the chimeric CbhA and 98.4 hours for the wild-type CbhA. In this assay, the chimeric CbhA exhibits a 2.12-fold greater cellulase activity than the wild-type CbhA.

In contrast to the results of previous attempts to engineer cellulases, the chimeric CbhA polypeptides herein exhibit cellulase activities that are at least 1.5-fold greater than the wild-type CbhA polypeptide and that can reach at least 3-fold greater activity. In certain embodiments, the chimeric CbhA polypeptides exhibit cellulase activities that are at least 1.1-, 1.2-, 1.3-, 1.4-, 1.5-, 1.6-, 1.7-, 1.8-, 1.9-, 2-, 2.1-, 2.2-, 2.3-, 2.4-, 2.5-, 2.6-, 2.7-, 2.8-, 2.9-, 3-, 3.1-, 3.2-, 3.3-, 3.4-, or 3.5-fold greater than the wild-type CbhA polypeptide.

"Nucleic acid" or "polynucleotide" as used herein refers to purine- and pyrimidine-containing polymers of any length, either polyribonucleotides or polydeoxyribonucleotide or mixed polyribo-polydeoxyribonucleotides. This includes single- and double-stranded molecules (i.e., DNA-DNA, DNA-RNA and RNA-RNA hybrids) as well as "protein nucleic acids" (PNA) formed by conjugating bases to an amino acid backbone. This also includes nucleic acids containing modified bases.

Nucleic acids referred to herein as "isolated" are nucleic acids that have been removed from their natural milieu or separated away from the nucleic acids of the genomic DNA or cellular RNA of their source of origin (e.g., as it exists in cells or in a mixture of nucleic acids such as a library), and may have undergone further processing. Isolated nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids that are isolated.

Nucleic acids referred to herein as "recombinant" are nucleic acids which have been produced by recombinant DNA methodology, including those nucleic acids that are generated by procedures that rely upon a method of artificial replication, such as the polymerase chain reaction (PCR) and/or cloning into a vector using restriction enzymes. Recombinant nucleic acids also include those that result from recombination events that occur through the natural mechanisms of cells, but are selected for after the introduction to the cells of nucleic acids designed to allow or make probable a desired recombination event. Portions of isolated nucleic acids that code for polypeptides having a certain function can be identified and isolated by, for example, the method disclosed in U.S. Pat. No. 4,952,501.

An isolated nucleic acid molecule can be isolated from its natural source or produced using recombinant DNA technology (e.g., polymerase chain reaction (PCR) amplification, cloning) or chemical synthesis. Isolated nucleic acid molecules can include, for example, genes, natural allelic variants of genes, coding regions or portions thereof, and coding and/or regulatory regions modified by nucleotide insertions, deletions, substitutions, and/or inversions in a manner such that the modifications do not substantially interfere with the nucleic acid molecule's ability to encode a polypeptide or to form stable hybrids under stringent conditions with natural gene isolates. An isolated nucleic acid molecule can include degeneracies. As used herein, nucleotide degeneracy refers to the phenomenon that one amino acid can be encoded by different nucleotide codons. Thus, the nucleic acid sequence of a nucleic acid molecule that encodes a protein or polypeptide can vary due to degeneracies.

Unless so specified, a nucleic acid molecule is not required to encode a protein having protein activity. A nucleic acid molecule can encode a truncated, mutated or inactive protein, for example. In addition, nucleic acid molecules may also be useful as probes and primers for the identification, isolation and/or purification of other nucleic acid molecules, independent of a protein-encoding function.

Suitable nucleic acids include fragments or variants that encode a functional cellulase. For example, a fragment can comprise the minimum nucleotides required to encode a functional cellulase. Nucleic acid variants include nucleic acids with one or more nucleotide additions, deletions, substitutions, including transitions and transversions, insertion, or modifications (e.g., via RNA or DNA analogs). Alterations may occur at the 5' or 3' terminal positions of the reference nucleotide sequence or anywhere between those terminal positions, interspersed either individually among the nucleotides in the reference sequence or in one or more contiguous groups within the reference sequence.

In certain embodiments, a nucleic acid may be identical to a sequence represented herein. In other embodiments, the nucleic acids may be at least about 80%, 81%, 82%, 83%, 84%, 85%, 86%, 87%, 88%, 89%, 90%, 91%, 92%, 93%, 94%, 95%, 96%, 97%, 98% or 99% identical to a sequence represented herein, or 80%, 81%, 82%, 83%, 84%, 85%, 86%, 87%, 88%, 89%, 90%, 91%, 92%, 93%, 94%, 95%, 96%, 97%, 98% or 99% identical to a sequence represented herein. Sequence identity calculations can be performed using computer programs, hybridization methods, or calculations. Exemplary computer program methods to determine identity and similarity between two sequences include, but are not limited to, the GCG program package, BLASTN, BLASTX, TBLASTX, and FASTA. The BLAST programs are publicly available from NCBI and other sources. For example, nucleotide sequence identity can be determined by comparing query sequences to sequences in publicly available sequence databases (NCBI) using the BLASTN2 algorithm.

Embodiments of the nucleic acids include those that encode a chimeric CbhA polypeptide that functions as a cellulase or functional equivalents thereof. The amino acid sequence of an exemplary chimeric CbhA polypeptide is depicted in FIG. 5 and represented by SEQ ID NO:6. A functional equivalent includes fragments or variants of these that exhibit the ability to function as a cellulase. As a result of the degeneracy of the genetic code, many nucleic acid sequences can encode a polypeptide having, for example, the amino acid sequence of SEQ ID NO:6. Such functionally equivalent variants are contemplated herein.

Altered or variant nucleic acids can be produced by one of skill in the art using the sequence data illustrated herein and standard techniques known in the art. Variant nucleic acids may be detected and isolated by hybridization under high stringency conditions or moderate stringency conditions, for example, which are chosen to prevent hybridization of nucleic acids having non-complementary sequences. "Stringency conditions" for hybridizations is a term of art that refers to the conditions of temperature and buffer concentration that permit hybridization of a particular nucleic acid to another nucleic acid in which the first nucleic acid may be perfectly complementary to the second, or the first and second may share some degree of complementarity that is less than perfect.

Nucleic acids may be derived from a variety of sources including DNA, cDNA, synthetic DNA, synthetic RNA, or combinations thereof. Such sequences may comprise genomic DNA, which may or may not include naturally occurring introns. Moreover, such genomic DNA may be obtained in association with promoter regions or poly (A) sequences. The sequences, genomic DNA, or cDNA may be obtained in any of several ways. Genomic DNA can be extracted and purified from suitable cells by means well known in the art. Alternatively, mRNA can be isolated from a cell and used to produce cDNA by reverse transcription or other means.

Oligonucleotides that are fragments of the nucleic acid sequences disclosed herein and antisense nucleic acids that are complementary, in whole or in part, to those sequences are contemplated herein. Oligonucleotides may be used as primers or probes or for any other use known in the art. Antisense nucleic acids may be used, for example, to inhibit gene expression when introduced into a cell or for any other use known in the art. Oligonucleotides and antisense nucleic acids can be produced by standard techniques known in the art.

Also disclosed herein are recombinant vectors, including expression vectors, containing nucleic acids encoding chimeric CbhA polypeptides. A "recombinant vector" is a nucleic acid molecule that is used as a tool for manipulating a nucleic acid sequence of choice or for introducing such a nucleic acid sequence into a host cell. A recombinant vector may be suitable for use in cloning, sequencing, or otherwise manipulating the nucleic acid sequence of choice, such as by expressing or delivering the nucleic acid sequence of choice into a host cell to form a recombinant cell. Such a vector typically contains heterologous nucleic acid sequences not naturally found adjacent to a nucleic acid sequence of choice, although the vector can also contain regulatory nucleic acid sequences (e.g., promoters, untranslated regions) that are naturally found adjacent to the nucleic acid sequences of choice or that are useful for expression of the nucleic acid molecules.

A recombinant vector can be either RNA or DNA, either prokaryotic or eukaryotic, and typically is a plasmid. The vector can be maintained as an extrachromosomal element (e.g., a plasmid) or it can be integrated into the chromosome of a recombinant host cell. The entire vector can remain in place within a host cell, or under certain conditions, the plasmid DNA can be deleted, leaving behind the nucleic acid molecule of choice. An integrated nucleic acid molecule can be under chromosomal promoter control, under native or plasmid promoter control, or under a combination of several promoter controls. Single or multiple copies of the nucleic acid molecule can be integrated into the chromosome. A recombinant vector can contain at least one selectable marker.

The term "expression vector" refers to a recombinant vector that is capable of directing the expression of a nucleic acid sequence that has been cloned into it after insertion into a host cell or other (e.g., cell-free) expression system. A nucleic acid sequence is "expressed" when it is transcribed to yield an mRNA sequence. In most cases, this transcript will be translated to yield an amino acid sequence. The cloned gene is usually placed under the control of (i.e., operably linked to) an expression control sequence. The phrase "operatively linked" refers to linking a nucleic acid molecule to an expression control sequence in a manner such that the molecule can be expressed when introduced (i.e., transformed, transduced, transfected, conjugated or conduced) into a host cell.

Recombinant vectors and expression vectors may contain one or more regulatory sequences or expression control sequences. Regulatory sequences broadly encompass expression control sequences (e.g., transcription control sequences or translation control sequences), as well as sequences that allow for vector replication in a host cell. Transcription control sequences are sequences that control the initiation, elongation, or termination of transcription. Suitable regulatory sequences include any sequence that can function in a host cell or organism into which the recombinant nucleic acid molecule is to be introduced, including those that control transcription initiation, such as promoter, enhancer, terminator, operator and repressor sequences. Additional regulatory sequences include translation regulatory sequences, origins of replication, and other regulatory sequences that are compatible with the recombinant cell. The expression vectors may contain elements that allow for constitutive expression or inducible expression of the protein or proteins of interest. Numerous inducible and constitutive expression systems are known in the art.

Typically, an expression vector includes at least one nucleic acid molecule encoding a chimeric CbhA polypeptide operatively linked to one or more expression control sequences (e.g., transcription control sequences or translation control sequences). In one aspect, an expression vector may comprise a nucleic acid encoding a chimeric CbhA polypeptide, as described herein, operably linked to at least one regulatory sequence. It should be understood that the design of the expression vector may depend on such factors as the choice of the host cell to be transformed and/or the type of polypeptide to be expressed.

Expression and recombinant vectors may contain a selectable marker, a gene encoding a protein necessary for survival or growth of a host cell transformed with the vector. The presence of this gene allows growth of only those host cells that express the vector when grown in the appropriate selective media. Typical selection genes encode proteins that confer resistance to antibiotics or other toxic substances, complement auxotrophic deficiencies, or supply critical nutrients not available from a particular media. Markers may be an inducible or non-inducible gene and will generally allow for positive selection. Non-limiting examples of selectable markers include the ampicillin resistance marker (i.e., beta-lactamase), tetracycline resistance marker, neomycin/kanamycin resistance marker (i.e., neomycin phosphotransferase), dihydrofolate reductase, glutamine synthetase, and the like. The choice of the proper selectable marker will depend on the host cell, and appropriate markers for different hosts as understood by those of skill in the art.

Suitable expression vectors may include (or may be derived from) plasmid vectors that are well known in the art, such as those commonly available from commercial sources. Examples include the pET expression vectors. Vectors can contain one or more replication and inheritance systems for cloning or expression, one or more markers for selection in the host, and one or more expression cassettes. The inserted coding sequences can be synthesized by standard methods, isolated from natural sources, or prepared as hybrids. Ligation of the coding sequences to transcriptional regulatory elements or to other amino acid encoding sequences can be carried out using established methods. A large number of vectors, including bacterial, fungal, yeast, and mammalian vectors, have been described for replication and/or expression in various host cells or cell-free systems, and may be used with the secretion sequences described herein for simple cloning or protein expression.

Certain embodiments may employ bacterial promoters or regulatory elements. Examples include the arabinose inducible araBAD promoter (pBAD), the lac promoter, the rhamnose inducible rhaP BAD promoter, the T7 RNA polymerase promoter, the trc and tac promoter, the lambda phage promoter p L, and the anhydrotetracycline-inducible tetA promoter/operator. The efficiency of expression may be enhanced by the inclusion of enhancers that are appropriate for the particular bacterial or fungal cell system that is used, such as those described in the literature.

It will be appreciated by one skilled in the art that use of recombinant DNA technologies can improve control of expression of transformed nucleic acid molecules by manipulating, for example, the number of copies of the nucleic acid molecules within the host cell, the efficiency with which those nucleic acid molecules are transcribed, the efficiency with which the resultant transcripts are translated, and the efficiency of post-translational modifications. Additionally, the promoter sequence might be genetically engineered to improve the level of expression as compared to the native promoter. Recombinant techniques useful for controlling the expression of nucleic acid molecules include, but are not limited to, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites), modification of nucleic acid molecules to correspond to the codon usage of the host cell, and deletion of sequences that destabilize transcripts.

The nucleic acids, including parts or all of expression vectors, may be isolated directly from cells, or, alternatively, the polymerase chain reaction (PCR) method can be used to produce the nucleic acids. Primers used for PCR can be synthesized using the sequence information provided herein and can further be designed to introduce appropriate new restriction sites, if desirable, to facilitate incorporation into a given vector for recombinant expression. The nucleic acids can be produced in large quantities by replication in a suitable host cell (e.g., prokaryotic or eukaryotic cells such as bacteria, fungi, yeast, insect or mammalian cells). The production and purification of nucleic acids are described, for example, in Sambrook et al., 1989; F. M. Ausubel et al., 1992, Current Protocols in Molecular Biology, J. Wiley and Sons, New York, N.Y.

The nucleic acids described herein may be used in methods for production of chimeric CbhA polypeptides through incorporation into cells, tissues, or organisms. In some embodiments, a nucleic acid may be incorporated into a vector for expression in suitable host cells. The vector may then be introduced into one or more host cells by any method known in the art. One method to produce an encoded protein includes transforming a host cell with one or more recombinant nucleic acids (such as expression vectors) to form a recombinant cell. The term "transformation" is generally used herein to refer to any method by which an exogenous nucleic acid molecule (i.e., a recombinant nucleic acid molecule) can be inserted into a cell, but can be used interchangeably with the term "transfection."

Non-limiting examples of suitable host cells include cells from microorganisms such as bacteria, yeast, fungi, and filamentous fungi. Exemplary microorganisms include, but are not limited to, bacteria such as strains of *Bacillus brevis, Bacillus megaterium, Bacillus subtilis, Caulobacter crescentus*, and *Escherichia coli* (e.g., BL21 and K12); filamentous fungi from the genera *Trichoderma* (e.g., *T. reesei, T. viride, T. koningii*, or *T. harzianum*), *Penicillium* (e.g., *P. funiculosum*), *Humicola* (e.g., *H. insolens*), *Chrysosporium* (e.g., *C. lucknowense*), *Gliocladium, Aspergillus* (e.g., *A. niger, A. nidulans, A. awamori*, or *A. aculeatus*), *Fusarium, Neurospora, Hypocrea* (e.g., *H. jecorina*), and *Emericella*; and yeasts from the genera *Saccharomyces* (e.g., *S. cerevisiae*), *Pichia* (e.g., *P. pastoris*), or *Kluyveromyces* (e.g., *K. lactis*). Cells from plants such as *Arabidopsis*, barley, citrus, cotton, maize, poplar, rice, soybean, sugarcane, wheat, switch grass, alfalfa, miscanthus, and trees such as hardwoods and softwoods are also contemplated herein as host cells.

Host cells can be transformed, transfected, or infected as appropriate by any suitable method including electroporation, calcium chloride-, lithium chloride-, lithium acetate/polyene glycol-, calcium phosphate-, DEAE-dextran-, liposome-mediated DNA uptake, spheroplasting, injection, microinjection, microprojectile bombardment, phage infection, viral infection, or other established methods. Alternatively, vectors containing the nucleic acids of interest can be transcribed in vitro, and the resulting RNA introduced into the host cell by well-known methods, for example, by injection. Exemplary embodiments include a host cell or population of cells expressing one or more nucleic acid molecules or expression vectors described herein (for example, a genetically modified microorganism). The cells into which nucleic acids have been introduced as described above also include the progeny of such cells.

Vectors may be introduced into host cells such as those from bacteria by direct transformation, in which DNA is mixed with the cells and taken up without any additional manipulation, by conjugation, electroporation, or other means known in the art. Expression vectors may be expressed by bacteria or other host cells episomally or the gene of interest may be inserted into the chromosome of the host cell to produce cells that stably express the gene with or without the need for selective pressure. For example, expression cassettes may be targeted to neutral chromosomal sites by recombination.

Host cells carrying an expression vector (i.e., transformants or clones) may be selected using markers depending on the mode of the vector construction. The marker may be on the same or a different DNA molecule. In prokaryotic hosts, the transformant may be selected, for example, by resistance to ampicillin, tetracycline or other antibiotics. Production of a particular product based on temperature sensitivity may also serve as an appropriate marker.

Host cells may be cultured in an appropriate fermentation medium. An appropriate, or effective, fermentation medium refers to any medium in which a host cell, including a genetically modified microorganism, when cultured, is capable of growing or expressing the chimeric polypeptides described herein. Such a medium is typically an aqueous medium comprising assimilable carbon, nitrogen and phosphate sources, but can also include appropriate salts, minerals, metals and other nutrients. Microorganisms and other cells can be cultured in conventional fermentation bioreactors and by any fermentation process, including batch, fed-batch, cell recycle, and continuous fermentation. The pH of the fermentation medium is regulated to a pH suitable for growth of the particular organism. Culture media and conditions for various host cells are known in the art. A wide range of media for culturing bacteria, for example, are available from ATCC. Exemplary culture/fermentation conditions and reagents are provided in the Examples that follow.

The nucleic acid molecules described herein encode chimeric CbhA polypeptides with amino acid sequences such as that represented by SEQ ID NO:6. As used herein, the terms "protein" and "polypeptide" are synonymous. "Peptides" are defined as fragments or portions of polypeptides, preferably fragments or portions having at least one functional activity as the complete polypeptide sequence. "Isolated" proteins or polypeptides are proteins or polypeptides purified to a state beyond that in which they exist in cells. In certain embodiments, they may be at least 10% pure; in others, they may be substantially purified to 80% or 90% purity or greater. Isolated proteins or polypeptides include essentially pure proteins or polypeptides, proteins or polypeptides produced by chemical synthesis or by combinations of biological and chemical methods, and recombinant proteins or polypeptides that are isolated. Proteins or polypeptides referred to herein as "recombinant" are proteins or polypeptides produced by the expression of recombinant nucleic acids.

Proteins or polypeptides encoded by nucleic acids as well as functional portions or variants thereof are also described herein. Polypeptide sequences may be identical to the amino acid sequence of SEQ ID NO:6, or may include up to a certain integer number of amino acid alterations. Such protein or polypeptide variants retain functionality as cellulases, and include mutants differing by the addition, deletion or substitution of one or more amino acid residues, or modified polypeptides and mutants comprising one or more modified residues. The variant may have one or more conservative changes, wherein a substituted amino acid has similar structural or chemical properties (e.g., replacement of leucine with isoleucine). Alterations may occur at the amino- or carboxy-terminal positions of the reference polypeptide sequence or anywhere between those terminal positions, interspersed either individually among the amino acids in the reference sequence or in one or more contiguous groups within the reference sequence.

In certain embodiments, the polypeptides may be at least about 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:6 and possess cellulase function. Percent sequence identity can be calculated using computer programs (such as the BLASTP and TBLASTN programs publicly available from NCBI and other sources) or direct sequence comparison. Polypeptide variants can be produced using techniques known in the art including direct modifications to isolated polypeptides, direct synthesis, or modifications to the nucleic acid sequence encoding the polypeptide using, for example, recombinant DNA techniques.

Modified polypeptides, including those with post-translational modifications, are also contemplated herein. Isolated polypeptides may be modified by, for example, phosphorylation, methylation, farnesylation, carboxymethylation, geranyl geranylation, glycosylation, acetylation, myristoylation, prenylation, palmitation, amidation, sulfation, acylation, or other protein modifications. They may also be modified with a label capable of providing a detectable signal, either directly or indirectly, including, but not limited to, radioisotopes and fluorescent compounds. The polypeptides may be useful as antigens for preparing antibodies by standard methods. Monoclonal and polyclonal antibodies that specifically recognize the polypeptides disclosed herein are contemplated.

Chimeric polypeptides may be expressed, isolated and used as stand-alone polypeptides. They may also be fused to one or more additional polypeptides (using, for example, recombinant technology) to create a fusion protein with an additional complete polypeptide or a functional domain of a polypeptide. Suitable fusion segments include segments that can enhance a protein's stability, provide other desirable biological activity, or assist with the purification of the protein (e.g., by affinity chromatography). A suitable fusion segment can be a domain of any size that has the desired function (e.g., imparts increased stability, solubility, action or biological activity; or simplifies purification of a protein).

Chimeric polypeptides may be detected by any assay known in the art to detect a protein of interest. Examples include enzymatic activity assays, detection with specific antibodies (immunoblotting, ELISA, etc.), and other suitable detection techniques.

Chimeric polypeptides may also be isolated or recovered from the media used in host cell cultures or cell-free expression systems. The phrase "recovering the protein" refers to collecting the whole culture medium containing the protein and need not imply additional steps of separation or purification. Proteins can be purified using a variety of standard protein purification techniques, such as affinity chromatography, ion exchange chromatography, filtration, electrophoresis, hydrophobic interaction chromatography, gel filtration chromatography, reverse phase chromatography, concanavalin A chromatography, chromatofocusing, differential solubilization, preparative disc-gel electrophoresis, isoelectric focusing, HPLC, reversed-phase HPLC, or countercurrent distribution. The polypeptide may contain an additional protein or epitope tag that facilitates detection or purification, such as c-myc, haemagglutinin (HA), polyhistidine, GLU-GLU, FLAG-tag, glutathione-S-transferase (GST), green fluorescent protein (GFP), or maltose binding protein (MBP). Such tags may be removed following the recovery of the polypeptide.

Polypeptides may be retrieved, obtained, or used in "substantially pure" form, a purity that allows for the effective use of the protein in any method described herein or known in the art. For a protein to be most useful in any of the methods described herein or in any method utilizing enzymes of the types described herein, it is most often substantially free of contaminants, other proteins and/or chemicals that might interfere or that would interfere with its use in the method (e.g., that might interfere with enzyme activity), or that at least would be undesirable for inclusion with a protein.

Methods for degrading cellulose and materials containing cellulose using the chimeric CbhA polypeptides are also provided herein. For example, the chimeric CbhA polypeptides may be used in compositions to help degrade (e.g., by liquefaction) a variety of cellulose products (e.g., paper, cotton, etc.) in landfills. The chimeric CbhA polypeptides may also be used to enhance the cleaning ability of detergents, function as a softening agent or improve the feel of cotton fabrics (e.g., stone washing or biopolishing) or in feed compositions.

Cellulose containing materials may also be degraded to sugars using the chimeric CbhA polypeptides. Ethanol may be subsequently produced from the fermentation of sugars derived from the cellulosic materials. Exemplary cellulose-containing materials include bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, corn fiber, grasses, wheat, wheat straw, barley, barley straw, hay, rice straw, switchgrass, waste paper, sugar cane bagasse, sorghum, soy, components obtained from milling of grains, trees, branches, roots, leaves, wood (e.g., poplar) chips, sawdust, shrubs and bushes, vegetables, fruits, flowers and animal manure.

Biofuels such as ethanol may be produced by saccharification and fermentation of lignocellulosic biomass such as trees, herbaceous plants, municipal solid waste and agricultural and forestry residues. Typically, saccharification is carried out by contacting the lignocellulosic biomass with an enzyme cocktail that includes one or more Family 7 cellulases such as the chimeric polypeptides described herein. Such enzyme cocktails may also contain one or more additional cellulases (e.g., a Family 7 cellulase such as Cel7A from *T. reesei*), endoglucanases (such as the Family 5 endoglucanase E1 from *Acidothermus cellulolyticus*) or one or more β-glucosidases (e.g., a β-glucosidase from *A. niger*) to optimize hydrolysis of the lignocelluloses. Additional suitable endoglucanases include EGI, EGII, EGIII, EGIV, EGV or Cel7B (e.g., Cel7B from *T. reesei*). Enzyme cocktails may also include accessory enzymes such as hemicellulases, pectinases, oxidative enzymes, and the like.

Enzymes with the ability to degrade carbohydrate-containing materials, such as cellulases with endoglucanase activity, exoglucanase activity, or β-glucosidase activity, or hemicellulases with endoxylanase activity, exoxylanase activity, or β-xylosidase activity may be included in enzyme cocktails. Examples include enzymes that possess cellobiohydrolase, α-glucosidase, xylanase, β-xylosidase, α-galactosidase, β-galactosidase, α-amylase, glucoamylases, arabinofuranosidase, mannanase, β-mannosidase, pectinase, acetyl xylan esterase, acetyl mannan esterase, ferulic acid esterase, coumaric acid esterase, pectin methyl esterase, laminarinase, xyloglucanase, galactanase, glucoamylase, pectate lyase, chitinase, exo-β-D-glucosaminidase, cellobiose dehydrogenase, ligninase, amylase, glucuronidase, ferulic acid esterase, pectin methyl esterase, arabinase, lipase, glucosidase or glucomannanase activities.

A lignocellulosic biomass or other cellulosic feedstock may be subjected to pretreatment at an elevated temperature in the presence of a dilute acid, concentrated acid or dilute alkali solution for a time sufficient to at least partially hydrolyze the hemicellulose components before adding the enzyme cocktail. Additional suitable pretreatment regimens include ammonia fiber expansion (AFEX), treatment with hot water or steam, or lime pretreatment.

Separate saccharification and fermentation is a process whereby cellulose present in biomass is converted to glucose that is subsequently converted to ethanol by yeast strains. Simultaneous saccharification and fermentation is a process whereby cellulose present in biomass is converted to glucose and, at the same time and in the same reactor, converted into ethanol by yeast strains. Enzyme cocktails may be added to the biomass prior to or at the same time as the addition of a fermentative organism.

The resulting products after cellulase degradation may also be converted to products other than ethanol. Examples include conversion to higher alcohols, hydrocarbons, or other advanced fuels via biological or chemical pathways, or combination thereof.

EXAMPLES

Example 1

Cloning, Expression, and Purification

Nucleic acids encoding the proteins or protein domains were synthesized directly or were cloned from *C. thermocellum*. Cellulase or scaffoldin genes were amplified from the genomic DNA of *C. thermocellum* (ATCC 27405), using the primers listed in Table 1.

TABLE 1

| Primer | Nucleotide sequence | Gene cloning |
|---|---|---|
| F-CelG-NheI | ACAGCAGCTAGCGCCGTCGACAGCAAC AACG (SEQ ID NO: 9) | CelG |
| R-CelG-XhoI | TGTTGACTCGAGGGTGGTGTGCGGCAG TTTGTC (SEQ ID NO: 10) | CelG |
| F-CelG-XhoI | ACAGCACTCGAGGCCGTCGACAGCAAC AAC (SEQ ID NO: 11) | CelG |

TABLE 1 -continued

| Primer | Nucleotide sequence | Gene cloning |
|---|---|---|
| F-CelA-NcoI | CTGTGTCCATGGCAGGTGTGCCTTTTA ACACA (SEQ ID NO: 12) | CelA |
| R-CelA-XhoI | CCCATTCTCGAGATAAGGTAGGTGGGG TATGC (SEQ ID NO: 13) | CelA |
| F-CelA-XhoI | ACTGTGCTCGAGGCAGGTGTGCCTTTT AA (SEQ ID NO: 14) | CelA |
| F-CelR-NcoI | CTGTTTCCATGGCAGACTATAACTATG GAGAA (SEQ ID NO: 15) | CelR |
| R-CelR-XhoI | ACGATACTCGAGTGAATTTCCGGGTAT GGTTG (SEQ ID NO: 16) | CelR |
| F-CelR-XhoI | CCTGTTCTCGAGGCAGACTATAACTAT GGAG (SEQ ID NO: 17) | CelR |
| F-CelS-XhoI | ACTGCACTCGAGGGTCCTACAAAGGCA CCTA (SEQ ID NO: 18) | CelS |
| R-CelS-XhoI | ATCAGTTTTGCTCGAGGTTCTTGTACG GCAATGTAT (SEQ ID NO: 19) | CelS |
| F-CelY-XhoI | AGCTTTCTCGAGTCCAGACAATCATCC AATTC (SEQ ID NO: 20) | CelY |
| R-CelY-XhoI | AGTTTCCTCGAGTGAATTGCTGTCATC AGAGT (SEQ ID NO: 21) | CelY |
| F-CbhA-NdeI | TCCGTGCATATGTTAGAAGATAATTCT TCGACT (SEQ ID NO: 22) | CbhA |
| R-CbhA-XhoI | CAGATTCTCGAGTCGATATGGCAATTC TTCTAT (SEQ ID NO: 23) | CbhA |

Genes encoding cellulases, monoscaffoldins and multifunctional cellulases were overexpressed in the BL21(DE3) strain of *E. coli* (Stratagene, La Jolla, Calif.)) in the presence of 0.3 mM IPTG at either 16° C. or 37° C. Recombinant proteins were purified in His-tagged form by nickel-nitrilotriacetic acid (Ni-NTA) affinity chromatography (Qiagen, Valencia, Calif.). Table 2 illustrates chimeric proteins made and their module structure.

TABLE 2

| Gene or gene components | Module structure |
|---|---|
| CelG | GH5-Doc |
| CelA | GH8-Doc |
| CelR | GH9-CBM3c-Doc |
| CbhA$^a$-linker1-doc | CBM4-Ig-GH9-linker1-Doc |
| CbhA$^a$-linker3-doc | CBM4-Ig-GH9-linker3-Doc |
| CbhA$^a$-linker1-CelG | CBM4-Ig-GH9-linker1-GH5-Doc |
| CbhA$^a$-linker2-CelG | CBM4-Ig-GH9-linkler2-GH5-Doc |
| CbhA$^a$-linker3-CelG | CBM4-Ig-GH9-linker3-GH5-Doc |
| CbhA$^a$-linker1-CelA | CBM4-Ig-GH9-linker1-GH8-Doc |
| CbhA$^a$-linker2-CelA | CBM4-Ig-GH9-linker2-GH8-Doc |
| CbhA$^a$-linker3-CelA | CBM4-Ig-GH9-linker3-GH8-Doc |

TABLE 2-continued

| Gene or gene components | Module structure |
|---|---|
| CbhA[a]-linker1-CelR | CBM4-Ig-GH9-linker1-GH9-CBM3c-Doc |
| CbhA[a]-linker2-CelR | CBM4-Ig-GH9-linker2-GH9-CBM3c-Doc |
| CbhA[a]-linker3-CelR | CBM4-Ig-GH9-linker3-GH9-CBM3c-Doc |
| CbhA[a]-CelS | CBM4-Ig-GH9-GH48-Doc |
| CbhA[a]-linker3-CelS | CBM4-Ig-GH9-linker3-GH48-Doc |
| CbhA[a]-CelY[b] | CBM4-Ig-GH9-GH48 |
| CbhA[a]-linker3-CelY[b] | CBM4-Ig-GH9-linker3-GH48 |
| Monoscaffoldin (truncated CipA) | Cohesin 2-CBM3a |
| Chimera1 of CbhA | CBM4-Ig-GH9-linker1-CBM3b-Doc |
| Chimera2 of CbhA | CBM4-Ig-GH9-linker2-CBM3b-Doc |
| CbhA | CBM4-Ig-GH9-linker3-CBM3b-Doc |

GH, glycosyl hydrolase family; CBM, carbohydrate binding module; Coh, type-I cohesin; Doc, type-I dockerin; Ig, immunoglobulin-like fold;
[a]truncated CbhA (CBM4-Ig-GH9),
[b]truncated CelY (GH48 module only).

Example 2

Cellulase Activity Assay

Constructs or natural enzyme sequences ending in a C-terminal "doc" (dockerin) were assayed after being mixed with a "binding adaptor" consisting of the fusion of cohesin 2 (the second of the nine Type-I cohesins in the *C. thermocellum* scaffoldin protein CipA) with a CBM3a module from the same scaffoldin to provide the construct or enzyme with a C-terminal family-3 carbohydrate-binding module which could bind to crystalline cellulose.

Cellulase activity was measured under anaerobic conditions using microcrystalline cellulose (Avicel PH-101, Fluka, Sigma-Aldrich Corp., St. Louis, Mo.) as substrate. Enzymes were loaded at a standard molar concentration of 2.0 micromoles/L (or 400 µmol/g cellulose), working against a standard substrate (Avicel) loading of 5.0 mg/mL. Assays were carried out at 60° C. in 20 mM acetate, pH 5.0, containing 10 mM $CaCl_2$, 5.0 mM L-cysteine and 2 mM EDTA to promote stability of the anaerobe-derived cellulases. Each assay mixture also included *Aspergillus niger* β-glucosidase (chromatographically-purified from the commercial mixture Novozym 188 (Novozymes North America, Franklinton, N.C., USA.)) at a concentration of 0.005 mg/mL (or 1.0 mg/g of cellulose substrate), to maintain cellobiose concentrations below the levels at which cellobiose-inhibition of the enzymes is measurable.

Assays were carried out in triplicate, in initial digestion volumes of 1.0 mL in crimp-sealed 2.0 mL HPLC vials, with constant mixing by inversion at 10/min in a rotating incubator inside a glove box maintaining an atmosphere of 5% hydrogen, 95% nitrogen. At designated times during the digestions, representative 0.1 mL aliquots of liquid and solids were withdrawn for analysis, with the digestion vials being opened and then re-capped anaerobically inside the glove-box. The withdrawn aliquots of digestion mixture were diluted 18-fold with deionized water in sealed 2.0 mL HPLC vials, which were then immersed for 10 minutes in a boiling water bath to terminate the enzyme reactions. The diluted digestion-mixture aliquots were then syringe-filtered (0.2 µm) before quantification of released sugars by HPLC. HPLC sugar analyses were carried out on a Bio-Rad (Hercules, Calif.) HPX-87H column operated at 65° C. with 0.01 N $H_2SO_4$ (0.6 mL/min) as mobile phase in an Agilent (Santa Clara, Calif.) 1100-series liquid chromatograph with refractive-index detection.

Example 3

Linkers for Construction of Chimeras

As shown in FIG. 6, linkers from the following sources were used: *Clostridium thermocellum* Orf2P (linked), *Caldicellulosiruptor bescii* CelA (linker2), and two consecutive X1 domains from wild-type *Clostridium thermocellum* CbhA (linker3) (FIG. 6). These three linkers have amino-acid compositions characterized as PT (proline/threonine-rich, linker2), or "PT and G" (proline/threonine-rich with additional glycine-rich regions, as in linker1) and as "generic" with no unique compositional features (Linker3).

Example 4

Chimeric Enzymes and Activities

Two CbhA chimeras in which both of the consecutive X1 domains of CbhA have been replaced were made. In one case, the domains were replaced by a linker (linker1) isolated from the *C. thermocellum* scaffoldin gene Orf2P to form Chimera1 (CBM4-Ig-GH9-linker1-CBM3b-Doc), and in the other case by a linker (linker2) from *Caldicellulosiruptor bescii* CelA (Chimera2, CBM4-Ig-GH9-linker 2-CBM3b-Doc).

Activities against crystalline cellulose of wild type CbhA and its two chimeras were measured in two different experimental setups. In one method, the three constructs were assayed in "bare-dockerin" form (i.e., no cohesin-CBM3a construct was added to augment the chimera with a second CBM3 at the C-terminal). In the second experimental approach, each dockerin-bearing construct was mixed before assay, with a monoscaffoldin binding-adaptor formed by fusing cohesin2 and CBM3a of *C. thermocellum* cipA.

Progress curves for saccharification of Avicel by the bare-dockerin CbhA are shown in FIG. 8A. At the end of a 119 hour digestion, Chimera2, with the PT-composition CelA linker, had solubilized 75% as much of the Avicel as had the construct retaining the generic, wild-type linker; chimera1, while the PT & G Orf2P linker, solubilized 62% as much Avicel as did the wild-type construct.

The addition of a Family-3a CBM to the C-terminus of each of the above three constructs results in striking differences in their relative activities against Avicel. All three of the constructs have their activities boosted by addition of the CBM3a, but the two constructs with non-native linker domains are helped more than is the construct that has the wild-type repeated X1 domains. Based on yields of soluble sugar after 119 hour digestion, the activities of the constructs with linker1 and 2 are increased by factors of 1.55 and 1.73, with respect to their yields without the Coh2-CBM3 adduct, whereas the 119 hour yield for the wild-type (linker3) construct is increased by a factor of only 1.09. As a result of the greater enhancement of activity of the "linker2" and "linker1" constructs, the 119 hour yield of the linker2 construct is now 1.2 times that of the wild-type-linker construct, and the yield of the digestion by the linker1 construct has pulled up to 0.88 times that of the wild-type (from 0.62 times wild-type without the Coh2-CBM3a binding adaptor).

Example 5

Influence of Linkers on Enzyme Activities

The activities of multimodular cellulase peptides incorporating more than one catalytic domain may depend not only upon the types of activities being combined, but also upon the ordering of the catalytic domains in the peptide, and upon the properties of the linker segments used to connect them. The importance of linker-segment properties is illustrated in FIGS. 9 and 10.

Figure 9:
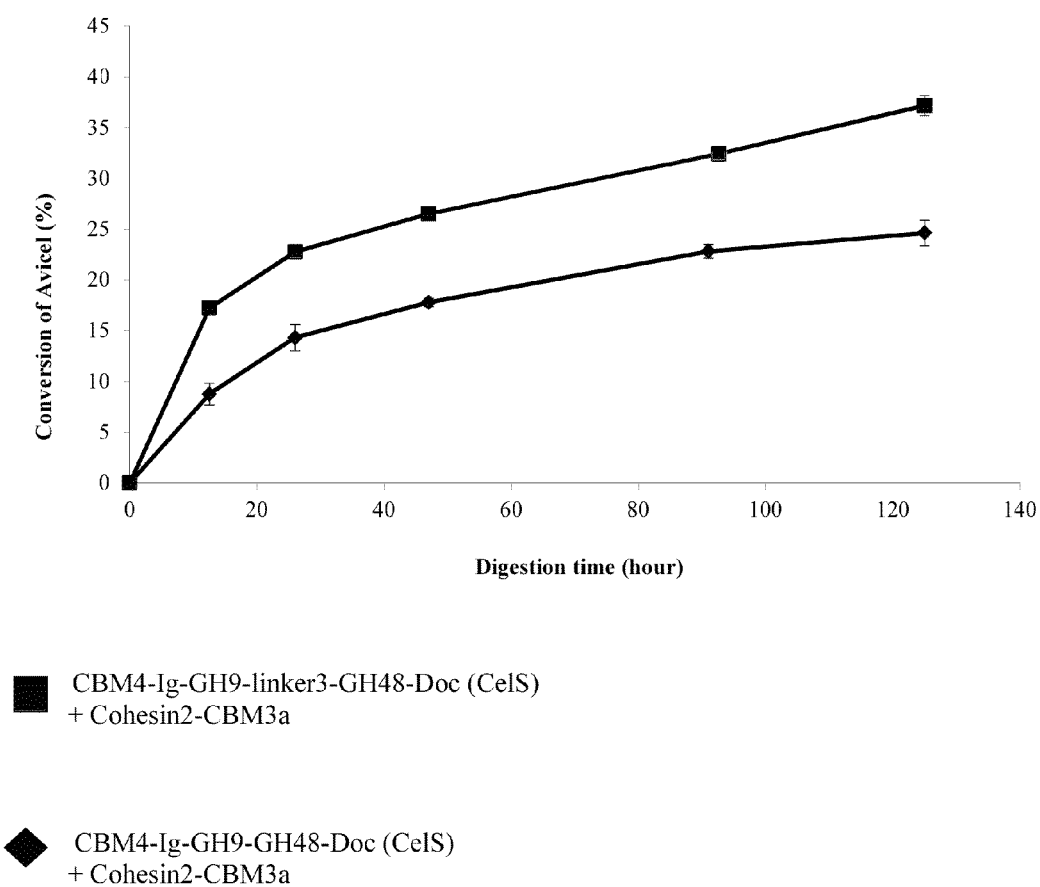
FIG. 9 shows the contribution of linker3 to activity of cellulosomal multifunctional cellulase. Cellulosomal cellulases were combined with monoscaffoldin of Coh-CBM3a to form minicellulosomes first, and then activity of these minicellulosomes was assayed.
Figure 10:
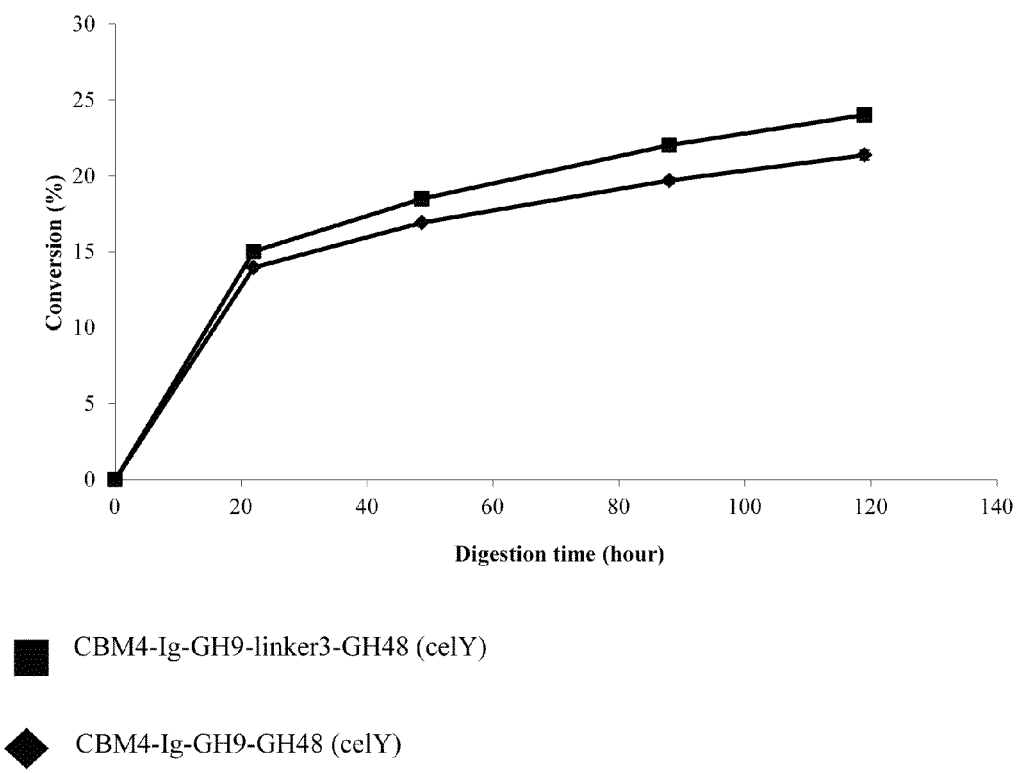
FIG. 10 shows the contribution of linker3 to activity of non-cellulosomal multifunctional cellulase.

FIG. 9 compares the Avicelase activities of two engineered multifunctional (multi-catalytic) cellulases each containing, in the same order, a truncated *C. thermocellum* CbhA (N-terminal CBM4 through the GH9 catalytic module) connected at its C-terminus to another cellulosomal catalytic module (GH48, CelS). The difference between the two constructs is in the way in which the two catalytic domains are connected. The upper curve in FIG. 9 (for the more active construct) has the two catalytic domains connected through the two X1 sequences found C-terminal to the GH9 domain in CbhA; the lower curve shows saccharification by a construct in which the GH48 domain was connected directly to the GH9 domain, without any special linker domain. The construct lacking the special linker segment that may be required to provide the proper spacing and/or flexibility to allow both catalytic domains to engage the substrate effectively, is seen to covert 34% less of the substrate in 125 h than is converted by the construct with the wild-type CbhA double-X1 domains (Linker 3).

In a manner similar to that used for the constructs in FIG. 9, the same C-terminal portion of *C. thermocellum* CbhA was connected, in one case directly and, in the other, through an intervening linker 3 (double X1) segment, to another *C. thermocellum* GH48 catalytic domain, this time from the non-cellulosomal CelY. The resulting difference in activity (FIG. 10), although not as dramatic as seen in FIG. 9, appears statistically significant given the relatively small standard errors of the triplicate determinations and is in the same direction, i.e., the construct with the intervening linker solubilizes more of the cellulose in a 119 hour digestion than does the construct with the two catalytic domains linked directly.

In a systematic study aimed at further elucidating the contributions of linker-segment properties (and of combinations of catalytic domains) to multifunctional cellulase activity, a total of nine multifunctional cellulase genes were designed to test a 3×3 matrix in which each of three *C. thermocellum* catalytic domains was in turn connected to the C-terminus of the truncated CbhA described earlier, by means of each of three compositionally different linker sequences (FIG. 6). Catalytic modules representing glycohydrolase families 5, 8, and 9 were cloned from the genes for CelG, CelA, and CelR respectively. Genes for other modules, such as those for CBM3c and 4, and for the Ig-like domains and dockerin-1 were those contiguous to the targeted catalytic domains in the genome and were obtained along with the catalytic domains as single gene segments. Constructs shown in Table 3 were built using these gene segments, cloned into *E. coli*, overexpressed and purified.

TABLE 3

| Gene component | Module structure | Conversion of Avicel (%) |
|---|---|---|
| CbhA$^a$-linker1-CelG | CBM4-Ig-GH9-linker1-GH5-Doc | 48.9 ± 0.77 |
| CbhA$^a$-linker2-CelG | CBM4-Ig-GH9-linkler2-GH5-Doc | 57.5 ± 0.92 |
| CbhA$^a$-linker3-CelG | CBM4-Ig-GH9-linker3-GH5-Doc | 58.6 ± 1.31 |
| CbhA$^a$-linker1-CelA | CBM4-Ig-GH9-linker1-GH8-Doc | 41.5 ± 0.10 |
| CbhA$^a$-linker2-CelA | CBM4-Ig-GH9-linker2-GH8-Doc | 47.6 ± 0.67 |
| CbhA$^a$-linker3-CelA | CBM4-Ig-GH9-linker3-GH8-Doc | 50.2 ± 0.29 |
| CbhA$^a$-linker1-CelR | CBM4-Ig-GH9-linker1-GH9-CBM3c-Doc | 51.5 ± 0.28 |
| CbhA$^a$-linker2-CelR | CBM4-Ig-GH9-linker2-GH9-CBM3c-Doc | 45.6 ± 0.15 |

TABLE 3-continued

| Gene component | Module structure | Conversion of Avicel (%) |
|---|---|---|
| CbhA$^a$-linker3-CelR | CBM4-Ig-GH9-linker3-GH9-CBM3c-Doc | 40.6 ± 0.39 |

The activities of additional artificial multifunctional cellulases have been tested, in a 3×3 matrix of three different pairs of catalytic domains and three different linker sequences. The results of assays against Avicel PH101 (Table 3) showed that the effectiveness of a given linker in construction of active multifunctional cellulases is dependent upon the identity of the catalytic (and other) domains being connected. In the case of pairing of the N-terminal sequence CBM4-Ig-GH9 with the C-terminal sequence GH5-Doc, the multifunctional enzyme constructed using Linker3 released almost 20% more soluble sugar in a 70.3 hour digestion than did the same two sequences connected by Linker1 (58.6% of potential soluble sugar for Linker3 vs. 48.9% for Linker1). In contrast, however, when the C-terminal "catalytic" sequence was changed to GH9-CBM3c-Doc (with the same N-terminal sequence as before), the apparent effectiveness of the two linkers was reversed, with the multifunctional connected by Linker1 releasing almost 27% more soluble sugar than did the Linker3 construct. Broader trends in this data set may be seen in the orthogonal array presentation of Table 4. CelG and CelA prefer the linkers in the order Linker3>Linker2>Linker1. CelR reverses this preference, with activities decreasing in the order Linker1>Linker2>Linker3. From the viewpoint of the linkers, Linker3 and Linker2 both prefer the C-terminal catalytic domains in the order CelG>CelA>CelR. Linker1 departs from this trend—the variation of yield with C-terminal catalytic domain is not monotonic. Yield is less with CelA than with CelG as C-terminal catalytic domain, as is the case with Linker2 and Linker3, but linking CelR to truncated CbhA through Linker1 results in a construct more active than either the corresponding CelA OR CelG Linker1 constructs.

TABLE 4

| | CelG (GH5) | CelA(GH8) | CelR(GH9) |
|---|---|---|---|
| Linker 1 | 48.9 | 41.5 | 51.5 |
| Linker2 | 57.5 | 47.6 | 45.6 |
| Linker3 | 58.6 | 50.2 | 40.6 |

These results show that choice of linkers is important for the activity of multifunctional cellulases, and that the contributions of linkers to activity of multifunctional cellulases are dependent on the combinations of catalytic modules.

Example 6

Intra-Molecular Synergy

In order to investigate the intra-molecular synergy resulting from combining catalytic domains into multifunctional cellulases, Avicelase activities of some of the artificial multifunctional cellulases listed in Table 3 were compared with the activities of their component modules assayed as simple mixtures, rather than as covalently-linked multifunctionals (Table 5). Out of five multifunctional cellulases evaluated in this way, four showed significant intra-molecular synergism, i.e., CBM4-Ig-GH9-linker1-GH5-Doc, CBM4-Ig-GH9-linker3-GH5-Doc, CBM4-Ig-GH9-linker1-GH8-Doc, CBM4-Ig-GH9-linker1-GH9-CBM3c-Doc displayed intramolecular synergism of 1.12, 1.27, 1.53 and 1.48, respectively, when compared with simple mixtures of their component segments, assayed at the same molar loadings. One of the multifunctional cellulases, CBM4-Ig-GH9-linker3-GH9-CBM3c-Doc did not show significant synergy, but neither did it show any reduction of activity relative to that of a simple mixture of the two parent individual cellulases. The highest observed intra-molecular synergism was 1.53, demonstrating that construction of multifunctional cellulases is a practical approach to improving cellulase activity.

Traditional synergism factors/ratios are also provided in Table 5, comparing the totals of sugar release by the N-terminal and C-terminal segments of each construct when assayed separately with sugar release by a simple mixture of the two, operating in the same assay vial. The "endo-exo" synergism for simple mixtures of some individual cellulases, such as the mixture of GH9-CBM3c-Doc and CBM4-GH9-Ig-linker1-Doc (0.73) was not high, but their intra-molecular synergy of CBM4-GH9-Ig-linker1-GH9-CBM3c-Doc could reach a considerably higher level (1.48) upon connection of the two by an appropriate linker. A value less than unity for the synergism ratio for the simple mixture does not necessarily indicate negative synergism, or interference, but it does hint at relatively weak or even negligible synergism, making more impressive the synergism arising from linking the domains. This demonstrates that construction of artificial multifunctional cellulases is a valid approach to improving the activity of cellulases.

In combinations of two catalytic modules and linkers, it is difficult to find a general rule for design of multifunctional cellulases based on current results. For example, in the architecture of CBM4-Ig-GH9-linker1-GH5-Doc and CBM4-Ig-GH9-linker3-GH5-Doc, intra-molecular synergism caused by linker3 is better than that of linker1, however, in CBM4-Ig-GH9-linker1-GH9-CBM3c-Doc and CBM4-Ig-GH9-linker3-GH9-CBM3c-Doc, linker 1 is better. The effect of a given linker appears to be sensitive to the properties of the particular combination of modules being linked.

Example 7

Time Course Activities of Chimeric Enzymes

Figure 11A:
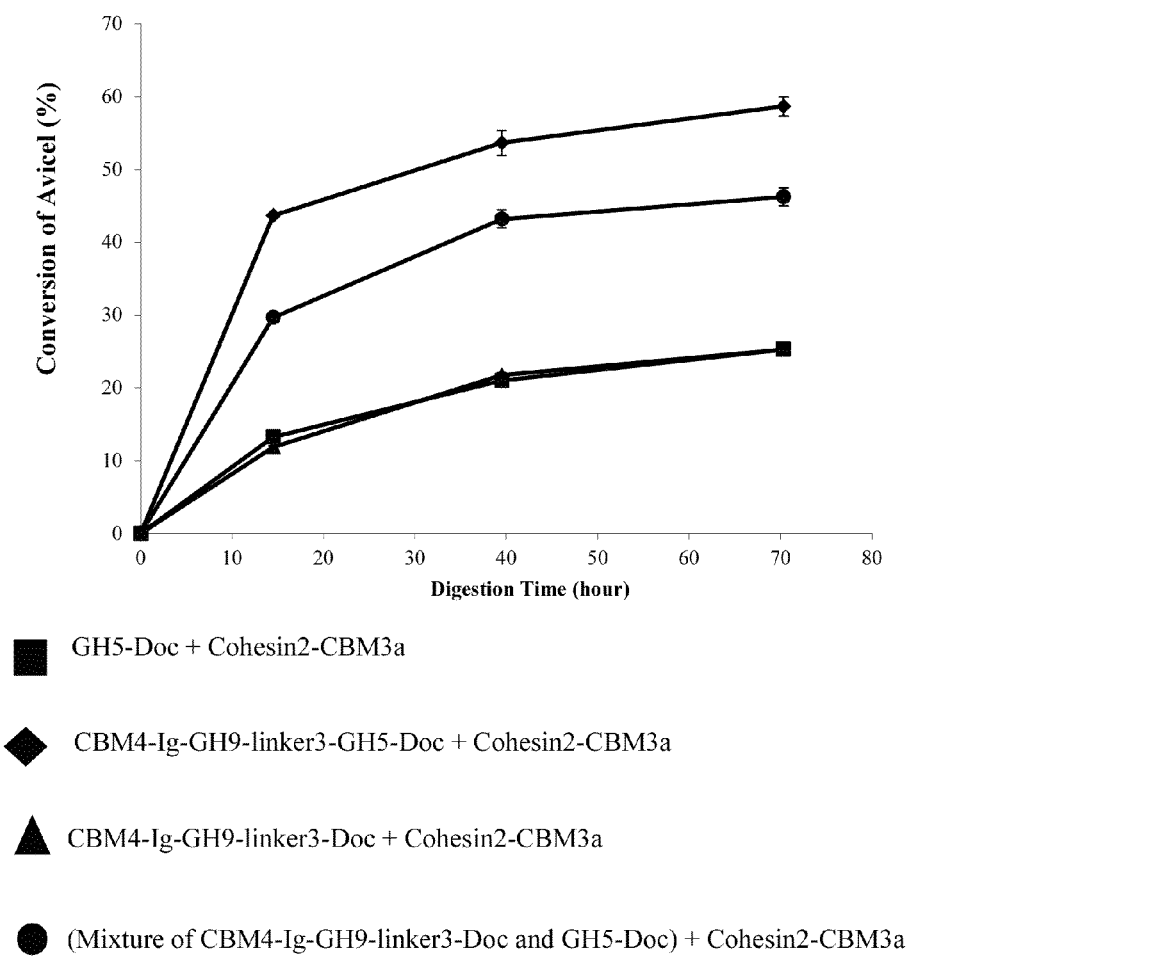
FIG. 11A-C shows the activity of multifunctional cellulase and its intra-molecular synergy. Cellulosomal cellulases were combined with monoscaffoldin of Coh-CBM3a to form mini-cellulosomes first, and then activity of these minicellulosomes was assayed.
Figure 11B:
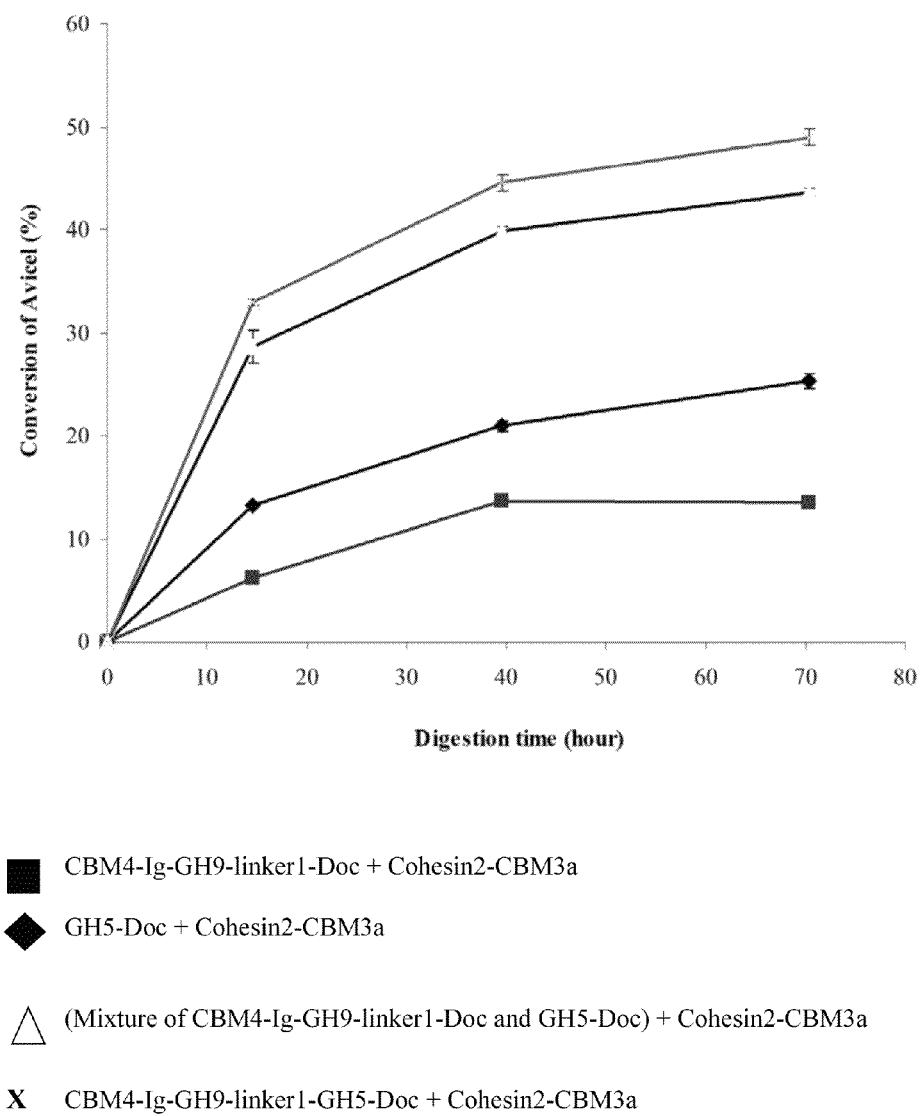
Figure 11C:
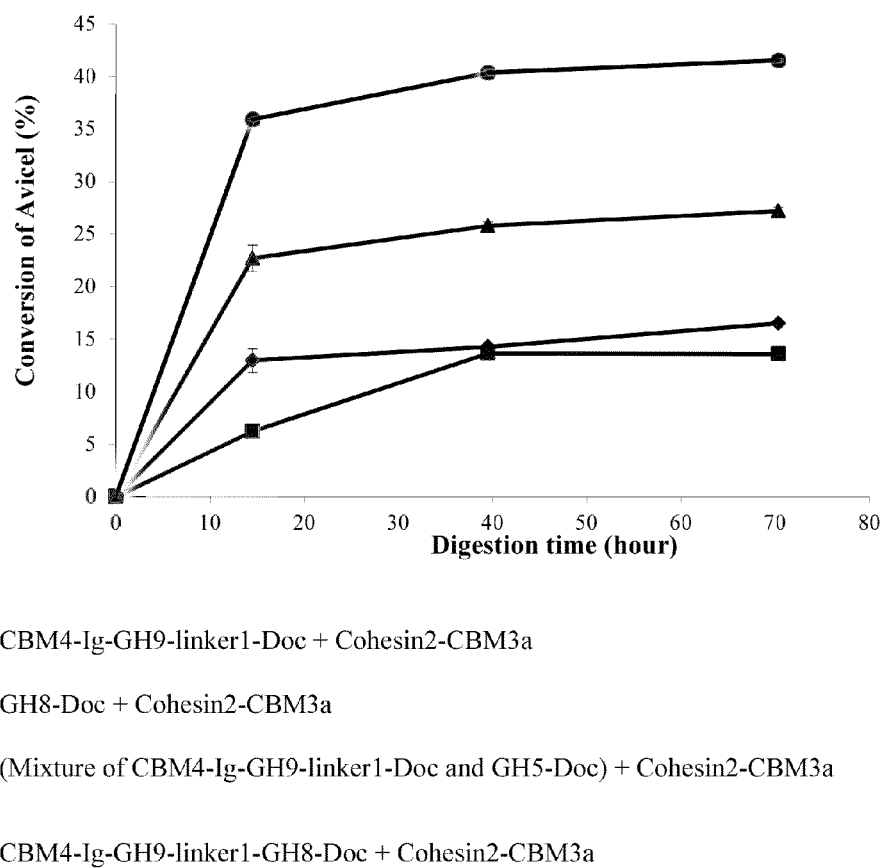

FIG. 11 displays progress-curve data for three of the multifunctional cellulases whose activities are described in Table 5, along with curves for their respective single-catalytic-domain constituents. The pattern observed in the overall figure is the difference in the shapes of the curves. The GH9-linker1-GH8 construct, which, while exhibiting the greatest degree of intramolecular synergism actually delivers the smallest ultimate (70.3 hour) conversion (FIG. 11C), is relatively quick out of the blocks, delivering 86.4% of its final (70.3 hour) conversion in the first 14.5 hours of the digestion. The other two multifunctional constructs, GH9-linker3-GH5 (FIG. 11A) and GH9-Linker1-GH5 peptides, reach 74.4% and 67.3%, respectively, of their 70.3 hour conversions in the first 14.5 hours. Similar patterns are observed in comparing the respective curves for the simple mixture of the GH8-containing monofunctional component peptides, and the GH8 component by itself, with their GH5 counterparts.

The Examples discussed above are provided for purposes of illustration and are not intended to be limiting. Still other embodiments and modifications are also contemplated.

While a number of exemplary aspects and embodiments have been discussed above, those of skill in the art will recognize certain modifications, permutations, additions and sub combinations thereof. It is therefore intended that the following appended claims and claims hereafter introduced are interpreted to include all such modifications, permutations, additions and sub-combinations as are within their true spirit and scope.

TABLE 5

| Gene components | Module structure | Conversion of Avicel (%) | Endo-exo synergy | Intra-molecular synergism |
| --- | --- | --- | --- | --- |
| CelG | GH5-Doc | 25.3 ± 0.72 | | |
| CbhA$^a$-linker1-doc | CBM4-Ig-GH9-linker1-Doc | 13.6 ± 0.24 | | |
| Mixture of CelG and CbhA$^a$-linker1-doc | Mixture of GH5-Doc and CBM4-Ig-GH9-linker1-Doc | 43.7 ± 0.32 | 1.11 | |
| CbhA$^a$-linker1-CelG | CBM4-Ig-GH9-linker1-GH5-Doc | 48.9 ± 0.77 | | 1.12 |
| CelG | GH5-Doc | 25.3 ± 0.72 | | |
| CbhA$^a$-linker3-doc | CBM4-Ig-GH9-linker3-Doc | 25.3 ± 0.29 | | |
| Mixture of CelG and CbhA$^a$-linker3-doc | Mixture of GH5-Doc and CBM4-Ig-GH9-linker3-Doc | 46.2 ± 1.25 | 0.91 | |
| CbhA$^a$-linker3-CelG | CBM4-Ig-GH9-linker3-GH5-Doc | 58.6 ± 1.31 | | 1.27 |
| CelA | GH8-Doc | 13.0 ± 0.11 | | |
| CbhA$^a$-linker1-doc | CBM4-Ig-GH9-linker1-Doc | 13.6 ± 0.24 | | |
| Mixture of CelA and CbhA$^a$-linker 1-doc | Mixture of GH8-Doc and CBM4-Ig-GH9-linker1-Doc | 27.2 ± 0.37 | 1.02 | |
| CbhA$^a$-linker1-CelA | CBM4-Ig-GH9-linker1-GH8-Doc | 41.5 ± 0.10 | | 1.53 |
| CelR | GH9-CBM3c-Doc | 30.6 ± 0.33 | | |
| CbhA$^a$-linker1-doc | CBM4-Ig-GH9-linker1-Doc | 13.6 ± 0.24 | | |
| Mixture of CelR and CbhA$^a$-linker1-doc | Mixture of GH9-CBM3c-Doc and CBM4-Ig-GH9-linker1-Doc | 34.9 ± 0.44 | 0.73 | |
| CbhA$^a$-linker1-CelR | CBM4-Ig-GH9-linker1-GH9-CBM3c-Doc | 51.5 ± 0.28 | | 1.48 |
| CelR | GH9-CBM3c-Doc | 30.6 ± 0.33 | | |
| CbhA$^a$-linker3-Doc | CBM4-Ig-GH9-linker3-Doc | 25.3 ± 0.29 | | |
| Mixture of CelR and CbhA$^a$-linker3-Doc | Mixture of GH9-CBM3c-Doc and CBM4-Ig-GH9-linker3-Doc | 39.4 ± 0.11 | 0.70 | |
| CbhA$^a$-linker3-CelR | CBM4-Ig-GH9-linker3-GH9-CBM3c-Doc | 40.6 ± 0.39 | | 1.03 |

We claim:

1. An isolated nucleic acid molecule encoding a chimeric CbhA polypeptide comprising domains from *Clostridium thermocellum* cellobiohydrolase A (CbhA) and *Caldicellulosiruptor bescii* cellobiohydrolase A (CelA) polypeptides, wherein the chimeric CbhA polypeptide has an amino acid sequence at least 95% identical to "SEQ ID NO:6," and wherein the chimeric CbhA polypeptide has a cellulase activity at least 1.5-fold greater than the wild-type CbhA polypeptide.

2. The isolated nucleic acid molecule of claim 1, wherein the chimeric CbhA polypeptide comprises the linker domain from the *Caldicellulosiruptor bescii* CelA polypeptide.

3. The isolated nucleic acid molecule of claim 1, wherein the chimeric CbhA polypeptide has a cellulase activity at least 2-fold greater than the wild-type CbhA polypeptide.

4. The isolated nucleic acid molecule of claim 1, wherein the chimeric CbhA polypeptide has an amino acid sequence at least 97% identical to SEQ ID NO:6.

5. The isolated nucleic acid molecule of claim 1, wherein the chimeric CbhA polypeptide has the amino acid sequence of SEQ ID NO:6.

6. The isolated nucleic acid molecule of claim 1, further comprising a promoter operably linked to the nucleic acid molecule.

7. The isolated nucleic acid molecule of claim 6, wherein the promoter allows expression of the nucleic acid in a bacterial host cell.

8. An expression vector comprising the nucleic acid molecule of claim 1.

9. An isolated host cell that expresses a recombinant polypeptide encoded by the nucleic acid molecule of claim 1.

10. The host cell of claim 9, wherein the cell is an *E. coli* cell.

11. An isolated chimeric CbhA polypeptide encoded by the nucleic acid molecule of claim 1.

12. A method for degrading cellulose or lignocellulosic biomass, comprising contacting a cellulose containing material or lignocellulosic biomass with the isolated chimeric CbhA polypeptide of claim 11.

13. A method for producing a biofuel from lignocellulosic biomass, comprising:
   a) contacting the lignocellulosic biomass with an enzyme cocktail comprising the isolated chimeric CbhA polypeptide of claim 11 to generate sugars; and
   b) converting the sugars to a biofuel by fermentation.

14. The method of claim 13, wherein the enzyme cocktail further comprises an endoglucanase, a β-glucosidase, or both.

* * * * *